United States Patent
Yang et al.

(10) Patent No.: US 9,428,511 B2
(45) Date of Patent: Aug. 30, 2016

(54) IMIDAZOPYRIDAZINE JAK3 INHIBITORS AND THEIR USE FOR THE TREATMENT OF INFLAMMATORY AND AUTOIMMUNE DISEASES

(71) Applicant: BRISTOL-MYERS SQUIBB COMPANY, Princeton, NJ (US)

(72) Inventors: Bingwei Vera Yang, Belle Mead, NJ (US); Gregory D. Brown, Lansdale, PA (US); Arun Kumar Gupta, Karnataka (IN); William J. Pitts, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/426,625

(22) PCT Filed: Sep. 5, 2013

(86) PCT No.: PCT/US2013/058114
§ 371 (c)(1),
(2) Date: Mar. 6, 2015

(87) PCT Pub. No.: WO2014/039595

PCT Pub. Date: Mar. 13, 2014

(65) Prior Publication Data

US 2015/0210703 A1 Jul. 30, 2015

Related U.S. Application Data

(60) Provisional application No. 61/781,074, filed on Mar. 14, 2013, provisional application No. 61/697,335, filed on Sep. 6, 2012.

(51) Int. Cl.
*C07D 487/04* (2006.01)
*C07B 59/00* (2006.01)

(52) U.S. Cl.
CPC ........... *C07D 487/04* (2013.01); *C07B 59/002* (2013.01); *C07B 2200/05* (2013.01)

(58) Field of Classification Search
CPC .................. C07D 487/04; C07B 2200/05
See application file for complete search history.

(56) References Cited

U.S. PATENT DOCUMENTS

2007/0078136 A1   4/2007   Vaccaro et al.

FOREIGN PATENT DOCUMENTS

| WO | WO 2004/099204 | 11/2004 |
| WO | WO 2011/014817 | 2/2011 |
| WO | 2011/014817 | * 3/2011 |
| WO | WO 2011/058109 | 5/2011 |
| WO | WO 2012/125886 | 9/2012 |
| WO | WO 2012/125887 | 9/2012 |
| WO | WO 2012/125893 | 9/2012 |

OTHER PUBLICATIONS

Coombs, J.H. et al., "Improved pain, physical functioning and health status in patients with rheumatoid arthritis treated with CP-690,550, an orally active Janus kinase (JAK) inhibitor: results from a randomised, double-blind, placebo-controlled trial", Ann. Rheum. Dis., vol. 69, pp. 413-416 (2010).

Ghoreschi, K. et al., "Modulation of Innate and Adaptive Immune Responses by Tofacitinib (CP-690,550)", The Journal of Immunology, vol. 186, pp. 4234-4243 (2011).

Milici, A.J. et al., "Cartilage preservation by inhibition of Janus kinase 3 in two rodent models of rheumatoid arthritis", Arthritis Research & Therapy, 10:R14 (2008) (doi:10.1186/ar2365).

O'Shea, J.J. et al., "A New Modality for Immunosuppression: Targeting the JAK/STAT Pathway", Nature Reviews: Drug Discovery, vol. 3, pp. 555-564 (2004).

Pesu, M. et al., "Jak3, severe combined immunodeficiency, and a new class of immunosuppressive drugs", Immunological Reviews, vol. 203, pp. 127-142 (2005).

Shi, M. et al., "Janus-Kinase-3-Dependent Signals Induce Chromatin Remodeling at the *Ifng* Locus During T Helper 1 Cell Differentiation", Immunity, vol. 28, pp. 763-773 (2008).

* cited by examiner

Primary Examiner — Paul V Ward
(74) Attorney, Agent, or Firm — Mary VanAtten

(57) ABSTRACT

The present invention provides compounds of formula (I) and pharmaceutically acceptable salts thereof. The formula I compounds inhibit tyrosine kinase activity of JAK3, thereby making them useful for the treatment of inflammatory and autoimmune diseases.

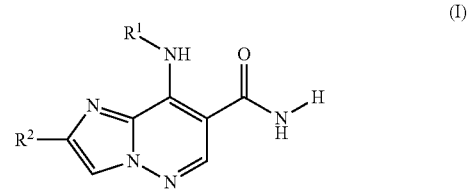

13 Claims, No Drawings

IMIDAZOPYRIDAZINE JAK3 INHIBITORS AND THEIR USE FOR THE TREATMENT OF INFLAMMATORY AND AUTOIMMUNE DISEASES

CROSS REFERENCE TO RELATED APPLICATIONS

This application is a national phase application under 35 U.S.C. §371 of International Patent Application No. PCT/US2013/058114, filed Sep. 5, 2013, which claims priority to U.S. Provisional Application 61/781,074, filed Mar. 14, 2013 and U.S. Provisional Application 61/697,335, filed Sep. 6, 2012.

FIELD OF THE INVENTION

This invention relates to novel pyrrolopyridazine compounds that are useful as inhibitors of Janus kinases (JAKs), more particularly JAK3. This invention also relates to a method of using the compounds in the treatment of inflammatory and autoimmune diseases, and to pharmaceutical compositions containing the compounds.

BACKGROUND OF THE INVENTION

The present invention relates to pyrrolopyridazine compounds, the methods of preparation of these compounds, and their use in the treatment of conditions in which selective modulation of the JAK signaling pathway via inhibition of the Janus kinases (JAKs) kinases, particularly the JAK3 kinase, may be therapeutically beneficial.

The Janus kinases (JAKs) belong to the non-receptor protein tyrosine kinase family and are known to be critical intracellular regulators of cytokine signaling via modulation of the JAK-STAT pathway (see, Murray, P. J., *Immunity*, 28:763 (2008)). There are four known mammalian JAK isoforms which include JAK1, JAK2, JAK3 and TYK2.

JAK3 has been shown to play a specific role in the signaling of a subset of cytokines known as the gamma common chain cytokine family which includes the interleukins IL-2, IL-4, IL-7, IL-9, IL-15, and IL-21. Deficiency of JAK3 in rodents and humans results in a severe combined immunodeficient (SCID) phenotype (see, Pesu, M. et al., *Immunol. Rev.*, 203:127 (2005)). Furthermore, JAK3 is known to have limited expression in hematopoeitic cells whereas JAK1, JAK2 and TYK2 have been shown to be more ubiquitously expressed. As a result of its specific role in regulating the immune response and its localized expression in lymphoid cells, inhibition of JAK3 has been recognized as a promising strategy for the development of novel and selective immunosuppressive agents that may be useful for transplant rejection prevention and in the treatment of autoimmune and inflammatory diseases such as psoriasis, rheumatoid arthritis, psoriatic arthritis, multiple sclerosis, inflammatory bowel disease, and lupus (see, O'Shea, J. J. et al., *Nat. Rev. Drug Discov.*, 3(7):555 (2004)). Moreover, the JAK inhibitor, CP-690,550 which potently inhibits JAK3, has been reported to be effective in the treatment of arthritis in rodent models as well as in patients with rheumatoid arthritis (see, Milici, A. J. et al., *Arthritis Res. & Therapy*, R14 (2008) and Coombs, J. H. et al., *Ann. Rheum. Dis.*, 69:413 (2010)). It has been suggested that the clinical efficacy of CP-690,550 (Tofacitinib) may be related to its ability to inhibit other JAK family members (see Ghoreschi, K. et al., *J. Immunol.*, 186:4234 (2011)). While JAK3 and JAK1 are both capable of modulating gamma common chain induce phosphorylation of STAT signalling, JAK1 inhibition can also decrease non-gamma common chain cytokine signalling (e.g., IL-6 signalling). Accordingly, novel compounds which inhibit the JAK/STAT pathway, more particularly via selective inhibition of JAK3 and/or JAK1, may be therapeutically useful. Certain inhibitors of JAK3 have been disclosed in applications filed by the present applicant via the Patent Cooperation Treaty under Nos. PCT/US2012/029334, PCT/US2012/029366 and PCT/US2012/029337.

It should be noted that the closely related isoform JAK2, is classically associated with interferon-γ production through the IL-12 pathway, but it also mediates the signaling of important hematopoietic growth factors such as erythropoietin (EPO), thromobopoetin (TPO) and granulocyte macrophage-stimulating factor (GM-CSF). As a result, the inhibition of JAK2 may result in adverse hematopoietic effects such as anemia, thrombocytopenia and generalized leukopenia.

Therefore, novel compounds which selectively inhibit JAK3 and/or JAK1 over JAK2 may be especially desirable in the safe treatment of chronic inflammatory and autoimmune diseases.

DETAILED DESCRIPTION OF THE INVENTION

The present invention provides for compounds of formula I, pharmaceutical compositions employing such compounds and for methods of using such compounds.

In accordance with the present invention, there are disclosed compounds of formula I

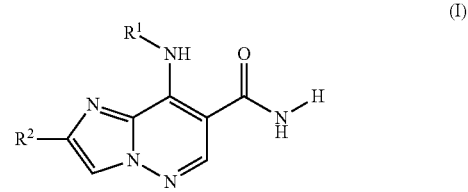

or a stereoisomer or pharmaceutically acceptable salt thereof, wherein:

$R^1$ is a 4- to 10-membered saturated or partially saturated heterocycle containing one heteroatom selected from O and $NR^{1b}$ substituted with 0-5 $R^{1a}$;

$R^{1a}$ is selected independently at each occurrence from hydrogen, =O, F, Cl, Br, $OCF_3$, $CF_3$, CN, $NO_2$, $-(CH_2)_rOR^b$, $-(CH_2)_rSR^b$, $-(CH_2)_rC(O)R^{1d}$, $-(CH_2)_rC(O)OR^b$, $-(CH_2)_rOC(O)R^b$, $-(CH_2)_rNR^cR^c$, $-(CH_2)_rC(O)NR^cR^c$, $-(CH_2)_rNR^bC(O)R^{1c}$, $-(CH_2)_rNR^bC(O)OR^c$, $-(CH_2)_rNR^bC(O)NR^cR^c$, $-(CH_2)_rS(O)_2NR^cR^c$, $-(CH_2)_rNR^bS(O)_2R^c$, $-(CH_2)_rS(O)R^e$, $-(CH_2)_rS(O)_2R^e$, $C_{1-6}$ alkyl substituted with 0-2 $R^a$, $C_{1-6}$ haloalkyl, $-(CH_2)_r$-3-14 membered carbocycle substituted with 0-2 $R^a$, or $-(CH_2)_r$-5-7 membered heterocycle comprising carbon atoms and 1-4 heteroatoms selected from N, O, and $S(O)_p$ substituted with 0-2 $R^a$;

$R^{1b}$ is hydrogen, $CF_3$, $-(CH_2)_rOR^b$, $-(CH_2)_rSR^b$, $-(CH_2)_rC(O)R^{1d}$, $-(CH_2)_rC(O)OR^b$, $-(CH_2)_rOC(O)R^b$, $-(CH_2)_rNR^cR^c$, $-(CH_2)_rC(O)NR^cR^c$, $-(CH_2)_rNR^bC(O)R^{1c}$, $-(CH_2)_rNR^bC(O)OR^c$, $-(CH_2)_rNR^bC(O)NR^cR^c$, $-(CH_2)_rS(O)_2NR^cR^c$, $-S(O)_2NR^cR^c$, $-(CH_2)_rNR^bS(O)_2R^e$, $-(CH_2)_rS(O)R^e$, $-(CH_2)_rS(O)_2R^e$, $C_{1-6}$ alkyl substituted with 0-2 $R^a$, $C_{1-6}$ haloalkyl, $-(CH_2)_r$-3-14 membered carbocycle substituted with 0-1 $R^a$, $-(CH_2)_r$-5-7 membered heterocycle comprising carbon atoms and 1-4 heteroatoms selected from N, O, and $S(O)_p$ substituted with 0-2 $R^a$; or a —$(CH_2)_r$-5-7 membered heteroaryl comprising carbon atoms and 1-4 heteroatoms selected from N, O, and S substituted with 0-2 $R^a$;

$R^{1c}$ is independently at each occurrence hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, a 5- to 10-membered heterocycle containing 1-4 heteroatoms selected from N, O, and S substituted with 0-3 $R^a$, a 5- to 10-membered heteroaryl containing 1-4 heteroatoms selected from N, O, and S substituted with 0-3 $R^a$;

$R^{1d}$ is independently at each occurrence hydrogen, $C_{1-6}$ alkyl substituted with 0-2 $R^d$, $C_{1-6}$ haloalkyl, $C(O)NR^cR^c$, $C_{3-6}$ cycloalkyl substituted with 0-2 $R^d$, or $(CH_2)_r$-phenyl substituted with 0-2 $R^a$, a 4- to 10-membered heterocycle containing 1-4 heteroatoms selected from N, O, and S substituted with 0-3 $R^a$;

$R^2$ is —$NR^bC(O)NR^cR^c$, —$NR^bC(O)R^{2b}$, —$NR^bC(O)OR^{2d}$, —$NR^bS(O)_2R^{2b}$, —$(CH_2)_r$—$C_{6-10}$ aryl substituted with 0-3 $R^{2a}$, a —$(CH_2)_r$-5-7 membered heterocycle comprising carbon atoms and 1-4 heteroatoms selected from N, O, and $S(O)_p$ substituted with 0-3 $R^a$ or a —$(CH_2)_r$-4-10 membered heteroaryl containing 1-4 heteroatoms selected from N, O, and S substituted with 0-3 $R^{2a}$;

$R^{2a}$ is selected independently at each occurrence from =O, F, Cl, Br, $OCF_3$, $CF_3$, CN, $CD_3$, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^cR^c$, —$(CH_2)_rC(O)NR^cR^c$, —$(CH_2)_rNR^bC(O)R^{2b}$, —$(CH_2)_rNR^bC(O)OR^c$, —$NR^bC(O)NR^cR^c$, —$S(O)_2NR^cR^c$, —$NR^bS(O)_2R^c$, —$S(O)R^e$, —$S(O)_2R^e$, $(CH_2)_rNH(C=NCN)NHR^{11}$, $C_{1-6}$ alkyl substituted with 0-2 $R^a$, $C_{2-6}$ alkenyl, $C_{1-6}$ haloalkyl, —$(CH_2)_r$-3-14 membered carbocycle substituted with 0-1 $R^a$, and —$(CH_2)_r$-5-10 membered heterocycle comprising carbon atoms and 1-4 heteroatoms selected from N, O, and $S(O)_p$ substituted with 0-1 $R^a$;

$R^{2b}$ is independently at each occurrence hydrogen, $C_{1-6}$ alkyl substituted with 0-2 $R^a$, $C_{1-6}$ haloalkyl, $C_{3-6}$ cycloalkyl substituted with 0-2 $R^a$, or $(CH_2)_r$-phenyl substituted with 0-2 $R^a$, or —$(CH_2)_r$-5-10 membered heterocycle comprising carbon atoms and 1-4 heteroatoms selected from N, O, and $S(O)_p$ substituted with 0-1 $R^a$;

$R^{2d}$ is independently at each occurrence $C_{1-6}$ alkyl substituted with 0-2 $R^a$, $C_{1-6}$ haloalkyl, $C_{3-6}$ cycloalkyl substituted with 0-2 $R^a$, or $(CH_2)_r$-phenyl substituted with 0-2 $R^a$, or —$(CH_2)_r$-5-10 membered heterocycle comprising carbon atoms and 1-4 heteroatoms selected from N, O, and $S(O)_p$ substituted with 0-1 $R^a$;

$R^3$ is hydrogen, $C_{1-6}$ alkyl substituted with 0-1 $R^a$, phenyl substituted with 0-1 $R^a$, or $C_{3-6}$ cycloalkyl substituted with 0-1 $R^a$;

$R^a$ is independently at each occurrence hydrogen, =O, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^cR^c$, —$(CH_2)_rC(O)NR^cR^c$, —$(CH_2)_rNR^bC(O)R^c$, —$(CH_2)_rNR^bC(O)OR^c$, —$NR^bC(O)NR^cR^c$, —$S(O)_2NR^cR^c$, —$NR^bS(O)_2R^c$, —$S(O)R^e$, —$S(O)_2R^e$, $(CH_2)_rNH(C=NCN)NHR^c$, $C_{1-6}$ alkyl substituted with 0-1 $R^f$, $C_{1-6}$ haloalkyl, —$(CH_2)_r$-3-14 membered carbocycle substituted with 0-1 $R^d$, or —$(CH_2)_r$-5-7 membered heterocycle comprising carbon atoms and 1-4 heteroatoms selected from N, O, and $S(O)_p$ substituted with 0-1 $R^d$, alternatively two $R^a$ on adjacent or the same carbon atom form a cyclic acetal of the formula —O—$(CH_2)_n$—O—, or —O—$CF_2$—O—, wherein n is selected from 1 or 2;

$R^b$ is independently at each occurrence hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$, or —$(CH_2)_r$-5-7 membered heterocycle comprising carbon atoms and 1-4 heteroatoms selected from N, O, and $S(O)_p$ substituted with 0-1 $R^d$;

$R^c$ is independently at each occurrence hydrogen, $C_{1-6}$ alkyl substituted with 0-1 $R^f$, $C_{3-6}$ cycloalkyl, or $(CH_2)_r$-phenyl substituted with 0-1 $R^f$;

$R^d$ is independently at each occurrence hydrogen, F, Cl, Br, $OCF_3$, $CF_3$, CN, $NO_2$, —$OR^c$, —$(CH_2)_rC(O)R^c$, —$NR^cR^c$, —$NR^cC(O)OR^c$, —$C(O)OR^c$, —$SO_2N(R^c)_2$, $C_{1-6}$ alkyl, or $(CH_2)_r$-phenyl;

$R^e$ is independently at each occurrence $C_{1-6}$ alkyl, $C_{3-6}$ cycloalkyl, or $(CH_2)_r$-phenyl;

$R^f$ is independently at each occurrence hydrogen, halo, CN, $SO_2$-methyl, phenyl, $NH_2$, NHCO-methyl, OH or $OCH_3$;

r is 0, 1, 2, 3, or 4; and p is 0, 1, or 2.

In another embodiment, there are provided compounds of formula (I), or a stereoisomer or pharmaceutically acceptable salt thereof, wherein $R^3$ is hydrogen.

In another embodiment, there are provided compounds of formula (I), or a stereoisomer or pharmaceutically acceptable salt thereof, wherein:

$R^2$ is —$NR^bC(O)R^{2b}$, $C_{6-10}$ aryl substituted with 0-3 $R^{2a}$, or 5- to 10-membered heteroaryl containing 1-4 heteroatoms selected from N, O, and S substituted with 0-3 $R^{2a}$;

$R^{2a}$ is independently at each occurrence =O, F, Cl, Br, $CF_3$, CN, —$(CH_2)_rOR^b$, —$(CH_2)_rC(O)R^b$, —$(CH_2)_rC(O)OR^b$, —$(CH_2)_rNR^cR^c$, —$(CH_2)_rC(O)NR^cR^c$, —$(CH_2)_rNR^bC(O)R^{2b}$, —$S(O)_2R^e$, $C_{1-6}$ alkyl substituted with 0-2 $R^a$, —$(CH_2)_r$-3-14 membered carbocycle substituted with 0-1 $R^a$, or —$(CH_2)_r$-5-10 membered heterocycle comprising carbon atoms and 1-4 heteroatoms selected from N, O, and $S(O)_p$ substituted with 0-1 $R^a$;

$R^{2b}$ is independently at each occurrence $C_{1-6}$ alkyl substituted with 0-2 $R^a$ or $C_{1-6}$ haloalkyl; and r is 0, 1, or 2.

In another embodiment, there are provided compounds of formula (I)

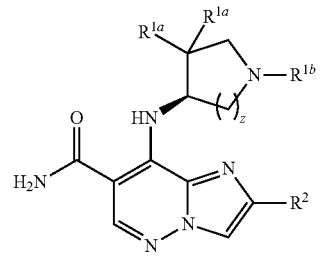

or a stereoisomer or pharmaceutically acceptable salt thereof, wherein:

$R^{1a}$ is independently at each occurrence H, F, Cl, Br, —$(CH_2)_rOR^b$, $C_{1-6}$ alkyl substituted with 0-2 $R^a$, —$(CH_2)_r$-3-6 membered carbocycle substituted with 0-2 $R^a$;

$R^{1b}$ is hydrogen, —$(CH_2)_rC(O)R^{1d}$, —$(CH_2)_rC(O)OR^b$, —$(CH_2)_rS(O)_2R^e$, $C_{1-6}$ alkyl substituted with 0-2 $R^a$, a —$(CH_2)_r$-5-7 membered heterocycle comprising carbon atoms and 1-4 heteroatoms selected from N, O, and $S(O)_p$ substituted with 0-2 $R^a$; or a —$(CH_2)_r$-5-7 membered heteroaryl comprising carbon atoms and 1-4 heteroatoms selected from N, O, and S substituted with 0-2 $R^a$;

$R^{1d}$ is independently at each occurrence hydrogen, $C_{1-6}$ alkyl substituted with 0-2 $R^d$, $C_{1-6}$ haloalkyl, C(O)NR$^c$R$^c$, $C_{3-6}$ cycloalkyl substituted with 0-2 $R^d$, or $(CH_2)_r$-phenyl substituted with 0-2 $R^a$, a 4- to 10-membered heterocycle containing 1-4 heteroatoms selected from N, O, and S substituted with 0-3 $R^a$;

$R^2$ is —NR$^b$C(O)R$^{2b}$, $C_{6-10}$ aryl substituted with 0-3 $R^{2a}$, a —(CH$_2$)$_r$-5-7 membered heterocycle comprising carbon atoms and 1-4 heteroatoms selected from N, O, and S(O)$_p$ substituted with 0-3 $R^a$ or 5- to 10-membered heteroaryl containing 1-4 heteroatoms selected from N, O, and S substituted with 0-3 $R^{2a}$;

$R^{2a}$ is independently at each occurrence =O, F, Cl, Br, CF$_3$, CD$_3$, CN, —(CH$_2$)$_r$OR$^b$, —(CH$_2$)$_r$C(O)R$^b$, —(CH$_2$)$_r$C(O)OR$^b$, —(CH$_2$)$_r$NR$^c$R$^c$, —(CH$_2$)$_r$C(O)NR$^c$R$^c$, —(CH$_2$)$_r$NR$^b$C(O)R$^{2b}$, —S(O)$_2$R$^e$, $C_{1-6}$ alkyl substituted with 0-2 $R^a$, —(CH$_2$)$_r$-3-14 membered carbocycle substituted with 0-1 $R^a$, or —(CH$_2$)$_r$-5-10 membered heterocycle comprising carbon atoms and 1-4 heteroatoms selected from N, O, and S(O)$_p$ substituted with 0-1 $R^a$;

$R^{2b}$ is independently at each occurrence $C_{1-6}$ alkyl substituted with 0-2 $R^a$ or $C_{1-6}$ haloalkyl;

$R^a$ is independently at each occurrence hydrogen, F, Cl, Br, CF$_3$, CN, —(CH$_2$)$_r$OR$^b$, —(CH$_2$)$_r$NR$^c$R$^c$, $C_{1-6}$ alkyl substituted with 0-1 $R^f$, or $C_{1-6}$ haloalkyl;

$R^b$ is independently at each occurrence hydrogen, $C_{1-6}$ alkyl substituted with 0-2 $R^d$, $C_{3-6}$ cycloalkyl substituted with 0-2 $R^d$, or —(CH$_2$)$_r$-5-7 membered heterocycle comprising carbon atoms and 1-4 heteroatoms selected from N, O, and S(O)$_p$ substituted with 0-1 $R^d$;

$R^c$ is independently at each occurrence hydrogen or $C_{1-6}$ alkyl;

$R^d$ is independently at each occurrence hydrogen, F, Cl, Br, CF$_3$, CN, —OR$^c$, or $C_{1-6}$ alkyl;

$R^e$ is independently at each occurrence $C_{1-6}$ alkyl;

$R^f$ is independently at each occurrence hydrogen, halo, CN, SO$_2$-methyl, phenyl, NH$_2$, NHCO-methyl, OH or OCH$_3$;

r is 0, 1, 2, 3, or 4;

p is 0, 1, or 2; and z is 1 or 2.

In another embodiment, there are provided compounds of formula (I), or a stereoisomer or pharmaceutically acceptable salt thereof, wherein:

$R^2$ is selected from NR$^b$C(O)R$^{2b}$ and a group selected from phenyl, pyridyl, indazolyl, indolyl, morpholinyl, pyridinyl, quinolinyl, pyrrolidinonyl, pyrazolyl, pyrimidinyl, imidazolidinonyl, pyradizinyl, oxadiazolyl, tetrazolyl, dihydrobenzooxazinyl, pyridinonyl, oxadiazolyl, triazolyl and oxazolyl, each group substituted with 0-3 $R^{2a}$; and $R^{2a}$ is
i) $C_{1-6}$ alkyl or $C_{3-6}$ cycloalkyl, each group substituted with 0-2 $R^d$; or
ii) =O, OR$^b$, cyano, CF$_3$, (CH$_2$)$_r$C(O)R$^b$, C(O)$_2$R$^b$, fluoro, (CH$_2$)$_r$C(O)N(R$^c$)(R$^c$), phenyl, =O, N(R$^c$)(R$^c$), morpholinyl, S(O)$_2$R$^e$, CD$_3$, or CH$_2$NR$^b$C(O)R$^{2b}$.

In another embodiment, there are provided compounds of formula (I), or a stereoisomer or pharmaceutically acceptable salt thereof, wherein R$^1$ is

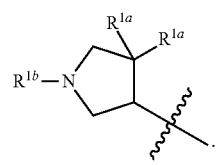

In another embodiment, there are provided compounds of formula (I), wherein R$^1$ is

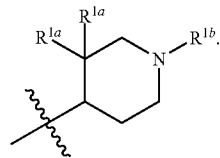

In another embodiment, there are provided compounds of formula (I), or a stereoisomer or pharmaceutically acceptable salt thereof, wherein $R^{1a}$ is independently at each occurrence H or $C_{1-6}$ alkyl substituted with 0-2 $R^a$;

$R^{1b}$ is
i) hydrogen, —(CH$_2$)$_r$C(O)R$^{1d}$, —(CH$_2$)$_r$C(O)OR$^b$, or —(CH$_2$)$_r$S(O)$_2$R$^e$;
ii) or $C_{1-6}$ alkyl, pyridyl, or pyridazinyl, each group substituted with 0-2 $R^a$;

$R^{1d}$ is independently at each occurrence:
i) hydrogen, $C_{1-6}$ haloalkyl, or C(O)NR$^c$R$^c$;
ii) $C_{1-6}$ alkyl, cyclopropyl, cyclobutyl or oxetane, each group substituted with 0-2 $R^d$;
iii) or (CH$_2$)$_r$-phenyl substituted with 0-2 $R^a$;

$R^2$ is -phenyl, pyridyl, indazolyl, indolyl, morpholinyl, pyridinyl, quinolinyl, pyrrolidinonyl, pyrazolyl, pyrimidinyl, imidazolidinonyl, pyradizinyl, oxadiazolyl, tetrazolyl, dihydrobenzooxazinyl, pyridinonyl, oxadiazolyl, triazolyl and oxazolyl, each group substituted with 0-3 $R^{2a}$;

$R^{2a}$ is =O, OR$^b$, cyano, CF$_3$, CHF$_2$, (CH$_2$)$_r$C(O)R$^b$, C(O)$_2$R$^b$, fluoro, methyl, (CH$_2$)$_r$C(O)NR$^c$R$^c$, methyl, isopropyl, propyl, ethyl, isobutyl, cyclopropyl, (CH$_2$)$_2$R$^a$, phenyl, =O, NR$^c$R$^c$, CH(R$^a$)$_2$, morpholinyl, C(CH$_3$)$_2$R$^a$, S(O)$_2$R$^e$, CD$_3$, CH$_2$CH(R$^a$)(R$^a$), CH$_2$C(CH$_3$)$_2$R$^a$, CH$_2$CH(R$^a$)CH$_3$, CH$_2$CH(R$^a$)CH$_2$(R$^a$), CH(R$^a$)$_2$, CH$_2$NR$^b$C(O)R$^{2b}$ or (CH$_2$)$_2$R$^a$;

$R^{2b}$ is independently at each occurrence $C_{1-6}$ alkyl substituted with 0-2 $R^a$ or $C_{1-6}$ haloalkyl;

$R^a$ is independently at each occurrence hydrogen, F, Cl, Br, CF$_3$, CN, —(CH$_2$)$_r$OR$^b$, —(CH$_2$)$_r$NR$^c$R$^c$, $C_{1-6}$ alkyl substituted with 0-1 $R^f$ or $C_{1-6}$ haloalkyl;

$R^b$ is independently at each occurrence hydrogen, $C_{1-6}$ alkyl substituted with 0-2 $R^d$, $C_{3-6}$ cycloalkyl substituted with 0-2 $R^d$, or —(CH$_2$)$_r$-5-7 membered heterocycle comprising carbon atoms and 1-4 heteroatoms selected from N, O, and S(O)$_p$ substituted with 0-1 $R^d$;

$R^c$ is independently at each occurrence hydrogen or $C_{1-6}$ alkyl; $R^d$ is independently at each occurrence hydrogen, F, Cl, Br, CF$_3$, CN, —OR$^c$, or $C_{1-6}$ alkyl;

$R^e$ is independently at each occurrence $C_{1-6}$ alkyl;

r is independently at each occurrence 0, 1, 2, 3, or 4; and p is independently at each occurrence 0, 1, or 2.

In another embodiment, or a stereoisomer or pharmaceutically acceptable salt thereof, there are provided compounds of formula (I) wherein $R^{1a}$ is independently at each occurrence H or $C_{1-6}$ alkyl substituted with 0-2 $R^a$;

$R^{1b}$ is —C(O)R$^{1d}$, pyridyl, or pyridazinyl, each group substituted with 0-2 $R^a$;

$R^{1d}$ is independently at each occurrence: cyclopropyl, cyclobutyl or oxetane, each group substituted with 0-2 $R^d$;

$R^2$ is pyridyl, indazolyl, indolyl, quinolinyl, or pyrazolyl, each group substituted with 0-3 $R^{2a}$;

$R^{2a}$ is =O, $CHF_2$, methyl, isopropyl, ethyl, cyclopropyl, $CH_2C(CH_3)_2R^a$, $CH_2CH(R^a)CH_3$, or $CH_2CH(R^a)CH_2(R^a)$;

$R^a$ is independently at each occurrence hydrogen, F, $CF_3$, CN or $-(CH_2)_rOR^b$;

$R^b$ is independently at each occurrence hydrogen or $C_{1-6}$ alkyl substituted with 0-2 $R^d$; and $R^d$ is CN.

In another embodiment, there are provided compounds of formula (I), or a stereoisomer or pharmaceutically acceptable salt thereof, wherein $R^2$ is selected from:

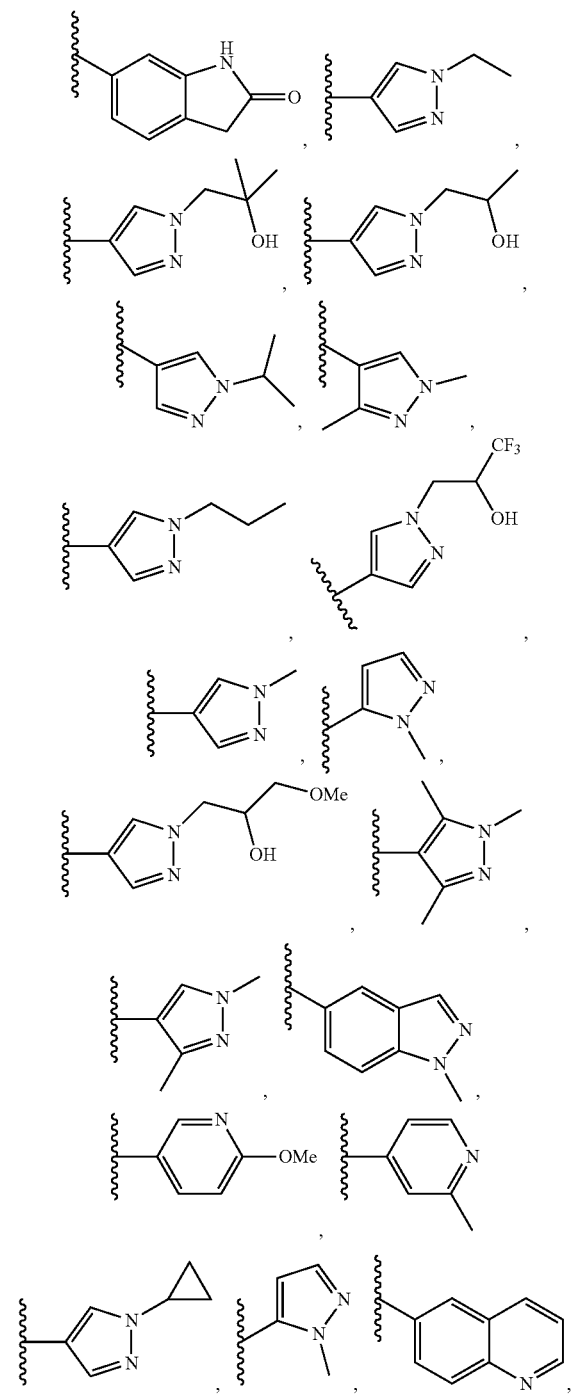

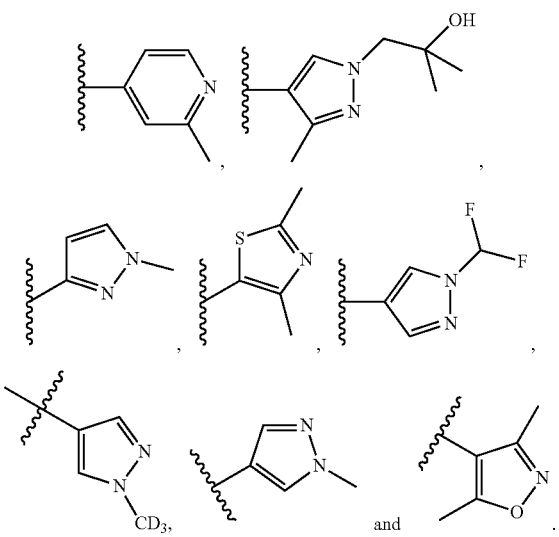

and

In another embodiment, there are provided compounds of formula (I), or a stereoisomer or pharmaceutically acceptable salt thereof, wherein the compound is of formula III

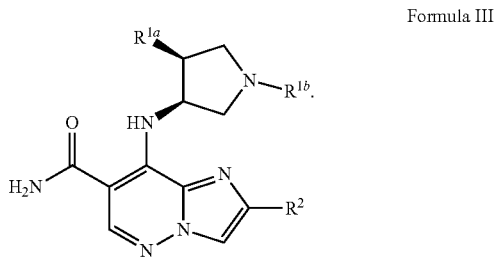

Formula III

In another embodiment, there are provided compounds of formula (I), or a stereoisomer or pharmaceutically acceptable salt thereof, wherein $R^{1a}$ is independently at each occurrence H or $C_{1-3}$ alkyl substituted with 0-2 $R^a$;

$R^{1b}$ is $-C(O)R^{1d}$;

$R^{1d}$ is independently at each occurrence cyclopropyl, cyclobutyl or oxetane, each group substituted with 0-2 $R^d$; and $R^2$ is pyridyl, indazolyl, indolyl, quinolinyl or pyrazolyl, each group substituted with 0-3 $R^{2a}$.

In another embodiment of the present invention, wherein $R^{1a}$ is $C_2D_5$ and $R^{1b}$ is 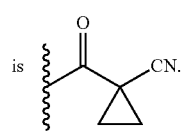

In another embodiment, there are provided compounds of formula (I), or a stereoisomer or pharmaceutically acceptable salt thereof, wherein the compound is of formula IV Formula IV

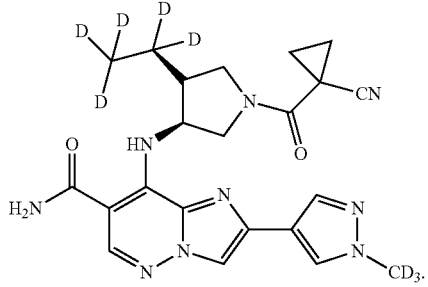

In another embodiment are compounds of Formula (I), wherein the compound of formula (I) is selected from the Examples herein, or a pharmaceutically-acceptable salt thereof.

In another embodiment the present invention provides a pharmaceutical composition comprising a pharmaceutically acceptable carrier and at least one of the compounds of the present invention, or a stereoisomer or pharmaceutically acceptable salt thereof.

In another embodiment, the present invention provides a pharmaceutical composition comprising a compound of formula I, or pharmaceutically acceptable salt thereof, and a pharmaceutically acceptable carrier or diluent.

In another embodiment, the present invention provides a pharmaceutical composition, comprising: a pharmaceutically acceptable carrier and a therapeutically effective amount of at least one of the compounds of the present invention, or a stereoisomer or pharmaceutically acceptable salt thereof.

In another embodiment, the present invention provides a method for treating inflammatory or autoimmune disease: administering to a patient in need of such treatment a therapeutically effective amount of at least one of the compounds of the present invention, or a stereoisomer or a pharmaceutically acceptable salt thereof, in combination with at least one other therapeutic agent, or a stereoisomer or a pharmaceutically acceptable salt thereof.

In another embodiment, the present invention provides a method for treating inflammatory and/or autoimmune diseases comprising: administering to a patient in need of such treatment a therapeutically effective amount of at least one of the compounds of the present invention, or a stereoisomer or a pharmaceutically acceptable salt thereof.

In another embodiment, the present invention provides a method of treating a patient in need of inflammatory and/or autoimmune diseases treatment, comprising: administering a compound of the present invention, or a stereoisomer or a pharmaceutically acceptable salt thereof, in an amount effective to treat the inflammatory and/or autoimmune diseases.

In another embodiment, the present invention provides a method of treating inflammatory or autoimmune diseases, wherein the inflammatory or autoimmune diseases is selected from Crohn's, ulcerative colitis, asthma, Graves' disease, rheumatoid arthritis, systemic lupus erythematosus, psoriasis, dry eye, multiple sclerosis, psoriatic arthritis and ankylosing spondylitis, solid organ transplant rejection, islet cell transplant rejection and graft vs. host disease.

In another embodiment, the present invention provides a novel method, comprising: administering a compound of the present invention or a stereoisomer or a pharmaceutically acceptable salt, thereof in an amount effective to treat an inflammatory and/or autoimmune diseases.

In another embodiment, the present invention provides a method for treating inflammatory and/or autoimmune diseases comprising: administering to a patient in need of such treatment a therapeutically effective amount of a compound of formula (I) or a stereoisomer or a pharmaceutically acceptable salt thereof, in combination with at least one other anti-cancer agent or antiproliferative agent and/or another agent, or a stereoisomer or a pharmaceutically acceptable salt thereof.

In another embodiment, the present invention provides a method for treating inflammatory and/or autoimmune diseases comprising: administering to a patient in need of such treatment a therapeutically effective amount of at least one of the compounds of the present invention or a stereoisomer or a pharmaceutically acceptable salt, thereof, in combination with at least one other therapeutic agent, or a stereoisomer or a pharmaceutically acceptable salt thereof.

In another embodiment, the present invention provides a compound of the present invention for use in therapy.

In another embodiment, the present invention provides a compound of the present invention for use in therapy for treating an inflammatory and/or autoimmune disease.

In another embodiment, the present invention also provides the use of a compound of formula I of the present invention for the manufacture of a medicament for the treatment of an inflammatory and/or autoimmune disease.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

DEFINITIONS

The following are definitions of terms that may be used in the present specification. The initial definition provided for a group or term herein applies to that group or term throughout the present specification individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "substituted", as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and are intended to the include the deuterated groups, such as $CD_3$ and $CD_2CD_3$, and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo.

The term "cycloalkyl" refers to cyclized alkyl groups, including mono-, bi- or poly-cyclic ring systems. $C_{3-10}$ cycloalkyl is intended to include $C_3$, $C_4$, $C_5$, $C_6$, $C_7$, $C_8$, $C_9$, and $C_{10}$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3-, 4-, 5-, 6-, or 7-membered monocyclic or bicyclic or 7-, 8-, 9-, or 10-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkylsulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4- to 7-membered monocyclic, 7- to 11-membered bicyclic, or 10- to 15-membered tricyclic ring system, which has at least one heteroatom and at least one carbon atom-containing ring, for example, pyridine, tetrazole, indazole.

As used herein, the term "heterocycle", "heterocyclyl", "heterocyclic system" or "heterocyclic group" is intended to mean a stable 5-, 6-, or 7-membered monocyclic or bicyclic or 7-, 8-, 9-, 10-, 11-, 12-, 13-, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

In another embodiment, heterocycles include, but are not limited to, pyridyl, pyridinyl, isoxazyl, isoquinolinyl, thienyl, pyrazolyl, furanyl, pyrrolyl, thiazolyl, imidazolyl, pyrazinyl, thiadiazolyl, pyrimidinyl, pyridazinyl, oxazolyl, isothiazolyl, oxadiazolyl, indanonyl, piperazinyl, pyranyl, or pyrrolyl.

Also included are smaller heterocyclyls, such as, epoxides, oxetanes and aziridines.

The term heterocyclo or heteroaryl includes substituents having a benzo ring or a cycloalkyl ring fused to another ring containing 1 to 4 heteroatoms selected from N, O, or S, including, but not limited to rings which contain —O—$(CH_2)_n$—O— attached to adjacent atoms or the same ring atom.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower] alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may exist as a free form (with no ionization) or may form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. The present invention is intended to cover all isotopes in their natural abundance, as well as artificially enhanced isotopes, such as the group $CD_3$ and $CD_2CD_3$, (deuterated methyl and deuterated ethyl).

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and c) Bundgaard, H., *Adv. Drug Deliv. Rev.*, 8:1-38 (1992).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group. The present invention is directed to stable compounds. Compounds of the invention are intended to cover compounds which are stable compounds.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination. "Therapeutically effective amount" is also intended to include an amount of the combination of compounds which is effective for the treatment of disease.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sci-* ences, 17th Edition, Mack Publishing Company, Easton, Pa. (1985), which is incorporated herein by reference in its entirety.

Utility

The compounds of the invention modulate kinase activity, including the modulation of JAK3. Other types of kinase activity that may be modulated by the compounds of the instant invention include, but are not limited to, other members of the JAK family of enzymes, such as JAK1.

Accordingly, compounds of formula (I) have utility in treating conditions associated with the modulation of kinase activity, and particularly the selective inhibition of JAK3 activity or the inhibition of other JAK family kinases such as JAK1. Such conditions include T-cell mediated diseases in which cytokine levels are modulated as a consequence of intracellular signaling. In another embodiment, compounds of formula (I) have advantageous functional selectivity for JAK3 activity versus other JAK family kinases such as JAK2, preferably from at least 10 fold to over 100 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of JAK3 and other JAK family kinases such as JAK1, compounds of Formula (I) are useful in treating cytokine-associated conditions including, but not limited to, autoimmune diseases such as Crohn's and ulcerative colitis, asthma, autoimmune diseases such as Graves' disease, rheumatoid arthritis, systemic lupus erythematosus, psoriasis, dry eye, multiple sclerosis, psoriatic arthritis and ankylosing spondylitis, plus conditions such as solid organ transplant rejection, islet cell transplant rejection and graft vs. host disease.

In view of their activity as inhibitors of JAK3, compounds of Formula (I) are useful in treating malignancies where JAK3 has undergone mutation or overexpression, or where JAK3 plays an important role in growth or survival of the malignant cells. Such malignancies include acute megakaryoblastic leukemia (AMKL), cutaneous T cell lymphoma (CTCL), anaplastic lymphoma kinase (ALK)-expressing anaplastic large cell lymphoma (ALK(+)ALCL), acute lymphoblastic leukemia (ALL) with JAK3 mutations, and cutaneous T-cell lymphoma (CTCL).

More particularly, the specific conditions or diseases that may be treated with the inventive compounds include, without limitation, asthma, allergies, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, myasthenia gravis, multiple sclerosis, inflammatory bowel disease, ulcerative colitis, Crohn's disease, psoriasis, graft vs. host disease, pancreatic β-cell disease; rheumatoid spondylitis, allograft rejections, ulcerative colitis, dry eye and pemphigus vulgaris. Preferred methods of treatment are those wherein the condition is selected from allograft rejection, rheumatoid arthritis, psoriasis, ankylosing spondylitis, psoriatic arthritis, multiple sclerosis, lupus and dry eye.

When the terms "JAK3-associated condition" or "JAK3-associated disease or disorder" are used herein, each is intended to encompass all of the conditions identified above as if repeated at length, as well as any other condition that is affected by JAK3 kinase activity.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit JAK3 and other JAK family kinases and/or treat diseases.

The methods of treating JAK3 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit JAK3 and/or treat diseases associated with JAK3.

Exemplary of such other therapeutic agents include abatacept, belatacept, corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; p38 inhibitors such as BMS-582949, steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating JAK3 kinase-associated conditions, including IL-2, IL-4, IL-6, IL-7, IL-9, IL-15, IL-21, and IFNγ mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of JAK3 enzyme levels.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to treat the cancer.

By way of general guidance, the daily oral dosage of each active ingredient, when used for the indicated effects, will range between about 0.001 to 1000 mg/kg of body weight, preferably between about 0.001 to 100 mg/kg of body weight per day, and most preferably between about 0.001 to 20 mg/kg/day. Intravenously, the most preferred doses will range from about 0.1 to about 10 mg/kg. Compounds of this invention may be administered in a single daily dose, or the total daily dosage may be administered in divided doses of two, three, or four times daily. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of JAK3 enzyme levels.

Biological Assays

JAK3 Kinase Assay Protocol (Caliper)

The assay reactions were performed in U-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM $MgCl_2$, 25 mM beta-glycerol phosphate 0.015% Brij35 and 4 mM DTT). The reaction was initiated by the combination of GST-JAK3 enzyme with substrates and test compounds. The reactions were incubated at room temperature for 3 hours and terminated by adding 60 µl of 35 mM EDTA to each sample. Each reaction mixture was analyzed on the Caliper LABCHIP® 3000 (Caliper, Hopkinton, Mass.) by electrophoretic separation of the fluorescent substrate and phosphorylated product Inhibition data were calculated by comparison with no enzyme control reactions for 100% inhibition, and vehicle-only treated reactions for 0% inhibition. The final concentration of reagents in the assay was: ATP, 8 µM; fluoresceinated peptide, 1.5 µM; GST-JAK3, 4.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

JAK3 Kinase Assay Protocol (Filter)

Kinase reactions consisted of 5 ng of JAK3 enzyme, 30 µM CSKtide substrate, 0.2 µCi $^{33}P$ γ-ATP, 8 µM ATP in 30 µl kinase buffer (50 mM Hepes, pH 8.0, 10 mM $MgCl_2$, 1 mM EGTA, 2 mM DTT). Reactions were incubated for 30 minutes at room temperature and stopped by the addition of cold trichloroacetic acid (TCA) to a final concentration of 15%. TCA precipitates were collected onto 384 well phosphocellulose filters (Millipore) using a PLATEMATE® to transfer the reaction mixture, washed on an EMBLA plate washer and the filters were quantitated using a TOP-COUNT® 384-well liquid scintillation counter. Dose response curves were generated to determine the concentration required inhibiting 50% of kinase activity ($IC_{50}$). Compounds were dissolved at 10 mM in dimethylsulfoxide (DMSO) and evaluated at six concentrations, each in triplicate. The final concentration of DMSO in the assay equaled 2%. $IC_{50}$ values were derived by non-linear regression analysis.

JAK2 Kinase Assay Protocol

The assay reactions were performed in U-bottom 384-well plates. The final assay volume was 30 µl prepared from 15 µl additions of enzyme and substrates (fluoresceinated peptide and ATP) and test compounds in assay buffer (100 mM HEPES pH 7.4, 10 mM $MgCl_2$, 25 mM beta-glycerol phosphate, 0.015% Brij35 and 4 mM DTT). The reaction was initiated by the combination of GST-JAK2 enzyme with substrates and test compounds. The reactions were incubated at room temperature for 3 hours and terminated by adding 60 µl of 35 mM EDTA to each sample. Each reaction mixture was analyzed on the Caliper LABCHIP® 3000 (Caliper, Hopkinton, Mass.) by electrophoretic separation of the fluorescent substrate and phosphorylated product Inhibition data were calculated by comparison with no enzyme control reactions for 100% inhibition, and vehicle-only treated reactions for 0% inhibition. The final concentration of reagents in the assay was: ATP, 30 µM; fluoresceinated peptide, 1.5 µM; GST-JAK2, 1.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

JAK1 Kinase Assay Protocol

The assay reactions were performed in U-bottom 384-well plates. The final assay volume was 30 µl prepared from 15 µl additions of enzyme and substrates (fluoresceinated peptide and ATP) and test compounds in assay buffer (20 mM HEPES pH 7.4, 10 mM $MgCl_2$, 25 mM beta-glycerol phosphate, 0.015% Brij35 and 4 mM DTT). The reaction was initiated by the combination of GST-JAK1 enzyme with substrates and test compounds. The reactions were incubated at room temperature for 3 hours and terminated by adding 60 µl of 35 mM EDTA to each sample. Each reaction mixture was analyzed on the Caliper LABCHIP® 3000 (Caliper, Hopkinton, Mass.) by electrophoretic separation of the fluorescent substrate and phosphorylated product Inhibition data were calculated by comparison with no enzyme control reactions for 100% inhibition, and vehicle-only treated reactions for 0% inhibition. The final concentration of reagents in the assays was: ATP, 100 µM; fluoresceinated peptide, 1.5 µM; GST-JAK1, 12.5 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

TYK2 Kinase Assay Protocol

The assay reactions were performed in U-bottom 384-well plates. The final assay volume was 30 µl prepared from 15 µl additions of enzyme and substrates (fluoresceinated peptide and ATP) and test compounds in assay buffer (20 mM HEPES pH 7.4, 10 mM $MgCl_2$, 25 mM beta-glycerol phosphate, 0.015% Brij35 and 4 mM DTT). The reaction was initiated by the combination of HIS-TYK2 enzyme with substrates and test compounds. The reactions were incubated at room temperature for 3 hours and terminated by adding 60 µl of 35 mM EDTA to each sample. Each reaction mixture was analyzed on the Caliper LABCHIP® 3000 (Caliper, Hopkinton, Mass.) by electrophoretic separation of the fluorescent substrate and phosphorylated product Inhibition data were calculated by comparison with no enzyme control reactions for 100% inhibition, and vehicle-only treated reactions for 0% inhibition. The final concentration of reagents in the assay was: ATP, 70 µM; fluoresceinated peptide, 1.5 µM; HIS-TYK2, 2.25 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

IL-2 Dependent T Cell Proliferation Assay Protocol

IL-2 expanded PHA blasts (activated T cells) were prepared from peripheral blood mononuclear cells (PBMC). PBMCs were prepared from human whole blood. 15 ml blood was mixed with 15 ml RPMI (Gibco #61870) in a 50 ml centrifuge tube and under laid with 12 ml lymphocyte separation media (LSM) (MC Biomedicals #1492254).

Tubes were centrifuged at 1800 rpm for 25 minutes and allowed to stop without braking Red blood cells pelleted under the separation media and the PBMCs were trapped at the interface between the LSM and the serum/RPMI layers. The serum/RPMI mix was pipetted from above the PBMC layer and discarded. The PBMCs from 2 tubes were collected in a pipette along with some of the LSM layer and combined into a single tube. Each tube was brought to 50 ml and centrifuged at 1400 rpm for 10 minutes. Cell pellets were resuspended in RPMI, combined into 1 tube and centrifuged for 5 minutes at 1200 rpm. Cells were resuspended in cell culture media (RPMI w/10% fetal bovine serum (Summit Biotechnology #RS-50-05), 100 U/ml penicillin and 100 μg/ml streptomycin (Gibco #14140-122)) with 5 μg/ml PHA (Sigma #L1668) at $2\times10^6$ cells/ml and incubated for 3 days at 37° C. in 5% $CO_2$. Cells were washed 3× and resuspended at $5\times10^5$ cells/ml and 25 units/ml IL-2 (BD Bioscience #356043) was added. After 4 days incubation at 37° C. in 5% $CO_2$ the cells were washed 3× and resuspended at $2\times10^6$ cells/ml and rested 2 hours at 37° C. in 5% $CO_2$ before use.

Compounds were diluted in DMSO (in triplicate) to 800× final high concentration in the assay and 3-fold serial dilutions were performed to give six concentrations. Each concentration was diluted 1:20 in media to give the intermediate concentration. DMSO was diluted 1:20 in media for use in wells without compound.

45 μl media plus 5 μl of the intermediate dilution of compound or DMSO was added to each test well in the assay plate. 100 μl of cells at $3\times10^5$ cells/ml were added to each well. Plates were incubated 60 minutes at 37° C. in 5% $CO_2$ and 50 μl of IL-2 at 200 units/ml to each well. Negative control wells received 100 μl media. The plates were incubated 3 days at 37° C. in 5% $CO_2$. 0.5 μC $^3$H-Thymidine in 20 μl media was added to each well and the plates incubated 6 hours at 37° C. in 5% $CO_2$. The plates were harvested onto a UNIFILTER®-96 GF/C filter plate (Perkin Elmer 6005174) using a Packard Filtermate Harvester. The bottom of each dried filter plate was sealed, 50 μl Microscint 20 (Perkin Elmer #6013621) added to each well and the top of the plate sealed. Proliferation as measured by $^3$H-Thymidine incorporation was determined by counting on a Packard TOPCOUNT®-NXT.

IL-2 Induced STAT3 Phosphorylation in PHA Blasts Assay

IL-2 expanded PHA blasts were prepared (see IL-2 Dependent T Cell Proliferation Assay Protocol for preparation of IL-2 expanded PHA blasts). Compounds were diluted in DMSO (in duplicate) to 333.3× final high concentration in the assay and 3-fold serial dilutions were performed to give six concentrations. Each concentration was diluted 1:20 in media to give the intermediate concentration. DMSO was diluted 1:20 in RPMI media (Gibco #61870) for use in wells without compound.

173 μl/well of a PHA blast cell suspension at $5.78\times10^6$ cells/ml was added to a round bottom tissue culture plate (FALCON® #353077) followed by 12 μl of the intermediate compound dilution or DMSO for wells without compound. The plate was incubated at 37° C. in 5% $CO_2$ for 30 minutes. 15 μl of 266.7 ng/ml IL-2 (R&D #202-IL-050) in media was added to each well or media only to negative control wells. The plates were mixed on an orbital shaker for 1 minute and incubated at 37° C. in 5% $CO_2$ for a total 10 minutes. Plates were centrifuged 4 minutes at 1500 rpm and 150 μl of culture supernatant was removed from each well leaving the pellet intact. Plates were mixed on an orbital shaker for 1 minute and 50 μl of 2× lysis buffer was added (20 mM Tris, pH7.5, 0.2 M NaCl, 2 mM EDTA, 2 mM EGTA, 2 mM NaF, 2 mM β-glycerophosphate, 40 mM sodium pyrophosphate, 4 mM $Na_3VO_4$ (add at time of use), 2% Triton X-100 (Sigma T9284), 20% glycerol (EM Science GX0185-6), 0.2% SDS (Bio-Rad #161-0416), 1.0% deoxycholate (Sigma D5670), 2× protease inhibitor cocktail (Sigma P2714, dissolved in 10 ml PBS to give 10× concentration, add at time of use)). The plates were incubated on ice for 1 hour and the lysate in each well was mixed by pipetting up and down 5-6 times. STAT3 phosphorylation levels were determined by ELISA (PATHSCAN® Phospho-STAT3 ELISA Antibody Pair, Cell Signaling #7146).

ELISA plates were coated with 100 Owen of a 1:100 dilution of Capture antibody in PBS and incubated at least overnight at 4° C. On day of use plates were washed 3× with wash buffer (PBS (Gibco #14190)+0.05% Tween 20). Plates were blocked with 200 μl/well of assay buffer 1 (AB1) (PBS+1% BSA+0.1% Tween 20 (Bio-Rad #161-0416)) for 2 hours at room temperature. Plates were washed 3× and 90 μl/well AB1 Buffer added. 10 μl/well of assay sample or standards were added followed by 100 μl/well of a 1:100 dilution of detection antibody in AB1 Buffer. Plates were incubated overnight at 4° C. and then washed 6×. 100 μl/well of a 1:1000 dilution of anti-mouse IgG HRP-linked antibody in AB1 Buffer was added to each well and plates were incubated 1 hour at room temperature. Plates were washed 6×. 100 μl of a 1:1 mix of TMB peroxidase substrate (KPL #50-76-01) and peroxidase substrate solution (KPL #50-65-00) was added and the plates were incubated in the dark at room temperature for 10-30 min. The reaction was stopped with 100 μl/well of 1N $H_2SO_4$ and the plates were read at 450 nm with correction at 650 nm within 30 min.

pSTAT3 standards were prepared from IL-6 stimulated TF-1 cells. TF-1 cells were washed 3× and resuspended at $1\times10^6$ cells/ml and rested overnight without GM-CSF at 37° C. in 5% $CO_2$. The cells were washed 1× and resuspended at $5\times10^6$ cells/ml. IL-6 was added to 20 ng/ml and cells incubated at 37° C. in 5% $CO_2$ for 15 minutes, spun 4 minutes at 1500 rpm and the supernatant removed. 150 μl lysis buffer was added for every $5\times10^6$ cells and incubated on ice for 60 minutes. Using a syringe fitted with a 21 gauge needle, lysates were passed 6 times through the needle. The lysates were transferred to microfuge tubes and centrifuged at 14K rpm for 10 minutes and the supernatants were combined and aliquots frozen on dry ice and stored at −80° C. The lysate was assigned a value of 100 units/ml of pSTAT3 and used as a standard in the pSTAT3 ELISA assay. Standards were diluted in a 1:2 dilution series using a 1:1 mix of 2× lysis buffer and media.

EPO Induced STAT5A Phosphorylation in TF-1 Cells

TF-1 cells were carried in cell culture media (RPMI w/10% fetal bovine serum (Summit Biotechnology #RS-50-05), 100 U/ml penicillin and 100 μg/ml streptomycin (Gibco #14140-122))+2 ng/ml GM-CSF (R&D #215GM). On the day before use the cells were washed 3×, resuspended at $1\times10^6$ cells/ml in media without GM-CSF and rested overnight at 37° C. in 5% $CO_2$. The cells were washed 1× and resuspended in media at $2.78\times10^6$ cells/ml. Compounds were prepared as in the IL-2 induced STAT3 phosphorylation in PHA blasts assay.

173 μl/well of a TF-1 cell suspension at $2.78\times10^6$ cells/ml was added to each well of a round bottom tissue culture plate (FALCON® #353077) followed by 12 μl of the intermediate compound dilution or DMSO for wells without compound. The plate was incubated at 37° C. in 5% $CO_2$ for 30 minutes. 15 μl of 13.33 units/ml recombinant human EPO (R&D #287-TC) in media was added to each well or media only to negative control wells. The plates were mixed on an orbital shaker for 1 minute and incubated at 37° C. in 5% $CO_2$ for a total 10 minutes. Plates were centrifuged 4 minutes at 1500 rpm and 150 µl of culture supernatant was removed from each well leaving the pellet intact. Plates were mixed on an orbital shaker for 1 minute and 50 µl of 2× lysis buffer was added (20 mM Tris, pH7.5, 0.2 M NaCl, 2 mM EDTA, 2 mM EGTA, 2 mM NaF, 2 mM β-glycerophosphate, 40 mM sodium pyrophosphate, 4 mM $Na_3VO_4$ (add at time of use), 2% Triton X-100 (Sigma T9284), 20% glycerol (EM Science GX0185-6), 0.2% SDS (Bio-Rad #161-0416), 1.0% deoxycholate (Sigma D5670), 2× protease inhibitor cocktail (Sigma P2714, dissolved in 10 ml PBS to give 10× concentration, add at time of use)). The plates were incubated on ice for 1 hour and the lysate in each well was mixed by pipetting up and down 5-6 times. STAT5A phosphorylation levels were determined by ELISA.

ELISA plates (NUNC® #439454) were coated with 100 µl/well of a 1:500 dilution of Capture antibody (Invitrogen #13-3600) in carbonate/bicarbonate buffer (Sigma #C3041) and incubated at least overnight at 4° C. On day of use plates were washed 3× with wash buffer (PBS (Gibco #14190)+ 0.05% Tween 20 (Bio-Rad #170-6531)). Plates were blocked with 200 µl/well of assay buffer 2 (AB2) (PBS+2% BSA (Sigma #A-9576)+0.1% Tween 20 (Bio-Rad #161-0416)) for 2 hours at room temperature. Plates were washed 3× and 90 µl/well AB2 buffer added. 10 µl/well of assay sample or standards were added followed by 100 µl/well of a 1:4000 dilution of detection antibody (Genway #18-785-210434) in AB2 Buffer. Plates were incubated overnight at 4° C. and then washed 6×. 100 µl/well of a 1:3000 dilution of HRP-Goat anti-rabbit IgG (Invitrogen #65-6120 in AB2 Buffer was added to each well and plates were incubated 1 hour at room temperature. Plates were washed 6×. 100 µl of a 1:1 mix of TMB peroxidase substrate (KPL #50-76-01) and peroxidase substrate solution (KPL #50-65-00) was added and the plates were incubated in the dark at room temperature for 10-30 minutes. The reaction was stopped with 100 µl/well of 1N $H_2SO_4$ and the plates were read at 450 nm with correction at 650 nm within 30 min. pSTAT5A standards were prepared from GM-CSF stimulated TF-1 cells. TF-1 cells were washed 3× and resuspended at $1\times10^6$ cells/ml and rested overnight without GM-CSF at 37° C. in 5% $CO_2$. The cells were washed 1× and resuspended at $5\times10^6$ cells/ml. GM-CSF was added to 50 ng/ml and cells incubated at 37° C. in 5% $CO_2$ for 15 minutes, spun 4 minutes at 1500 rpm and the supernatant removed. 150 µl lysis buffer was added for every $5\times10^6$ cells and incubated on ice for 60 minutes. Using a syringe fitted with a 21 gauge needle, lysates were passed 6 times through the needle. The lysates were transferred to microfuge tubes and centrifuged at 14K rpm for 10 minutes and the supernatants were combined and aliquots frozen on dry ice and stored at −80° C. The lysate was assigned a value of 100 units/ml of pSTAT5A and used as a standard in the pSTAT5A ELISA assay. Standards were diluted in a 1:2 dilution series using a 1:1 mix of 2× lysis buffer and media.

IFNα Induced STAT3 Phosphorylation in PHA Blasts

IFNα induced STAT3 phosphorylation in PHA blasts was performed exactly as the IL-2 induced STAT3 phosphorylation in PHA blasts assay except the cells were stimulated with 15 µl/well of 13,333 units/ml IFNα2a (R&D #11105-1) in media.

Myosin Light Chain Phosphorylation (pMLC) Assay

Mouse aortic smooth muscle A7r5 cells are cultured in complete DMEM media (Gibco Cat. #11995) substituted with 10% FBS (Gibco Cat. #SH30071) and 1% penicillin/streptomycin (Gibco Cat. #15140). $1.5\times10^3$ cells are plated in 384-well tissue culture plates (Becton Dickinson Cat. #3962) and incubated overnight at 37° C. and 5% $CO_2$. Cells are then incubated with test compounds (serially diluted 3-fold with final concentrations ranging from 20 µM to 340 pM) for 60 minutes at 37° C. and 5% $CO_2$. Cell culture media is removed and cells are fixed with 4% paraformaldehyde (JT Baker Cat. #2106) for 60 min at room temperature. After removal of the fixing reagent, 1× permeabilization buffer (Thermo Cat. #1860291) is added for 10 min incubation at room temperature. Permeabilization buffer is removed and 1× blocking solution (Thermo Cat. #1860291) is added for 60 min incubation at room temperature. Blocking solution is removed and cells are incubated overnight at 4° C. with primary anti-pMLC antibody (Cell Signaling Cat. #3674) diluted in 1× blocking buffer for a final concentration of 70 ng/ml. Primary antibody is removed followed by 3 washes with 1×PBS (Gibco Cat. #14190). Cells are incubated for 60 min at room temperature with secondary AlexaFluor 488 Goat-anti rabbit IgG (H+L) antibody (Invitrogen Molecular Probes Cat. #A11008) at a final concentration of 5 µg/ml in 1× blocking buffer mixed with Hoechst nuclear stain (Invitrogen Molecular Probes Cat. #H3570) at 5 µg/ml final concentration. Cells are then washed 3 times with 1×PBS to remove reagents. The plates containing 30 µl 1×PBS per well are then scanned on the Cellomics ARRAY-SCAN® imager using the Cell Health Profiling BioApplication. The Mean Ring Spot Average Intensity of the FITC channel is used as the final readout to calculate $IC_{50}$ values. 0% inhibition is determined with 0.2% DMSO and 100% inhibition is determined with 1 mM of the Rho Kinase inhibitor H-1152P (Calbiochem Cat. #555550).

The Examples herein have been tested and have been found to have activity of less than or equal to 1 µM in at least one of the JAK3 assays described above. The compounds listed in Table 1 have been tested in the above assays with the results indicated.

TABLE 1

| Example No. | JAK3 $IC_{50}$ (µM) | JAK1 $IC_{50}$ (µM) |
|---|---|---|
| 1 | 0.0013 | 0.0040 |
| 2 | 0.0010 | 0.0057 |
| 3 | 0.0013 | 0.0083 |
| 4 | 0.0011 | 0.0053 |
| 5 | 0.0010 | 0.0205 |
| 6 | 0.0010 | 0.0067 |
| 7 | 0.0012 | 0.0186 |
| 8 | 0.0013 | 0.0193 |
| 9 | 0.0031 | 0.0069 |
| 10 | 0.0012 | 0.0043 |
| 11 | 0.0009 | 0.0057 |
| 12 | 0.0015 | 0.0169 |
| 13 | 0.0012 | 0.0033 |
| 14 | 0.0006 | 0.0024 |
| 15 | 0.0010 | 0.0056 |
| 16 | 0.0014 | 0.0096 |
| 17 | 0.0015 | 0.0017 |
| 18 | 0.0015 | 0.0042 |
| 19 | 0.0050 | 0.0089 |
| 20 | 0.0020 | 0.0042 |
| 21 | 0.0013 | 0.0022 |
| 22 | 0.0084 | 0.0129 |
| 23 | 0.0025 | 0.0025 |
| 24 | 0.0018 | 0.0027 |
| 25 | 0.0016 | 0.0011 |
| 26 | 0.0008 | 0.0006 |
| 27 | 0.0012 | 0.0018 |
| 28 | 0.0007 | 0.0011 |
| 29 | 0.0029 | 0.0042 |
| 30 | 0.0011 | 0.0008 |
| 31 | 0.0030 | 0.0024 |
| 32 | 0.0018 | 0.0022 |

TABLE 1-continued

| Example No. | JAK3 IC$_{50}$ (μM) | JAK1 IC$_{50}$ (μM) |
|---|---|---|
| 33 | 0.0036 | 0.0071 |
| 34 | 0.0044 | 0.0097 |
| 35 | 0.0009 | 0.0014 |
| 36 | 0.0010 | 0.0068 |
| 37 | 0.0016 | 0.0148 |
| 38 | 0.0010 | 0.0050 |
| 39 | 0.0006 | 0.0038 |
| 40 | 0.0011 | 0.0028 |
| 41 | 0.0020 | 0.0061 |
| 42 | 0.0010 | 0.0044 |
| 43 | 0.0006 | 0.0043 |
| 44 | 0.0016 | 0.0123 |
| 45 | 0.0007 | 0.0058 |
| 46 | 0.0017 | 0.0079 |
| 47 | 0.0009 | 0.0059 |
| 48 | 0.0007 | 0.0039 |
| 49 | 0.0010 | 0.0090 |
| 50 | 0.0011 | 0.0039 |
| 51 | 0.0010 | 0.0059 |
| 52 | 0.0005 | 0.0023 |
| 53 | 0.0006 | 0.0003 |
| 54 | 0.0005 | 0.0004 |
| 55 | 0.0005 | 0.0002 |
| 56 | 0.0040 | 0.0020 |
| 57 | 0.0045 | 0.0040 |
| 58 | 0.0034 | 0.0037 |
| 59 | 0.0025 | 0.0030 |
| 60 | 0.0037 | 0.0037 |
| 61 | 0.0137 | 0.0031 |
| 62 | 0.0015 | 0.0003 |
| 63 | 0.0051 | 0.0012 |
| 64 | 0.0010 | 0.0004 |
| 65 | 0.0023 | 0.0036 |
| 66 | 0.0013 | 0.0116 |
| 67 | 0.0012 | 0.0080 |
| 68 | 0.0008 | 0.0089 |
| 69 | 0.0008 | 0.0058 |
| 70 | 0.0022 | 0.0010 |
| 71 | 0.0250 | 0.0198 |
| 72 | 0.0005 | 0.0030 |
| 73 | 0.0006 | 0.0042 |
| 74 | 0.0007 | 0.0050 |
| 75 | 0.0007 | 0.0067 |
| 76 | 0.0160 | 0.0013 |

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the preparations and examples and intermediates section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

ABBREVIATIONS

Ac acetyl
ACN acetonitrile
AcOH or HOAc acetic acid
aq. aqueous
anhyd. anhydrous
ATP adenosine triphosphate
Bn benzyl
Bu butyl
Boc tert-butoxycarbonyl
BOP Benzotriazole-1-yl-oxy-tris-(dimethylamino)-phosphonium hexafluorophosphate
CDI carbonyldiimidazole
° C. degrees Centigrade
Cbz carbobenzyloxy
Conc. concentration
d days
DAST (diethylamino)sulfur trifluoride
DBU 1,8-Diazabicyclo[5.4.0]undec-7-ene
DCE 1,2-dichloroethane
DCM dichloromethane
DEA diethylamine
DIEA or DIPEA diisopropylethylamine
DMAP dimethylaminopyridine
DMA N,N-dimethylacetamide
DME 1,2-dimethoxyethane
DMF dimethylformamide
DMSO dimethylsulfoxide
DPPA diphenylphosphorylazide
dppf 1,1'-Bis(diphenylphosphino)ferrocene
DTT dithiothreitol
EDC or EDCI or EDAC 1-(3-Dimethylaminopropyl)-3-ethylcarbodiimide hydrochloride
EDTA ethylenediaminetetraacetic acid
EGTA ethylene glycol tetraacetic acid
% ee percent enantiomeric excess
(+/−) or (±) racemic
eq. or Eq. or equiv. equivalents
EtOAc or EA Ethyl acetate
Et Ethyl
EtOH Ethanol
Ex Example
GST glutathione S-transferase
H Hydrogen
HATU N,N,N,N-tetramethyl-O-(7-azabenzotriazol-1-yl) uranium hexafluorophosphate
hex hexanes
HIS histidine
h or hr Hours
I iso
IPA isopropanol
Hz hertz
MHz megahertz
HPLC High pressure liquid chromatography
RP-HPLC Reverse-phase high pressure liquid chromatography
HOBT 1-Hydroxybenzotriazole hydrate
Lawesson's Reagent [2,4-bis(4-methoxyphenyl)-1,3-dithia-2,4-diphosphetane-2-4-disulfide
LC liquid chromatography
LCMS or LC/MS liquid chromatograph mass spectrometry
LDA lithium diisopropylamide m-CPBA or MCPBA meta-chloroperbenzoic acid
Me methyl
MeOH methanol
min. minutes
$M^+$ $(M+H)^+$
$M^{+1}$ $(M+H)^+$
MS mass spectrometry
MSA methanesulfonic acid
MTBE methyl tert-butyl ether
m/z mass to charge ratio
N Normal
NMP N-methylpyrrolidinone
NMR nuclear magnetic resonance
PBMC peripheral blood mononuclear cells
PhCONCS benzyolyisothiocyanate
Pd/C palladium on carbon
Ph phenyl
Pr propyl
PHA phytohemagglutinin
ppm parts per million
PSI or psi pounds per square inch
quant. quantitative
Ret Time or Rt retention time
rt or RT room temperature
sat. or sat'd. saturated
sec seconds
SFC super critical fluid
S-Tol-BINAP (S)-(−)-2,2'-Bis(di-p-tolylphosphino)-1,1'-binapthyl
SM or sm starting material
t tert
TEA triethylamine
TFA trifluoroacetic acid
THF tetrahydrofuran
TLC thin layer chromatography
TMS-I or TMSI iodotrimethylsilane
p-TSA para-toluenesulfonic acid
Xantphos (9,9-dimethyl-9H-xanthene-4,5-diyl)bis[diphenylphosphine]
t triplet
m multiplet
s singlet
d doublet
br. s. broad singlet
dd doublet of doublets
tt triplet of triplets
ddd doublet of doublet of doublets
q quartet
quin. Quintet
W/V or w/v weight to volume
X-Phos dicyclohexyl(2',4',6'-triisopropylbiphenyl-2-yl)phosphine The compounds of formula I may be prepared by the processes described herein in the following reaction Schemes. Examples of suitable reagents and procedures for conducting these reactions appear hereinafter and in the working examples included therein. Protection and deprotection in the schemes herein may be carried out by procedures generally known in the art (See, for example, Greene, T. W. et al., *Protecting Groups in Organic Synthesis*, 3rd Edition, Wiley (1999)).

Compounds of the formula I can be prepared from imidazole of the formula II as depicted in Scheme A. Imidazole of formula II may be obtained by processes known in the art. Reacting an imidazole of formula II wherein $R^2$ is as previously defined with an aminating reagent, such as chloramines or (aminooxy)diphenylphosphine oxide, in the presence of a base, such as sodium hydride or lithium bis(trimethylsilyl)amide, in a solvent, such as DMF, affords the aminated imidazole of formula III. Compounds of formula III can be N-protected via reaction with di-tert-butyl dicarbonate to afford a compound of formula IV. Compounds of formula IV can be brominated with a brominating agent, such as bromine or N-bromosuccinimide, in a solvent, such as DMF, to afford a compound of formula V as the major product. Compounds of formula V can react with ethyl acetate in the presence of a base, such as potassium tert-butoxide in a solvent such as THF, to afford a compound of formula VI. Reacting Compounds of formula VI with 1,1-dimethoxy-N,N-dimethylmethanamine (DMF-DMA) in a solvent such as DCM, at room temperature affords cyclized products of the formula VII. Compounds of formula VII can be hydrolyzed with hydrolyzing agents, such as lithium hydroxide or potassium hydroxide, in a protonic solvent, such as ethanol and water, under elevated temperature ranging from 45-100° C. to afford a compound of formula VIII. Reaction of compounds of formula VIII with a chlorinating agent, such as phosphorus oxychloride or thionyl chloride, followed by quenching the obtained intermediate with a nucleophilic amine of the formula $R^3NH_2$, such as ammonia ($R^3$=H), at the temperature ranging from −40° C. to 0° C. affords products of the formula IX. Compounds of the formula IX can then be coupled to amines of the formula $R^1NH_2$ in the presence of a suitable base in a suitable solvent to afford compounds of the formula X, which are compounds of the formula I wherein $R^2$ is bromo. Examples of suitable bases for the coupling include NaH, $Et_3N$, DIPEA, $K_2CO_3$ or $Na_2CO_3$ and suitable solvents include THF, $CH_3CN$, DMF, NMP, DMA, $CH_2Cl_2$. Most preferable base is DIPEA and more preferable solvents include DMF, NMP, and DMA.

Compounds of the formula X can be reacted with boronic acids of the formula $R_2B(OH)_2$ or boronate esters of the formula $R_2B(OR)_2$ under Suzuki-Miyaura coupling conditions which are readily known to those skilled in the art, to afford compounds of the formula I, wherein $R^2$ is substituted or unsubstituted aryl or heteroaryl.

Scheme A

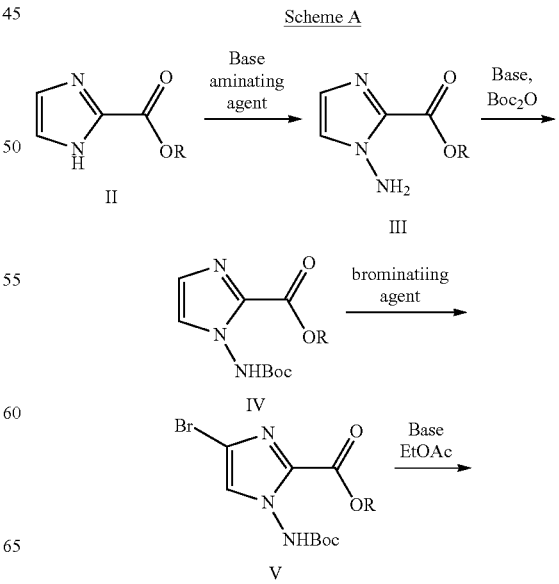

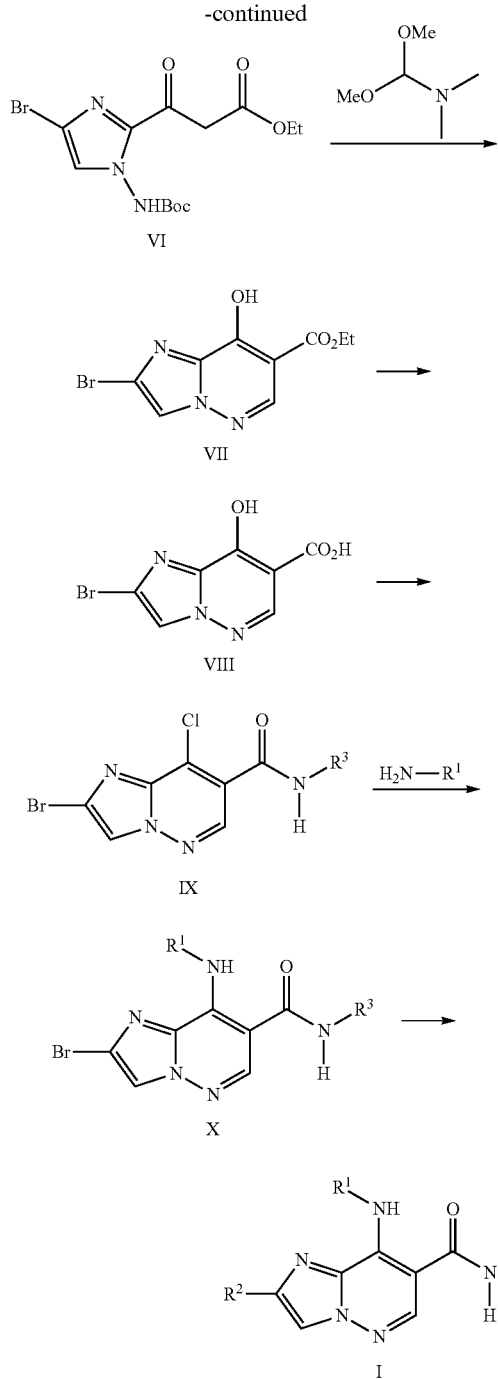

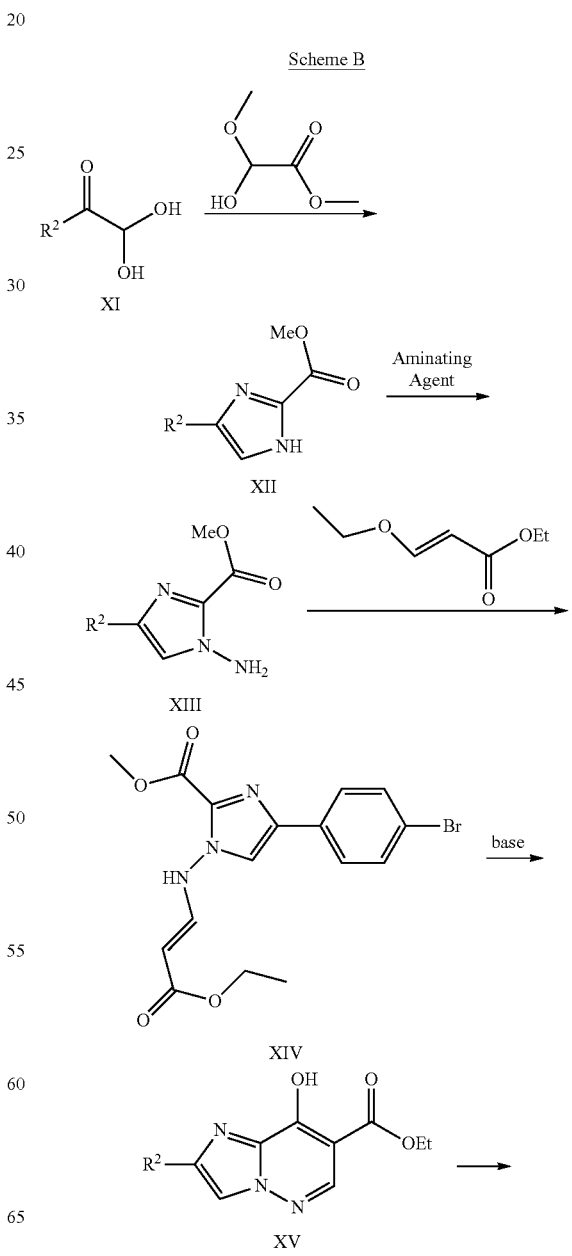

3-ethoxyacrylate in the presence of an acid catalyst, such as p-TSA, in a suitable solvent, such as ethanol, to afford compounds of the formula XIV, followed by base induced cyclization employing a base such as DBU, in a solvent such as ethanol to afford compounds of the formula XV. Reaction of compounds of the formula XV with a hydrolyzing reagent as previously described in Scheme A affords compounds of formula XVI. Reaction of compounds of formula XVI with a chlorinating agent, followed by quenching the obtained intermediate with a nucleophilic amine of the formula $R^3NH_2$, such as ammonia ($R^3$=H) as previously described in Scheme A affords products of the formula XVII, which can be coupled with amines of the formula $R^1NH_2$ as previously described in Scheme A to afford compounds of the formula I, wherein $R^2$ is substituted or unsubstituted aryl or heteroaryl.

Scheme B depicts an alternative route to the synthesis of compounds of the formula I starting from compounds of the formula XI. According to a literature procedure (U.S. Publication No. 2010/0016303A1), Compounds of formula XI, wherein $R^2$ is substituted or unsubstituted aryl or heteroaryl, can react with methyl 2-hydroxy-2-methoxyacetate in the presence of ammonium acetate and acetic acid to afford the imidazole of formula XII. Reaction of imidazoles of the formula VIII with an aminating reagent as described in Scheme A affords compounds of the formula XIII. Compounds of the formula XIII can be condensed with ethyl

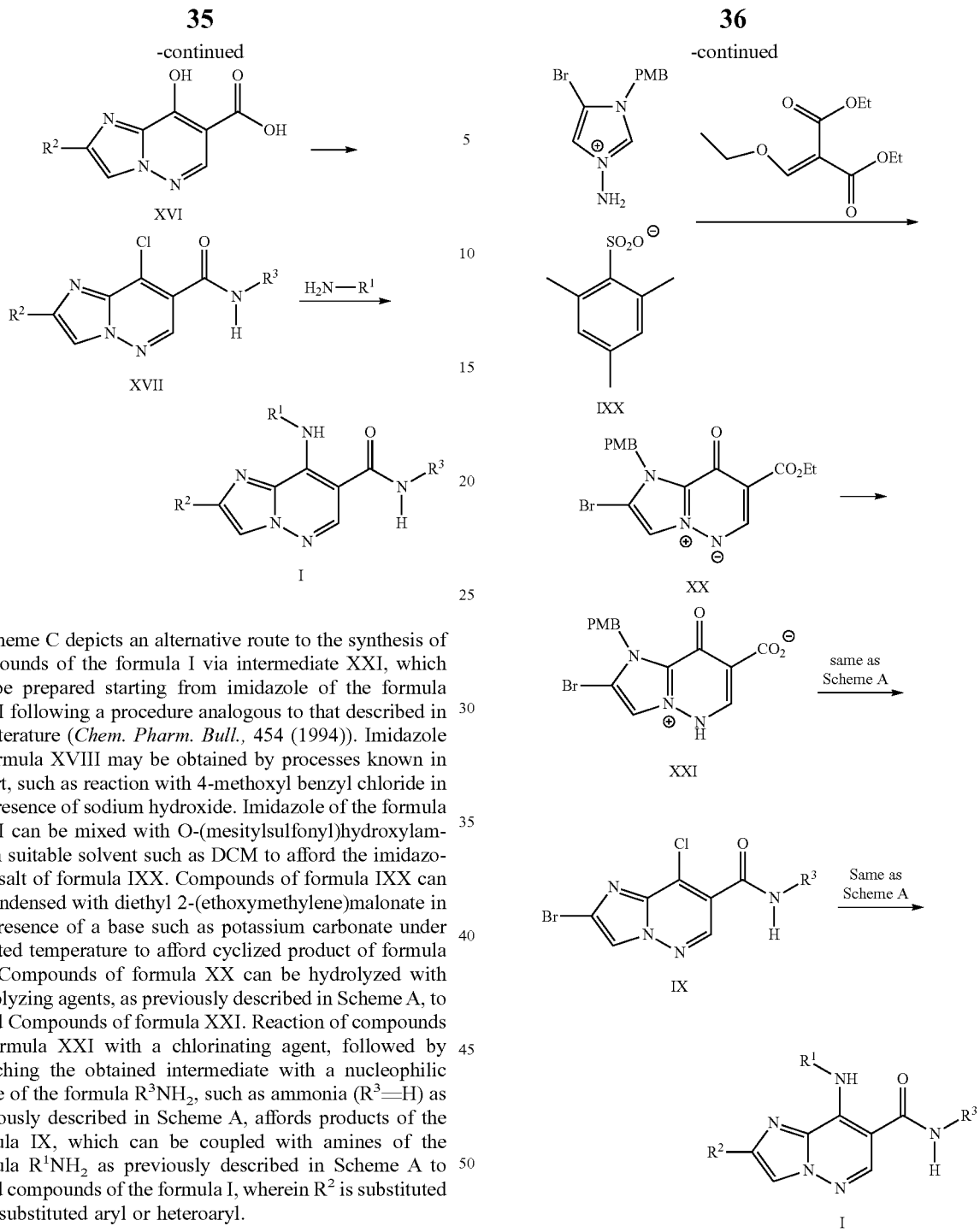

Scheme C depicts an alternative route to the synthesis of compounds of the formula I via intermediate XXI, which can be prepared starting from imidazole of the formula XVIII following a procedure analogous to that described in the literature (*Chem. Pharm. Bull.*, 454 (1994)). Imidazole of formula XVIII may be obtained by processes known in the art, such as reaction with 4-methoxyl benzyl chloride in the presence of sodium hydroxide. Imidazole of the formula XVIII can be mixed with O-(mesitylsulfonyl)hydroxylamine in suitable solvent such as DCM to afford the imidazolium salt of formula IXX. Compounds of formula IXX can be condensed with diethyl 2-(ethoxymethylene)malonate in the presence of a base such as potassium carbonate under elevated temperature to afford cyclized product of formula XX. Compounds of formula XX can be hydrolyzed with hydrolyzing agents, as previously described in Scheme A, to afford Compounds of formula XXI. Reaction of compounds of formula XXI with a chlorinating agent, followed by quenching the obtained intermediate with a nucleophilic amine of the formula $R^3NH_2$, such as ammonia ($R^3$=H) as previously described in Scheme A, affords products of the formula IX, which can be coupled with amines of the formula $R^1NH_2$ as previously described in Scheme A to afford compounds of the formula I, wherein $R^2$ is substituted or unsubstituted aryl or heteroaryl.

Scheme C

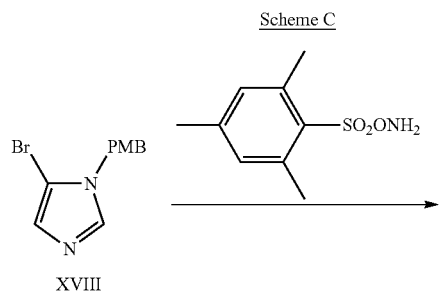

As depicted in Scheme D, compounds of the formula I can be prepared by reacting compounds of the formula X with diboranes of the general formula $(RO)_2B—B(OR)_2$ under palladium catalyzed conditions readily known to those skilled in the art to afford compounds of the formula XXII. Compounds of the formula XXII can then be coupled to reagents of the type $R^2$—X, where X is most commonly chloro, bromo, or trifluoromethanesulfonate to afford compounds of the formula I, wherein $R^2$ is substituted or unsubstituted aryl or heteroaryl.

Scheme D

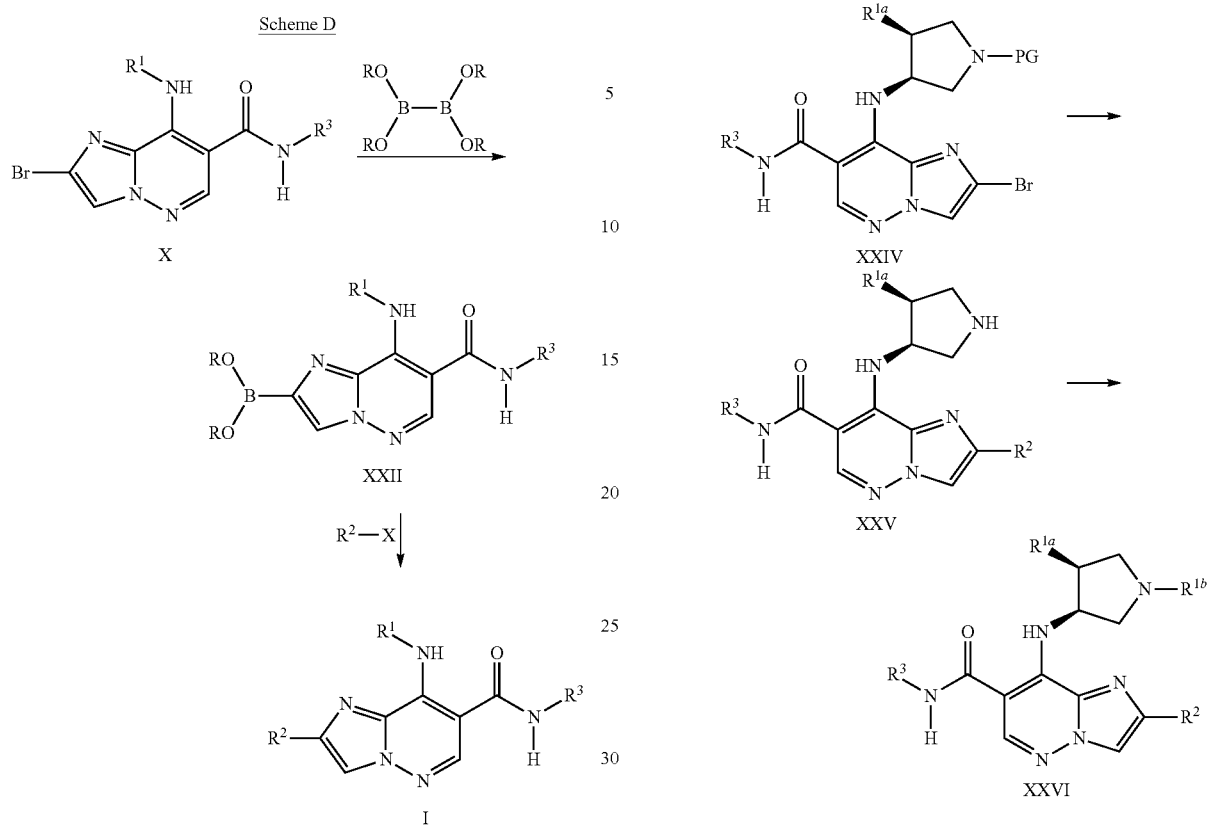

As depicted in Scheme E, pyrrolidine compounds of the formula XXVI can be prepared from the coupling of pyrrolidine intermediates of the formula XXIII with compounds of the formula IX (prepared as in Scheme A) to afford compounds of the formula XXIV where PG is a suitable protecting group, such as tert-butoxycarbonyl (Boc) or benzyloxycarbonyl (Cbz). Compounds of the formula XXIV can be functionalized with a suitable $R^2$ group by methods known in the art and by methods described herein followed by deprotection (removal of PG) using methods known in the art to afford compounds of the formula XXV. Compounds of the formula XXV can be functionalized with suitable $R^{1b}$ groups by methods known in the art and by using methods described herein to afford compounds of the formula XXVI.

Scheme E

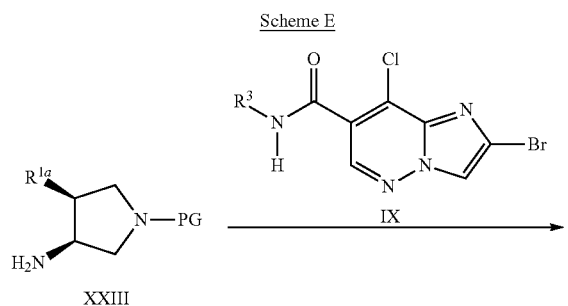

Suitably substituted pyrrolidine intermediates represented by $R^1NH_2$ can be prepared by methods known by those skilled in the art (for example, see *Targets in Heterocyclic Synthesis*, 13:147-171 (2009) and *Tetrahedron*, 60(8):1701-1729 (2004) and references therein). More specifically, as depicted in Scheme F, suitably substituted pyrrolidine intermediates of the formula XXXI can be prepared from compounds of the formula XXVII where PG is a suitable protecting group (PG) such as butoxycarbonyl (Boc) or benzyloxycarbonyl (Cbz). Oxidation using suitable oxidizing reagents, such as mCPBA, affords compounds of the formula XXVIII followed by epoxide opening with nucleophilic reagents, such as alkyl Grignards in the presence of a copper salt, such as copper iodide, affords compounds of the formula IXXX wherein $R^{1a}$ is a suitable alkyl group. Alternatively, reacting compounds of the formula XVIII with alcohols, such as methanol, in the presence of a suitable acid catalyst, such as sulfuric acid, affords compounds of the formula IXXX wherein $R^{1a}$ is a suitable alkoxy group. Compounds of the formula IXXX can then be reacted with suitable activating reagents, such as toluenesulfonyl chloride, in the presence of a suitable base, such as pyridine, in the presence of a suitable solvent such as dichloromethane, followed by reaction of the activated alcohol intermediate with a suitable azide reagent, such as sodium azide, to afford compounds of the formula XXX. Compounds of the formula XXX can be reacted with a suitable reducing reagent, such as triphenylphosphine, in a suitable solvent to afford pyrrolidine compounds of the formula XXXI. Enantiopure compounds of the formula XIII having the preferred 3-(S) configuration can be obtained by resolution using chiral chromatography methods which are known by those skilled in the art.

Scheme F

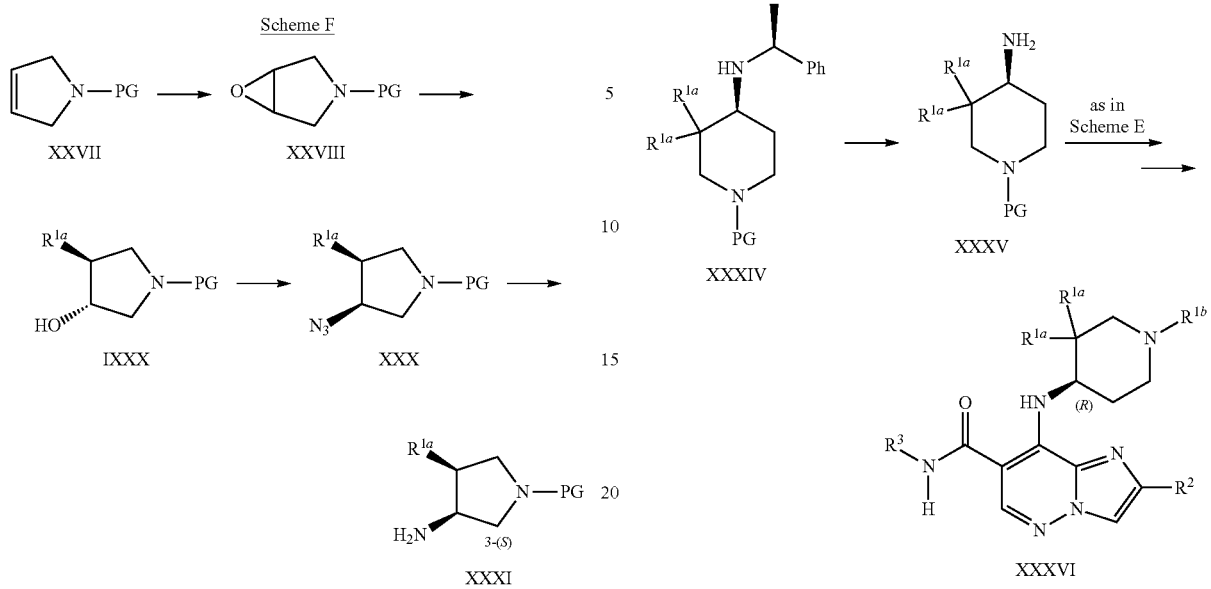

Suitably substituted piperidine intermediates represented by $R^1NH_2$ can be prepared by methods known by those skilled in the art (for example, see *Targets in Heterocyclic Synthesis*, 13:147-171 (2009) and *Tetrahedron*, 60(8):1701-1729 (2004) and references therein). More specifically, as depicted in Scheme G, suitably substituted piperidine intermediates of the formula XXXVI can be prepared from available compounds of the formula XXXII where PG is a suitable protecting group (PG) such as butoxycarbonyl (Boc) or benzyloxycarbonyl (Cbz). Reaction with α-methylbenzylamine in a suitable solvent, such as benzene, in the presence of a water scavenger, such as molecular sieves, affords imine compounds of the formula XXXIII. Reduction of the imines using a suitable reducing agent, such as sodium borohydride, in a suitable solvent, such as ethanol, affords amines of the formula XXXIV. Hydrogenolysis using a suitable catalyst, such as palladium hydroxide on carbon, in a suitable solvent, such as acetic acid, in the presence of hydrogen gas affords amines of the formula XXXV which can be transformed to final compounds of the formula XXXVI as previously described in Scheme E. Enantiopure compounds of the formula XXXVI having the preferred (R)-configuration can be obtained by using enantiopure (R)-α-methylbenzylamine in the preparation.

Scheme G

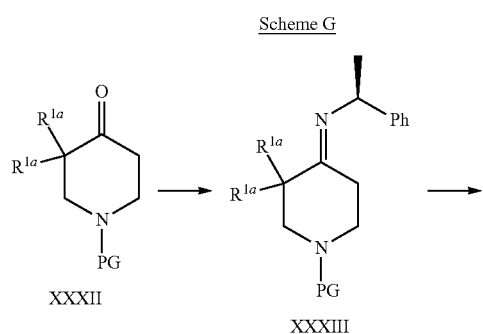

Analytical HPLC Conditions

Method A: Column: PHENOMENEX® Synergy, 4.6×50 mm, Mobile Phase A: 90:10 water/methanol with 0.2% $H_3PO_4$; Mobile Phase B: 90:10 methanol/water with 0.2% $H_3PO_4$; Gradient: 0-100% B over 4 minutes, then a 1-minute hold at 100% B; Flow: 4 mL/min. 220 nm or 254 nm detection wavelength.

Method B: Column: YMC COMBISCREEN® ODS-A, 4.6×50 mm, Mobile Phase: 10-90% aq $CH_3OH/0.2\%$ $H_3PO_4$, 4.0 min. gradient with 1.0 min. hold, Flow rate: 4 ml/min, 220 nm or 254 nm detection wavelength.

Method C: Column: XBridge C18, 3.5 μm 4.6×50 mm, Mobile Phase A: 90:10 water/methanol with 0.1% TFA; Mobile Phase B: 90:10 methanol/water with 0.1% TFA; Wavelength: 254 nm; Gradient: 0-100% B over 15 minutes, then a 3-minute hold at 100% B; Flow: 1 mL/min; Temperature: 40° C.

Method D: Column: XBridge Phenyl C18, 3.5 μm 4.6×50 mm, Mobile Phase A: 95:5 water/acetonitrile with 0.05% TFA; Mobile Phase B: 95:5 acetonitrile/water with 0.05% TFA; Wavelength: 254 nm; Gradient: 0-100% B over 12 minutes, then a 3-minute hold at 100% B; Flow: 1 mL/min.

Method E: Column: Walters Xbridge C18, 4.6×50 mm, 5 μm, Flow rate: 4 mL/min; Solvent A: 5:95 acetonitrile:water with 10 mM $NH_4OAc$, Solvent B: 95:5 acetonitrile: water with 10 mM $NH_4OAc$; Linear gradient of 0 to 100% Solvent B over 4 min, with 1 min hold at 100% B.

Analytical LCMS Conditions

Method A: Column: BEH C18 2.1×50 mm 1.7μ; Linear gradient of 0-100% Solvent B over 2 min, then 0.5 min hold at 100% B; Flow rate: 1 mL/min; Solvent A: 100% water w/ 0.05% TFA; Solvent B: 100% acetonitrile w/ 0.05% TFA; Products detected at 220 wavelength w/ positive ionization mode.

Method B: Column: Luna C18 4.6×30 mm 3μ A: 10:90 $H_2O$:MeOH TFA/B: 10:90 $H_2O$:MeOH TFA; 0%-95% B in 2 min; 4 mL/min flow. Product detected by positive ionization mode.

Method C: Column: Luna C18 4.6×30 mm 3μ A: 10:90 $H_2O$:ACN $NH_4OAc$/B: 10:90 $H_2O$:ACN $NH_4OAc$; 0%-95% B in 2 min; 4 mL/min flow. Product detected by positive or negative ionization mode.

Analytical HPLC/LCMS Conditions

Method E: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method F: Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min. Proton NMR was acquired in deuterated 1:1 methanol:chloroform.

Preparative HPLC Conditions

Method A: Column: Luna 5μ C18 30×100 mm; Flow rate=40 mL/min; Solvent A=10% MeOH-90% $H_2O$-0.1% TFA; Solvent B=90% MeOH-10% $H_2O$-0.1% TFA, Start % B=0-30, Final % B=80-100, linear gradient time=10-12 min; Pdts detected at 220 wavelength.

Preparative LC/MS Conditions

Method A: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 15 minutes, then a 5-minute hold at 100% B; Flow: 20 mL/min.

INTERMEDIATES

Intermediate 1

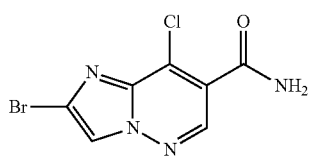 [SMILES: NC(=O)c1cnn2cc(Br)nc2c1Cl]

Step 1: Ethyl 1-amino-1H-imidazole-2-carboxylate

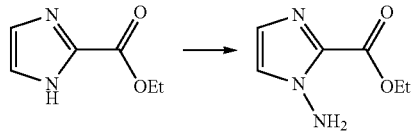 [SMILES: CCOC(=O)c1ncc[nH]1 ; CCOC(=O)c1nccn1N]

To a solution of ethyl 1H-imidazole-2-carboxylate (2.00 g, 14.27 mmol) in DMF (40 mL) at 0° C. was added sodium hydride (0.714 g, 17.84 mmol, 60% wt). The reaction solution was stirred at room temperature for 120 min and then was cooled to 0° C. A suspension of (aminooxy)diphenylphosphine chloride [4.66 g, 19.98 mmol, prepared from diphenylphosphinic chloride following a known procedure (*Org. Lett.*, 351-353 (2007))], in DMF (70 ml) was added. After 10 min, the ice bath was removed. The reaction mixture became viscous and stirred at room temperature for 3 h. The reaction was quenched with water until it became a clear solution, and concentrated to dryness under reduced pressure. The crude product was suspended in EtOAc (400 ml) with stirring for 30 min and filtered. The filtrate was concentrated to give a pale yellow viscous solid, 2.6 g. The crude product was purified via silica gel column (Isco prep: 0-5% MeOH-DCM over 20 minutes) to afford ethyl 1-amino-1H-imidazole-2-carboxylate (1.99 g, 90% yield) as a white solid. $^1$H NMR (400 MHz, MeOD) δ 7.35 (d, J=1.3 Hz, 1H), 7.11 (s, 1H), 4.37 (q, J=7.3 Hz, 2H), 1.50 (br. s., 9H), 1.38 (t, J=7.0 Hz, 4H). ESI-MS (analytical LCMS Method A): m/z 156.0 ([M+H]$^+$).

Alternative procedure using 1M LiN(TMS)$_2$ as base: A 1M THF solution of LiHMDS (19.62 ml, 19.62 mmol) was added dropwise to a solution of ethyl 1H-imidazole-2-carboxylate (2.5 g, 17.84 mmol) in DMF (119 ml) at 0° C. The reaction was stirred at 0° C. for 10 minutes. A DMF (119 ml) suspension of (aminooxy)diphenylphosphine oxide (4.99 g, 21.41 mmol) was added. After stirring for 10 minutes, the ice bath was removed, and stirring was continued at room temperature. After 3 hrs, the starting material was completely consumed. Water was added portion-wise to the reaction mixture until complete dissolution of the suspension. The clear solution was concentrated to dryness under reduced pressure. Ethyl acetate was added to the solid, forming a yellow suspension. The suspension was stirred for 15 minutes and filtered. The solid was washed with ethyl acetate and dichloromethane, successively. The collected organic wash was concentrated. The crude product was dissolved in 10% MeOH/DCM (10 ml) and was chromatographed on a prepacked silica gel column (Isco prep: 0-5% MeOH-DCM over 20 minutes. The product began eluting around 7 minutes (~2% MeOH/DCM). The desired ethyl 1-amino-1H-imidazole-2-carboxylate (2.57 g, 16.56 mmol, 93% yield) was obtained as a white solid.

Step 2: Ethyl 1-((tert-butoxycarbonyl)amino)-1H-imidazole-2-carboxylate

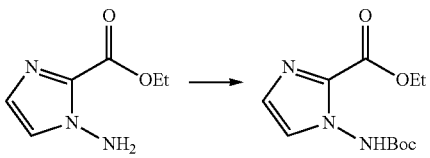 [SMILES: CCOC(=O)c1nccn1N ; CCOC(=O)c1nccn1NC(=O)OC(C)(C)C]

To a solution of ethyl 1-amino-1H-imidazole-2-carboxylate (1.776 g, 11.35 mmol) and DMAP (0.699 g, 5.73 mmol) in DMF (18 ml) was added di-tert-butyl dicarbonate (3.61 ml, 15.55 mmol). The reaction was heated at 85° C. for 4 h, and was then evaporated to dryness under reduced pressure. The crude product mixture was dissolved in a small amount of DCM and charged to a 40 g silica gel cartridge which was eluted with 10-40% EtOAc in hexane to give ethyl 1-((tert-butoxycarbonyl)amino)-1H-imidazole-2-carboxylate as a white solid (2.13 g, 72.9% yield). LCMS (Method B): m/z 256.1 [M+1]; HPLC (Method B): Rt 2.163 min. $^1$H NMR (400 MHz, MeOD) δ 7.34 (d, J=1.3 Hz, 1H), 7.11 (d, J=1.1 Hz, 1H), 5.49 (s, 1H), 4.37 (q, J=7.0 Hz, 2H), 1.49 (br. s., 9H), 1.42-1.35 (m, 3H).

Step 3: Ethyl 4-bromo-1-((tert-butoxycarbonyl) amino)-1H-imidazole-2-carboxylate

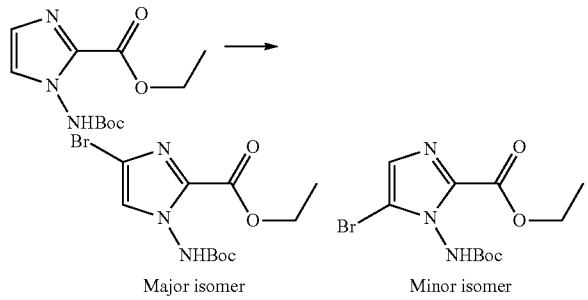

Major isomer    Minor isomer

A solution of NBS (1.548 g, 8.70 mmol) in DMF (15 ml) was added slowly via addition funnel to a solution of ethyl 1-((tert-butoxycarbonyl)amino)-1H-imidazole-2-carboxylate (2.22 g, 8.70 mmol) in DMF (12 ml) at room temperature. The reaction was stirred at room temperature overnight. To the reaction was added a saturated solution of sodium bicarbonate until the yellow solution became a white suspension. The mixture was concentrated to dryness. The residue was partitioned between EtOAc and water. The organic phase was washed (brine), dried (Na$_2$SO$_4$) and concentrated to give a yellow viscous oil. The crude product was purified via silica gel column (Isco prep: 15-100% ethyl acetate/hexanes) to afford ethyl 4-bromo-1-((tert-butoxycarbonyl)amino)-1H-imidazole-2-carboxylate (1.52 g, 4.55 mmol, 52.3% yield) as a white solid. LCMS (Method B) m/z 334.1 [M+1], Br-pattern; $^1$H NMR (400 MHz, chloroform-d) δ 7.26 (s, 1H), 4.42 (q, J=7.1 Hz, 2H), 1.51 (s, 9H), 1.42 (t, J=7.2 Hz, 3H).

In addition, the minor isomer (more polar fraction), ethyl 5-bromo-1-((tert-butoxycarbonyl)amino)-1H-imidazole-2-carboxylate (0.343 g, 1.026 mmol, 11.80% yield) and recovered starting material (most polar fraction) ethyl 1-((tert-butoxycarbonyl)amino)-1H-imidazole-2-carboxylate (0.236 g, 0.925 mmol, 10.63% yield) were also collected. $^1$H NMR (400 MHz, chloroform-d) δ 7.48 (br. s., 1H), 7.18 (s, 1H), 4.42 (q, J=7.0 Hz, 2H), 1.51 (s, 9H), 1.42 (t, J=7.2 Hz, 4H).

Step 4: Ethyl 3-(4-bromo-1-((tert-butoxycarbonyl) amino)-1H-imidazol-2-yl)-3-oxopropanoate

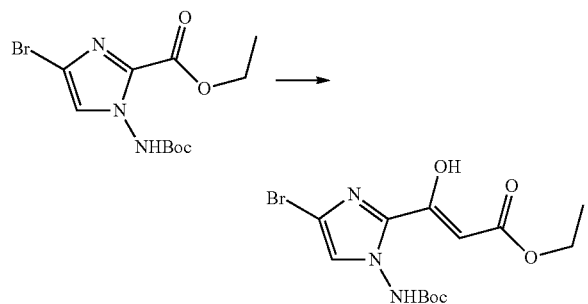

To a solution of ethyl 4-bromo-1-((tert-butoxycarbonyl) amino)-1H-imidazole-2-carboxylate (1.90 g, 5.69 mmol) in THF (4.4 ml) at 0° C., was added dropwise a cold (pre-cooled at 0° C.) 1M THF solution of potassium tert-butoxide (17.06 ml, 17.06 mmol). The reaction was stirred at 0° C. for 5 minutes. Dry ethyl acetate (1.410 ml, 14.40 mmol), which was pre-cooled at 0° C., was added dropwise. Stirring was continued at 0° C. for 15 minutes. The ice bath was removed. The reaction was stirred at room temperature for 2 hrs, becoming a darker yellow suspension. The reaction was cooled to 0° C., and treated with 1.0 N HCl via dropwise addition until complete dissolution of the suspension. The reaction was concentrated to half volume under reduced pressure, and diluted with ethyl acetate. The solution was adjusted to basic by addition of 1.0 N NaOH. The aq. layer was back extracted with ethyl acetate (3×). The ethyl acetate extracts were combined, dried with sodium sulfate, filtered, and concentrated to give ethyl 3-(4-bromo-1-((tert-butoxycarbonyl)amino)-1H-imidazol-2-yl)-3-oxopropanoate (1.502 g, 4.00 mmol, 70% yield) as a pale yellow solid. LCMS (Method B) m/z 376.1 [M+1], Br-pattern; HPLC (Method B): Rt 2.961 min. $^1$H NMR (400 MHz, MeOD, enoate form) δ 7.51 (s, 1H), 4.18 (q, J=7.3 Hz, 2H), 4.00 (s, 1H), 3.97 (s, 1H), 1.49 (br. s, 9H), 1.25 (t, J=7.2 Hz, 3H).

Step 5: 2-Bromo-8-hydroxyimidazo[1,2-b] pyridazine-7-carboxylic acid

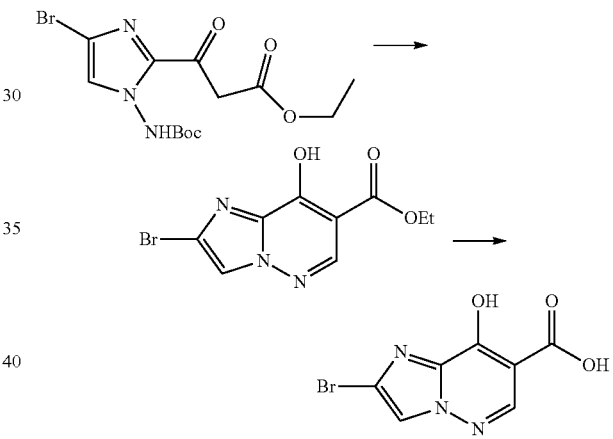

To a solution of ethyl 3-(4-bromo-1-((tert-butoxycarbonyl)amino)-1H-imidazol-2-yl)-3-oxopropanoate (1.354 g, 3.60 mmol) in DCM (23.99 ml) at room temperature was added DMF-DMA (1.446 ml, 10.80 mmol). The reaction was stirred at room temperature for 3 h. The resulting yellow suspension was concentrated under reduced pressure to give the crude cyclization product as a yellow oil. A small amount of material was triturated in CH$_3$CN to give a pure sample of ethyl 2-bromo-8-hydroxyimidazo[1,2-b]pyridazine-7-carboxylate as a white solid. LCMS (Method B) m/z 288.0 [M+1], Br-pattern; $^1$H NMR (400 MHz, MeOD) δ 8.39 (s, 1H), 7.62 (s, 1H), 4.27 (q, J=7.1 Hz, 2H), 1.34 (t, J=7.0 Hz, 3H).

The yellow oil was taken into ethanol (12.00 ml). A 7.0 N aqueous solution of potassium hydroxide (3.60 ml, 25.2 mmol) was added dropwise. The reaction was heated at 90° C. for 1 h. After being cooled to room temperature, the reaction was concentrated to yield an oil. The oil was partitioned between ethyl acetate and water. The aqueous layer was acidified with 1.0 N HCl, forming a white precipitate. The precipitated solid was collected by filtration, rinsed with ice-cold water and dried under vacuum to afford 2-bromo-8-hydroxyimidazo[1,2-b]pyridazine-7-carboxylic acid (0.610 g, 2.364 mmol, 65.7% yield for 2 steps). LCMS (Method B): 258.0 [M+1], Br pattern. HPLC (Method B): Rt 1.847 min (10-90% aq CH$_3$OH/0.2% H3PO4, 4.0 min. gradient w/1 min. hold. Column: YMC COMBISCREEN® ODS-A. 4.0 mL/min. flow rate, 220 nm detection wavelength); $^1$H NMR (400 MHz, DMSO-d$_6$) δ 8.26 (s, 1H), 8.01 (s, 1H).

Step 6: 2-Bromo-8-chloroimidazo[1,2-b]pyridazine-7-carboxamide (Intermediate 1)

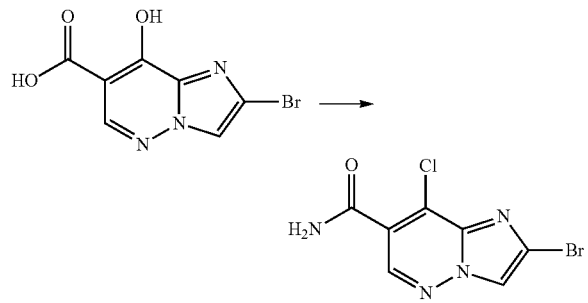

To a round-bottom flask charged with 2-bromo-8-hydroxyimidazo[1,2-b]pyridazine-7-carboxylic acid (55 g, 213 mmol) and POCl$_3$ (990 mL, 10.64 mol) at room temperature under nitrogen was added DIPEA (37.2 mL, 213 mmol). The reaction was heated at 120° C. for 3 hrs. The resulting clear solution was cooled to room temperature and concentrated to remove excess phosphorus oxychloride. The residue was dissolved in 100 ml of THF and was concentrated. The process was repeated two more times to give crude methyl 2-bromo-8-chloroimidazo[1,2-b]pyridazine-7-carboxylate as a brown viscous solid. The solid was taken up in 400 ml THF and cooled to −40° C. A saturated ammonia solution in THF (200 ml) at −40° C. was added dropwise. After completion of addition, the reaction was stirred at −40° C. for 15 minutes, the cooling bath was removed. The reaction was stirred at room temperature for 20 min and concentrated under reduced pressure. 700 ml of water was added and the suspension was stirred for 5 minutes and filtered. The filter cake was washed with 200 ml of water and 200 ml of MTBE to afford 2-bromo-8-chloroimidazo[1,2-b]pyridazine-7-carboxamide as a pale yellow solid (41.2 g, 149 mmol, 70% yield). LCMS (Method B): m/z 276.9, 278.9 [M+1]; HPLC (Method B): Rt 0.935 min (10-90% aq CH$_3$OH/0.2% H3PO4, 4.0 min. gradient w/1 min. hold. Column: YMC COMBISCREEN® ODS-A. 4.0 mL/min. flow rate, 220 nm detection wavelength); $^1$H NMR (400 MHz, DMSO-d$_6$) δ 8.73 (s, 1H), 8.64 (s, 1H), 8.18 (br. s., 1H), 8.06 (br. s., 1H).

Intermediate 2

(3S,4S)-Benzyl 3-amino-4-methylpyrrolidine-1-carboxylate

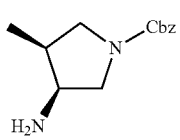 [SMILES: C[C@H]1CN(C(=O)OCc2ccccc2)C[C@H]1N]

Step 1: Benzyl 6-oxa-3-azabicyclo[3.1.0]hexane-3-carboxylate

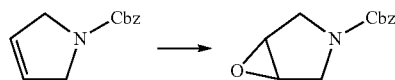 [SMILES: O=C(OCc1ccccc1)N1CC=CC1 ; O=C(OCc1ccccc1)N1CC2OC2C1]

To a 1 L RB flask equipped with magnetic stirring bar was added benzyl 2,5-dihydro-1H-pyrrole-1-carboxylate (25 g, 123 mmol) and CH$_2$Cl$_2$ (246 ml). The resulting solution was cooled in an ice bath to 0° C., whereupon mCPBA (42.5 g, 246 mmol) was added in three portions over ~15 min. The resulting slurry was naturally warmed up to rt over 2 days. LCMS indicates a complete reaction. The reaction was worked up as follows: the heterogeneous mixture was cooled to −15° C. for 1 hour, filtered to remove the solid which was rinsed with cold DCM. The resulting filtrate was washed with 1N aq. NaOH (4×100 mL), water (100 mL) and brine, then dried with anhydrous sodium sulfate. DCM phase was concentrated to benzyl 6-oxa-3-azabicyclo[3.1.0]hexane-3-carboxylate (24.5 g, 91% yield) as light yellow oil. $^1$H NMR (400 MHz, chloroform-d) δ ppm 7.31-7.44 (5H, m), 5.08-5.21 (2H, m), 3.90 (2H, dd, J=19.70, 12.65 Hz), 3.65-3.77 (2H, m), 3.42 (2H, ddd, J=12.76, 6.16, 1.10 Hz); LCMS (CHROMOLITH® RP-18e 2.0×50 mm, 0.8 mL/min, Solvent A: 10% MeOH/water with 0.1% TFA, Solvent B: 90% MeOH/water with 0.1% TFA, gradient with 0-100% B over 4 minutes) retention time: 2.41 min; MS(ES+) m/z: 242.0 (M+Na$^+$).

Step 2: (3R,4S)-Benzyl 3-hydroxy-4-methylpyrrolidine-1-carboxylate

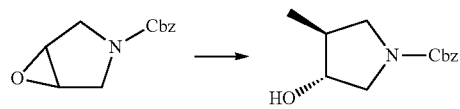 [SMILES: O=C(OCc1ccccc1)N1CC2OC2C1 ; C[C@H]1CN(C(=O)OCc2ccccc2)C[C@@H]1O]

3M methylmagnesium bromide in ether (99 ml, 296 mmol) was added dropwise over 1 hour to a suspension of benzyl 6-oxa-3-azabicyclo[3.1.0]hexane-3-carboxylate (26 g, 119 mmol) and copper bromide-dimethyl sulfide complex (24.38 g, 119 mmol) in anhydrous THF (250 ml) at −40° C. under a nitrogen atmosphere. The reaction was allowed to stir at this temperature for an additional 1 hour before cautiously quenching of the reaction using 125 mL sat. ammonium chloride. The reaction was then allowed to warm to rt and diluted with water (125 mL), then extracted with ethyl acetate (3×150 mL). Ethyl acetate phases were combined, washed with brine, then dried with Na$_2$SO$_4$. After concentration, the crude material was purified by flash chromatography. (+/−)-Benzyl 3-hydroxy-4-methylpyrrolidine-1-carboxylate (24.5 g, 104 mmol, 88% yield) was obtained as light yellow oil. $^1$H NMR (400 MHz, chloroform-d) δ ppm 7.28-7.46 (5H, m), 5.14 (2H, s), 3.93-4.05 (1H, m), 3.63-3.78 (2H, m), 3.25-3.43 (1H, m), 3.12 (1H, ddd, J=13.26, 10. This material was resolved using the following chiral SFC conditions: column: CHIRALPAK® AD-H 5×25 cm, 5 μm, Column Temp. 40° C., Flow rate: 290 mL/min, Mobile Phase: CO$_2$/MeOH=82/18, injection volume: 2.5 mL (Conc. 118 mg/mL), detector wavelength: 212 nm. The isolated isomers were named "Pk1" and "Pk2" in the elution order. Fractions containing Pk2 were concentrated to afford 10 g of (3R,4S)-benzyl 3-hydroxy-4-methylpyrrolidine-1-carboxylate as a yellow oil. 84, 5.17 Hz), 2.06-2.26 (1H, m), 1.90 (1H, d, J=8.36 Hz), 1.03 (3H, dd, J=6.71, 5.39 Hz); LCMS (CHROMOLITH® RP-18e 2.0×50 mm, 0.8 mL/min, Solvent A: 10% MeOH/water with 0.1% TFA, Solvent B: 90% MeOH/water with 0.1% TFA, gradient with 0-100% B over 4 minutes) retention time: 2.56 min; MS(ES+) m/z: 236.0 (M+H$^+$); HPLC retention time: 3.028 min (analytical HPLC Method H). Chiral purity: 99.9% ee (chiral HPLC conditions: column: CHIRALPAK® AD-H (25×0.46 cm, 5 μm), 30% MeOH in CO$_2$, 3 mL/min, 40° C., 200-400 nm, 100 bars).

Step 3: (3S,4R)-Benzyl
3-methyl-4-(tosyloxy)pyrrolidine-1-carboxylate

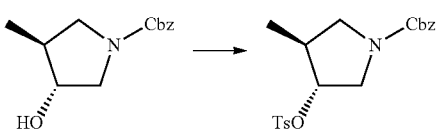 [SMILES: C[C@H]1CN(C(=O)OCc2ccccc2)C[C@@H]1O ; Cc1ccc(S(=O)(=O)O[C@H]2CN(C(=O)OCc3ccccc3)C[C@@H]2C)cc1]

(3R,4S)-Benzyl 3-hydroxy-4-methylpyrrolidine-1-carboxylate (19.6 g, 83 mmol) was dissolved in pyridine (83 ml). To the above solution, Ts-Cl (22.2 g, 117 mmol) was added in portions at rt. After overnight stirring, the reaction mixture was concentrated in vacuo to remove pyridine. The residue was quenched with ice water (200 mL), extracted with ethyl acetate (3×150 mL). The combined ethyl acetate phase was washed with water, 1N HCl, water and sat. NaHCO$_3$, then dried with Na$_2$SO$_4$. After concentration, (3S,4R)-benzyl 3-methyl-4-(tosyloxy)pyrrolidine-1-carboxylate (30 g, 92% yield) was obtained as light yellow oil. $^1$H NMR (400 MHz, chloroform-d) δ ppm 7.76-7.83 (2H, m), 7.30-7.40 (7H, m), 5.11 (2H, s), 4.57-4.64 (1H, m), 3.56-3.73 (2H, m), 3.38-3.54 (1H, m), 3.08-3.19 (1H, m), 2.33-2.55 (4H, m), 0.97 (3H, dd, J=14.86, 7.15 Hz); LCMS (CHROMOLITH® RP-18e 2.0×50 mm, 0.8 mL/min, Solvent A: 10% MeOH/water with 0.1% TFA, Solvent B: 90% MeOH/water with 0.1% TFA, gradient with 0-100% B over 4 minutes) retention time: 3.60 min; MS(ES+) m/z: 390 (M+H$^+$).

Step 4: (3S,4S)-Benzyl
3-azido-4-methylpyrrolidine-1-carboxylate

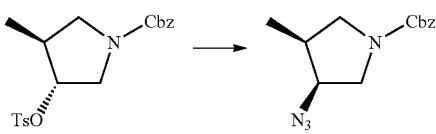

(3S,4R)-Benzyl 3-methyl-4-(tosyloxy)pyrrolidine-1-carboxylate (20 g, 51.4 mmol) was dissolved in DMF (42.8 ml). Sodium azide (5.68 g, 87 mmol) was added at rt and heated up to 85° C. overnight. LCMS shows a complete conversion. The reaction mixture was cooled to rt, quenched with ice water, extracted with ethyl acetate. Organic phases were combined, washed with water, brine, then dried with Na$_2$SO$_4$. After concentration, (3S,4S)-benzyl 3-azido-4-methylpyrrolidine-1-carboxylate (13 g, 97% yield) was obtained as a yellowish oil and used directly for the next reduction. $^1$H NMR (400 MHz, chloroform-d) δ ppm 7.29-7.44 (5H, m), 5.08-5.22 (2H, m), 3.94-4.04 (1H, m), 3.52-3.76 (3H, m), 3.00-3.15 (1H, m), 2.29-2.48 (1H, m), 1.13 (3H, t, J=7.04 Hz); LCMS (CHROMOLITH® RP-18e 2.0× 50 mm, 0.8 mL/min, Solvent A: 10% MeOH/water with 0.1% TFA, Solvent B: 90% MeOH/water with 0.1% TFA, gradient with 0-100% B over 4 minutes) retention time: 3.41 min; MS(ES+) m/z: 261.0 (M+H$^+$).

Step 5: (3S,4S)-Benzyl
3-amino-4-methylpyrrolidine-1-carboxylate
(Intermediate 2)

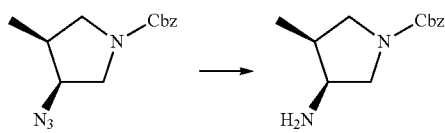 [SMILES: C[C@H]1CN(C(=O)OCc2ccccc2)C[C@H]1N=[N+]=[N-] ; C[C@H]1CN(C(=O)OCc2ccccc2)C[C@H]1N]

Triphenylphosphine (11.96 g, 45.6 mmol) was added to a stirred acetonitrile (164 ml) and water (16.44 ml) solution of benzyl 3-azido-4-methylpyrrolidine-1-carboxylate (11.3 g, 43.4 mmol). The reaction mixture was heated up to 60° C. overnight. The reaction mixture was concentrated. The resulting residue was diluted with 50 mL ice water, treated with 1N HCl (47.8 ml, 47.8 mmol). The aqueous acidic solution (pH 1) was extracted with EtOAc (4×100 mL) to remove Ph$_3$P and Ph$_3$PO by-products/impurities. The acidic aqueous portion containing the product was cooled in an ice bath, neutralized with 1N NaOH (52.1 ml, 52.1 mmol). The resulting cloudy mixture was then extracted with DCM (3×150 mL). The combined DCM phases were washed with brine, dried over anhydrous sodium sulfate. After concentration, (3S,4S)-benzyl 3-amino-4-methylpyrrolidine-1-carboxylate (9.8 g, 96% yield) was obtained as a light yellow oil. $^1$H NMR (400 MHz, chloroform-d) δ ppm 7.31-7.47 (5H, m), 5.09-5.23 (2H, m), 3.42-3.69 (3H, m), 3.12-3.38 (2H, m), 2.17-2.36 (1H, m), 1.31 (2H, br), 1.06 (3H, dd, J=6.82, 3.30 Hz); LCMS (CHROMOLITH® RP-18e 2.0×50 mm, 0.8 mL/min, Solvent A: 10% MeOH/water with 0.1% TFA, Solvent B: 90% MeOH/water with 0.1% TFA, gradient with 0-100% B over 4 minutes) retention time: 1.97 min; MS(ES+) m/z: 235.1 (M+H$^+$).

Intermediate 3

(3S,4S)-Benzyl
3-amino-4-ethylpyrrolidine-1-carboxylate

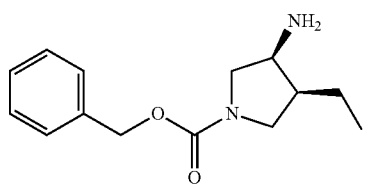 [SMILES: CC[C@H]1CN(C(=O)OCc2ccccc2)C[C@H]1N]

Step 1: (3S,4R)-Benzyl 3-ethyl-4-hydroxypyrrolidine-1-carboxylate

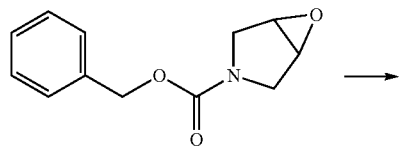

A mixture of benzyl 6-oxa-3-azabicyclo[3.1.0]hexane-3-carboxylate (4 g, 18.25 mmol) and bromo(dimethylsulfide)copper(I) (3.75 g, 18.25 mmol) in tetrahydrofuran (40 ml) was cooled to −30° C. A 3M solution of ethylmagnesium bromide (15.20 ml, 45.6 mmol) in Et$_2$O was added dropwise to the reaction mixture over 35 minutes, maintaining an internal temperature of at or below −30° C. After the addition was complete, the resulting reaction mixture was allowed to warm to −15° C. over 45 minutes. At this time, the reaction was checked by HPLC. The reaction mixture was allowed to gradually warm up to rt and HPLC indicated that the reaction was complete. The reaction mixture was diluted with EtOAc (50 mL). The reaction mixture was then cooled in an ice bath and was quenched by slow addition of sat'd aq. ammonium chloride (~10 mL). The organic layer was separated and was washed with H$_2$O (20 ml). The organic layer was concentrated and the crude was purified by silica gel chromatography to give (3S,4R)-benzyl 3-ethyl-4-hydroxypyrrolidine-1-carboxylate (17.25 g, 69.2 mmol, 69.0% yield). LCMS: (M+23)=242, t=1.87 min.

Step 2: (3S,4R)-Benzyl 3-ethyl-4-(tosyloxy)pyrrolidine-1-carboxylate

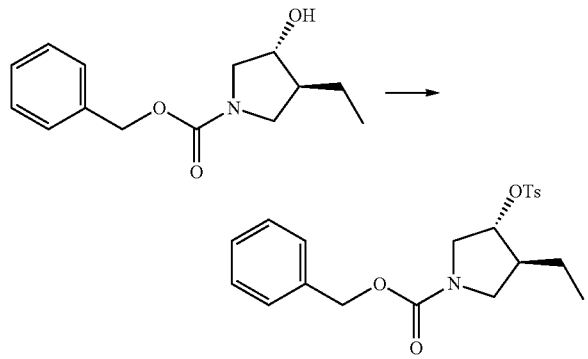

(3S,4R)-Benzyl 3-ethyl-4-hydroxypyrrolidine-1-carboxylate (18.9 g, 76 mmol), 4-methylbenzene-1-sulfonyl chloride (21.68 g, 114 mmol) were dissolved in DCM (100 mL) and cooled in an ice bath. Added N,N-dimethylpyridin-4-amine (1.852 g, 15.16 mmol) and triethylamine (11.51 g, 114 mmol) and let the reaction mixture warm to RT overnight. The suspension was passed over a silica column and eluted with heptanes/EA (9:1 to 4:1 mixtures) to give (3S,4R)-benzyl 3-ethyl-4-(tosyloxy)pyrrolidine-1-carboxylate (28.7 g, 71.1 mmol, 94% yield). LCMS: M+1=404, t=3.07 min.

Step 3: (3R,4S)-Benzyl 3-azido-4-ethylpyrrolidine-1-carboxylate

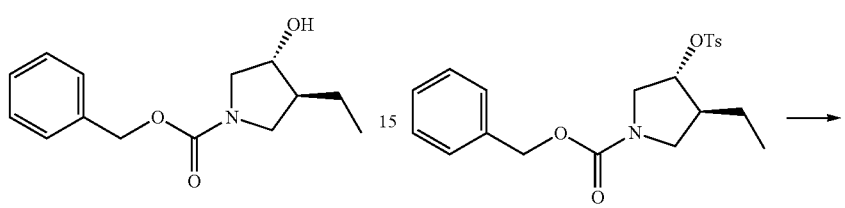

(3S,4R)-Benzyl 3-ethyl-4-(tosyloxy)pyrrolidine-1-carboxylate (21.25 g, 52.7 mmol) in DMF (50 mL) was added to a solution of sodium azide (8.56 g, 132 mmol) in DMF (50 mL) and water (30 mL) and heated to a bath temp. of 100° C. overnight. The reaction mixture was diluted with ethyl acetate/water and stirred. The organic layer was washed with water, dried (Na$_2$SO$_4$) and concentrated to give (3S,4S)-benzyl 3-azido-4-ethylpyrrolidine-1-carboxylate (14.5 g, 52.9 mmol, 100% yield). $^1$H NMR (400 MHz, chloroform-d) δ ppm 7.34-7.41 (5H, m), 5.13-5.21 (2H, m), 4.08-4.11 (1H, m), LCMS: M+23=299, t=2.15 min.

Step 4: (3S,4S)-Benzyl 3-amino-4-ethylpyrrolidine-1-carboxylate (Intermediate 3)

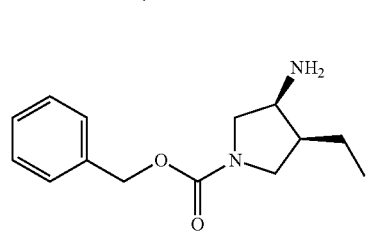

(3S,4S)-Benzyl 3-azido-4-ethylpyrrolidine-1-carboxylate (14.0 g, 51.0 mmol) was dissolved in acetonitrile (200 mL). Added water (20 mL) and stirred at RT to a clear solution. This soln. was warmed to 60° C. for 6.5 hrs. Acetonitrile was removed in vacuo and residual aqueous portion was diluted with 1N HCl (100 mL) which was washed with ethyl acetate (5×50 mL) until all Ph₃P and Ph₃P oxide was removed from the aqueous portion. The aqueous portion which contains HCl salt of the amine was cooled to ~5 deg. This acidic soln was made basic (pH 12) with 1N NaOH. Extracted this basic milky suspension with DCM (5×, 50 mL), dried (Na₂SO₄) and concentrated. On vacuum overnight gave (3S,4S)-benzyl 3-amino-4-ethylpyrrolidine-1-carboxylate (11.01 g, 44.3 mmol, 87% yield). LCMS: M+1=249, t=1.39 min. This material was resolved using the following chiral SFC conditions [column: CHIRALPAK® AD-H 5×25 cm, 5 µm, Column Temp. 48° C., Flow rate: 290 mL/min, Mobile Phase: CO₂/MeOH=77/23 with 0.3% triethylamine, injection volume: 3 mL (Conc. 68.8 mg/mL), detector wavelength: 215 nm, 100 bars]. The isolated isomers were named "Pk1" and "Pk2" in the elution order. Fractions containing Pk1 were concentrated to afford 5.1 g of the desired (3S, 4S)-benzyl 3-amino-4-ethylpyrrolidine-1-carboxylate (Intermediate 9). Chiral purity: >99% ee (chiral HPLC conditions: column: CHIRALPAK® AD-H (25×0.46 cm, 5 µm), 30% MeOH in CO₂ with 0.3% triethylamine, 3 mL/min, 40° C., 200-400 nm, 100 bars). ¹H NMR (400 MHz, chloroform-d) δ ppm 7.33-7.42 (5H, m), 5.12-5.17 (2H, m), 3.51-3.67 (3H, m), 3.32-3.40 (1H, m), 3.14-3.21 (1H, m), 2.0-2.15 (1H, m), 1.44-1.55 (2H, m), 0.97-1.02 (5H, m). LCMS: (M+1)=249, t=1.39 min.

Intermediate 4

(R)-tert-Butyl 4-amino-3,3-dimethylpiperidine-1-carboxylate

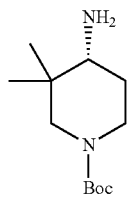 [SMILES: CC(C)(C)OC(=O)N1CC[C@@H](N)C(C)(C)C1]

Step 1: (R,E)-tert-Butyl 3,3-dimethyl-4-(1-phenylethylimino)piperidine-1-carboxylate

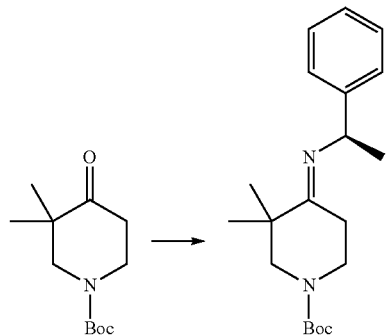 [SMILES: CC(C)(C)OC(=O)N1CCC(=O)C(C)(C)C1 ; C[C@@H](/N=C1\CCN(C(=O)OC(C)(C)C)CC1(C)C)c1ccccc1]

A solution of (R)-1-phenylethanamine (2.56 g, 21.12 mmol) and triethylamine (14.7 mL, 106 mmol) in dichloromethane (40 mL) was cooled in an ice bath and titanium tetrachloride (8.80 mL, 8.80 mmol) was added dropwise giving a light brown mixture. The cold bath was removed and tert-butyl 3,3-dimethyl-4-oxopiperidine-1-carboxylate (4.00 g, 17.60 mmol) was added as solid in one portion and the resulting mixture was allowed to stir at rt overnight. To the resulting mixture was added 75 mL of diethyl ether and the mixture was stirred at rt for 15 min then filtered through a pad of CELITE® to remove the solids and the filter cake was rinsed with additional ether (30 mL×2). The resulting clear yellow filtrate was concentrated on a rotovap to afford a yellow liquid as the title compound (5.80 g, 17.6 mmol, quantitative). This material was used directly without any further purification.

Step 2: (R)-tert-Butyl 3,3-dimethyl-4-((R)-1-phenylethylamino)piperidine-1-carboxylate

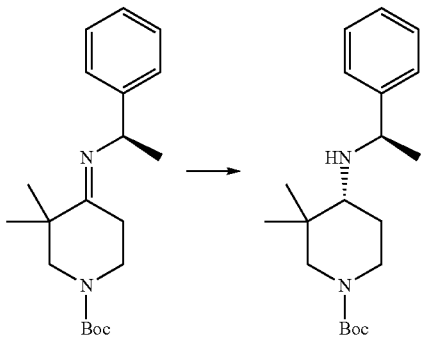 [SMILES: C[C@@H](/N=C1\CCN(C(=O)OC(C)(C)C)CC1(C)C)c1ccccc1 ; C[C@@H](N[C@@H]1CCN(C(=O)OC(C)(C)C)CC1(C)C)c1ccccc1]

Dissolved (R,E)-tert-butyl 3,3-dimethyl-4-(1-phenylethylimino)piperidine-1-carboxylate (5.80 g, 17.55 mmol) in ethanol (50 mL) and cooled to −78° C. then added sodium borohydride (0.332 g, 8.78 mmol) and let resulting mixture stir at −78° C. for 2 h. Then the mixture was cooled 2 N aq HCl (10 mL) was added dropwise slowly and the resulting mixture was allowed to stir vigorously for 30 min. The mixture was cooled and made basic by addition of 10% aq sodium carbonate and then concentrated to remove most of the ethanol. The resulting aqueous portion was extracted with EtOAc (3×100 mL) and the combined extracts were washed with brine, dried over anhyd. sodium sulfate, decanted and concentrated under vacuum to afford a yellow liquid as the crude product. This material was purified via preparative ISCO chromatography (hex/EtOAc; 120 g silica gel column) and the fractions containing the major product were concentrated to afford the title compound as a near colorless oil (3.0 g, 9.0 mmol, 51%). HPLC (Method B) retention time=2.25 min. LCMS (m+1)=333.2. ¹H NMR (500 MHz, MeOD): δ ppm 7.31-7.42 (4H, m), 7.22-7.29 (1H, m), 3.88-3.98 (1H, m), 3.83 (1H, q, J=6.66 Hz), 3.63-3.72 (1H, m), 2.49-2.85 (2H, m), 2.34 (1H, dd, J=10.82, 4.16 Hz), 1.47 (9H, s), 1.36 (3H, d, J=6.66 Hz), 1.22-1.33 (2H, m), 1.05 (3H, s), 0.90 (3H, s). Fractions containing a minor product believed to be the minor diastereomer were also concentrated to afford a clear oil. HPLC (Method B) retention time=2.50 min. LCMS (m+1)=333.2.

Step 3: (R)-tert-Butyl 4-amino-3,3-dimethylpiperidine-1-carboxylate (Intermediate 4)

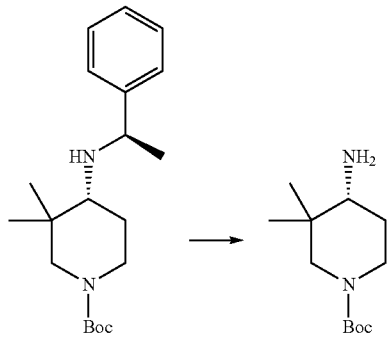 [SMILES: C[C@@H](N[C@@H]1CCN(C(=O)OC(C)(C)C)CC1(C)C)c1ccccc1 ; CC(C)(C)OC(=O)N1CC[C@@H](N)C(C)(C)C1]

A pressure bottle was charged with palladium on carbon (0.192 g, 0.180 mmol) and (R)-tert-butyl 3,3-dimethyl-4-((R)-1-phenylethylamino)piperidine-1-carboxylate (3.00 g, 9.02 mmol) in ethanol (60 mL) and the resulting mixture was shaken under 50 psi of hydrogen on a Parr apparatus. After 5 h, the catalyst was removed by filtration, rinsed with methanol, and the filtrate was concentrated in vacuo to afford the title compound as a clear oil (2.0 g, 8.76 mmol, 97%). Material was not further purified and was used directly in next transformation. $^1$H NMR (500 MHz, methanol-$d_4$) δ 4.07 (d, J=13.0 Hz, 1H), 3.78-3.62 (m, 1H), 3.01-2.62 (m, 2H), 2.56 (dd, J=11.1, 4.2 Hz, 1H), 1.74-1.63 (m, 1H), 1.51 (s, 9H), 1.49-1.43 (m, 1H), 1.00 (s, 3H), 0.88 (s, 3H).

Intermediate 5

(3R,4R)-tert-Butyl 4-amino-3-ethylpiperidine-1-carboxylate

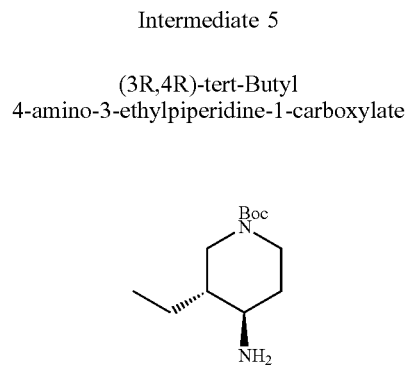

Step 1: Benzylpiperidin-4-ylidene)-1-phenylethanamine

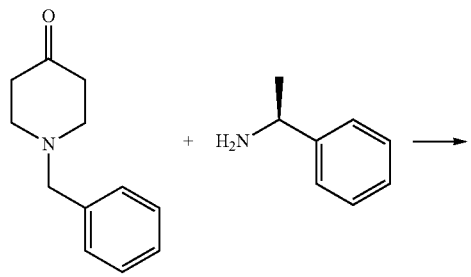

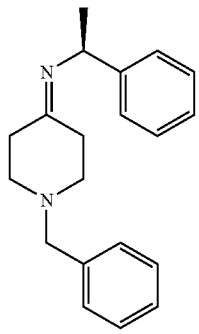

To a solution of (S)-1-phenylethanamine (1.921 g, 15.85 mmol) in benzene (8.81 ml) were added molecular sieves in water and 1-benzylpiperidin-4-one (2.50 g, 13.21 mmol). The reaction was stirred at room temperature for 5 hrs. The product mixture was filtered and concentrated under reduced pressure to give a yellow oil, which was standing under vacuum at 45° C. for 14 hrs to remove the residual reactant, yielding (S)—N-(1-benzylpiperidin-4-ylidene)-1-phenylethanamine (3.24 g, 11.08 mmol, 84.0% yield) as a yellow oil. $^1$H NMR (400 MHz, methanol-$d_4$) δ 7.33-7.25 (m, 10H), 4.81-4.76 (m, 1H), 3.54 (s, 2H), 2.72-2.33 (m, 8H), 1.47 (d, J=6.6 Hz, 3H). LCMS (Method E) m/z 291.3 ([M+H]$^+$).

Step 2: (3R,4R)-1-Benzyl-3-ethyl-N—((S)-1-phenylethyl)piperidin-4-amine

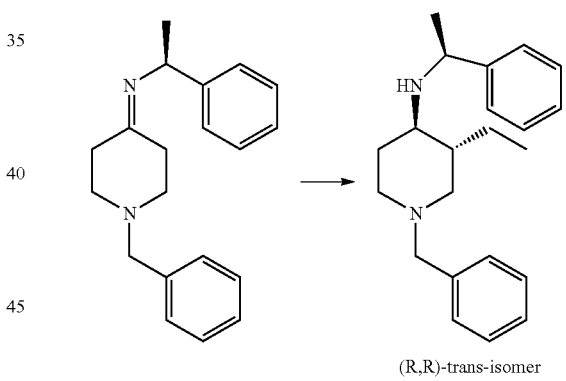

(R,R)-trans-isomer

To a solution of LDA (7.20 ml, 14.40 mmol) in THF (22.16 ml) cooled to −10° C. was added a THF (5 ml) solution of (S)—N-(1-benzylpiperidin-4-ylidene)-1-phenylethanamine (3.24 g, 11.08 mmol). The reaction was stirred for 30 minutes. Ethyl iodide (1.164 ml, 14.40 mmol) was added, and stirring was continued for 1 hr. The reaction solution was cooled to −78° C. Ethanol (22.16 ml) and sodium borohydride (0.545 g, 14.40 mmol) were added. Stirring was continued for 15 minutes. The reaction flask was transferred to a −10° C. bath and stirring was continued for 1 hr. The reaction was allowed to warm to room temperature, concentrated to half volume and quenched by dropwise addition of 6.0 N HCl until gas evolution ceased. The solution was diluted with water (10 ml), adjusted to pH 12 with 6.0 N NaOH, and extracted with ethyl acetate (3×, 100 ml). The combined ethyl acetate extracts were dried with sodium sulfate, filtered, and concentrated to give a yellow oil. The crude product mixture was purified via medium pressure chromatography (silica gel column, EtOAc/hexanes eluent, 40-100% gradient elution). The 40% EtOAc/hexanes fraction yielded two cis-isomers, the fast eluting isomer (499.3 mg, 14.0% yield) and the slow eluting isomer (319.1 mg, 8.9% yield). The 100% EtOAc fraction yielded a single trans-isomer, (3R,4R)-1-benzyl-3-ethyl-N—((S)-1-phenylethyl)piperidin-4-amine (679.2 mg, 2.106 mmol, 19.0% yield) as a colorless oil. LCMS (Method E) m/z 323.4 ([M+H]$^+$).

Step 3: (3R,4R)-3-Ethyl-N—((S)-1-phenylethyl)piperidin-4-amine

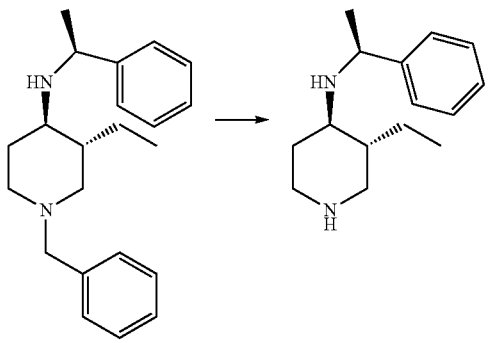 [SMILES: CC[C@@H]1CN(Cc2ccccc2)CC[C@H]1N[C@@H](C)c1ccccc1 ; CC[C@@H]1CNCC[C@H]1N[C@@H](C)c1ccccc1]

To a solution of (3R,4R)-1-benzyl-3-ethyl-N—((S)-1-phenylethyl)piperidin-4-amine (679.2 mg, 2.106 mmol) in 1,2-dichloroethane (3.50 ml) at 0° C. was added 1-chloroethyl chloroformate (0.276 ml, 2.53 mmol) dropwise. After stirring for 20 minutes, the ice-bath was removed and the reaction was heated to reflux for 1 hr. The reaction was cooled to room temperature and concentrated under reduced pressure. Methanol (10.5 ml) was added, and the reaction was heated to reflux for 2 hrs. After removal of the solvent, the residue was partitioned between ethyl acetate and water. The organic layer was washed with brine, dried with sodium sulfate, filtered, and concentrated under reduced pressure, yielding (3R,4R)-3-ethyl-N—((S)-1-phenylethyl)piperidin-4-amine (443 mg, 1.906 mmol, 91.0% yield) as a yellow oil. LCMS (Method E) m/z 233.3 ([M+H]$^+$).

Step 4: (3R,4R)-tert-Butyl 3-ethyl-4-(((S)-1-phenylethyl)amino)piperidine-1-carboxylate

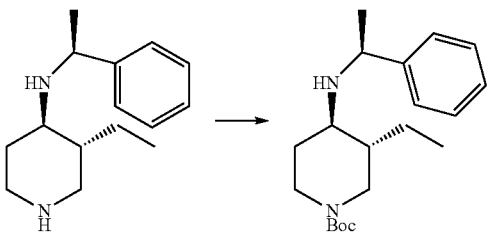 [SMILES: CC[C@@H]1CNCC[C@H]1N[C@@H](C)c1ccccc1 ; CC[C@@H]1CN(C(=O)OC(C)(C)C)CC[C@H]1N[C@@H](C)c1ccccc1]

To a solution of (3R,4R)-3-ethyl-N—((S)-1-phenylethyl)piperidin-4-amine (443 mg, 1.906 mmol) in dichloromethane (6.4 ml) were added diisopropylethylamine (832 μl, 4.77 mmol) and di-tert-butyl dicarbonate (664 μl, 2.86 mmol). The reaction was stirred at room temperature for 2 hrs. After removal of the solvent, the residue was partitioned between ethyl acetate and water. The organic layer was washed with brine, dried with sodium sulfate, filtered and concentrated under reduced pressure. The crude product was purified via medium pressure chromatography (silica gel column, EtOAc/hexanes eluent, 0-100% gradient elution) to yield (3R,4R)-tert-butyl 3-ethyl-4-(((S)-1-phenylethyl)amino)piperidine-1-carboxylate (430.5 mg, 1.295 mmol, 67.9% yield) as a white solid. LCMS (Method E) m/z 333.3 ([M+H]$^+$).

Step 5: (3R,4R)-tert-Butyl 4-amino-3-ethylpiperidine-1-carboxylate (Intermediate 5)

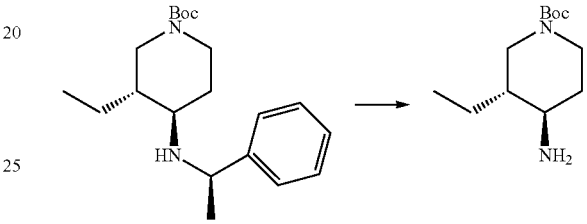

A flask was flushed with nitrogen and charged with 20% palladium hydroxide on carbon (91 mg, 0.647 mmol). A solution of (3R,4R)-tert-butyl 3-ethyl-4-(((R)-1-phenylethyl)amino)piperidine-1-carboxylate (430.5 mg, 1.295 mmol) in acetic acid (8.6 ml) was added. The flask was flushed with nitrogen, sealed, evacuated briefly, and charged with hydrogen. The mixture was stirred at room temperature for 14 hrs. The flask was evacuated, backfilled with nitrogen, and opened. The reaction mixture is filtered through CELITE®. The filtrate was concentrated by azeotropical distillation with toluene (3×25 ml) under reduced pressure to remove the residual acetic acid, yielding (3R,4R)-tert-Butyl 4-amino-3-ethylpiperidine-1-carboxylate, HOAc salt (351 mg, 1.217 mmol, 94.0% yield) as a white solid. $^1$H NMR (400 MHz, methanol-d$_4$) δ 4.16 (d, J=11.2 Hz, 1H), 4.07 (d, J=13.9 Hz, 1H), 3.03-2.85 (m, 2H), 2.56 (br. s., 1H), 2.02-1.94 (m, 1H), 1.92 (s, 3H), 1.77-1.66 (m, 1H), 1.53-1.36 (m, 10H), 1.32-1.16 (m, 1H), 1.00 (t, J=7.5 Hz, 3H).

Intermediate 6

(3S,4S)-Benzyl 3-amino-4-(fluoromethyl)pyrrolidine-1-carboxylate

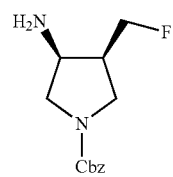

Step 1: 1-Benzyl 3-methyl 4-oxopyrrolidine-1,3-dicarboxylate

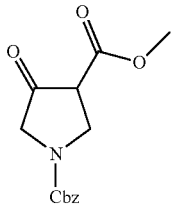 [SMILES: COC(=O)C1CN(C(=O)OCc2ccccc2)CC1=O]

A solution of carbobenzyloxyglycine methyl ester (10 g, 44.8 mmol) and methyl acrylate (4.03 mL, 44.8 mmol) in toluene (100 mL) at 0° C. was added 60% NaH in mineral oil (1.971 g, 49.3 mmol) which was stirred for 10 minutes, and then it was warmed up to RT and stirred for 20 minutes. The reaction mixture was heated to 50° C. for 3 hrs. The reaction mixture was quenched with 10% citric acid solution until pH about 3, and then it was extracted with 100 mL×3 of EtOAc. The combined organic phases were washed with 100 mL of brine and dried over Na$_2$SO$_4$. Filtration and concentration to yield the product (12 g, 96% yield). MS(ES+) m/z: 278.2 (M+H); HPLC retention time: 2.44 min (analytical HPLC Method B).

Step 2: 1-Benzyl 3-methyl 4-(methoxyimino)pyrrolidine-1,3-dicarboxylate

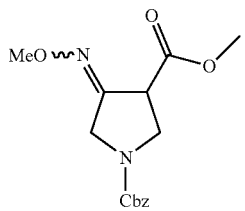 [SMILES: CON=C1CN(C(=O)OCc2ccccc2)CC1C(=O)OC]

A solution of 1-benzyl 3-methyl 4-oxopyrrolidine-1,3-dicarboxylate (12 g, 43.2 mmol) in pyridine (50 mL) at 0° C. was added O-methylhydroxylamine hydrochloride (5.51 g, 66.0 mmol) which was stirred for 10 minutes, and then it was warmed up to RT and stirred for 16 hrs. The reaction mixture was concentrated to yield a crude product which was partitioned in 300 mL of 1N HCl and 300 mL of EtOAc. The organic layer was washed with 100 mL of brine. The combined aqueous phases were extracted with 200 mL of EtOAc. The combined organic phases were dried over Na$_2$SO$_4$. Filtration and concentration to yield the product (12.6 g, 95% yield).

Step 3: (+/−)-Cis-benzyl 3-((tert-butoxycarbonyl)amino)-4-(hydroxymethyl)pyrrolidine-1-carboxylate

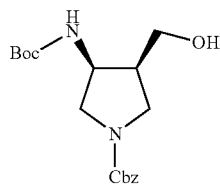 [SMILES: CC(C)(C)OC(=O)N[C@@H]1CN(C(=O)OCc2ccccc2)C[C@@H]1CO]

A solution of 1-benzyl 3-methyl 4-(methoxyimino)pyrrolidine-1,3-dicarboxylate (12.6 g, 41.1 mmol) in THF (100 mL) at −78° C. was added borane THF complex (1M in THF, 148 mL, 148 mmol) dropwise and stirred for 1.5 hrs, and then it was warmed to 0° C. and stirred for 2 hrs and further warmed up to RT and stirred for 16 hrs. The reaction was quenched with water at 0° C. until effervescence ceased, and to it was added K$_2$CO$_3$ (5.68 g, 41.1 mmol). The reaction mixture was warmed up to RT and stirred for 1 hr. (BOC)$_2$O (11.46 mL, 49.4 mmol) was added. The reaction mixture was stirred at RT for 16 hrs. The reaction mixture was added 200 mL of water and 500 mL of EtOAc and stirred for 10 minutes. The organic phase was separated and washed with 200 mL of brine, dried over Na$_2$SO$_4$, and then it was filtered, concentrated and purified by silica gel chromatography, eluting with 0-70% ethyl acetate in hexanes, to give the racemic title compound (5.46 g, 38% yield). $^1$H NMR (400 MHz, chloroform-d) δ 7.41-7.30 (m, 5H), 5.15 (d, J=1.3 Hz, 2H), 4.86-4.72 (m, 1H), 4.30 (br. s., 1H), 3.94-3.85 (m, 1H), 3.66 (dd, J=11.9, 5.1 Hz, 2H), 3.59-3.44 (m, 3H), 2.96 (q, J=11.4 Hz, 1H), 2.57 (br. s., 1H), 1.50-1.44 (m, 9H). MS(ES+) m/z: 351.1 (M+H); HPLC retention time: 2.79 min (analytical HPLC Method B).

Step 4: (+/−)-Cis-benzyl 3-(tert-butoxycarbonylamino)-4-(fluoromethyl)pyrrolidine-1-carboxylate

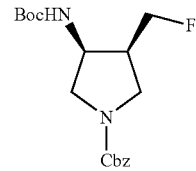

To a solution of (+/−)benzyl 3-((tert-butoxycarbonyl)amino)-4-(hydroxymethyl)pyrrolidine-1-carboxylate (4.70 g, 13.41 mmol) and Et$_3$N (2.52 mL, 18.11 mmol) in dichloromethane (100 mL) was added methanesulfonyl chloride (1.254 mL, 16.10 mmol) dropwise at 0° C. and the resulting mixture was stirred at RT for 1 hr. The reaction mixture was diluted with 50 mL of CH$_2$Cl$_2$ and then washed with 50 mL of 10% citric acid solution, 50 mL of brine and dried over Na$_2$SO$_4$. Filtration and concentration yielded the crude mesylate intermediate which was used directly in next transformation without any further purification. MS(ES+) m/z: 429.1 (M+H); HPLC retention time: 2.836 min (analytical HPLC Method H). To a solution of (+/−)-benzyl 3-((tert-butoxycarbonyl)amino)-4-(((methylsulfonyl)oxy)methyl) pyrrolidine-1-carboxylate (5.75 g, 13.41 mmol) in THF (50 mL) was added TBAF (1M in THF, 30.8 mL, 30.8 mmol) at 0° C. followed by warming to rt and stirring for 16 hrs. The reaction mixture was then heated to 55° C. for 5 hrs before cooling and concentrating to yield the crude fluoro intermediate. To this material was added 150 mL of water and the resulting mixture was extracted with 200 mL×2 of EtOAc. The combined organic phases were washed with 200 mL of brine and dried over Na$_2$SO$_4$, filtered, concentrated and purified by silica gel chromatography, eluting with 0-50% ethyl acetate in hexanes, to give the title compound (2.307 g, 49% yield). $^1$H NMR (400 MHz, chloroform-d) δ 7.42-7.31 (m, 5H), 5.16 (d, J=2.6 Hz, 2H), 4.85-4.67 (m, 1H), 4.66-4.55 (m, 1H), 4.54-4.32 (m, 1H), 3.79-3.64 (m, 2H), 3.49-3.28 (m, 2H), 2.79-2.56 (m, 1H), 1.47 (s, 9H).

MS(ES+) m/z: 353.1 (M+H); HPLC retention time: 3.008 min (analytical HPLC Method B).

Step 5: (3S,4S)-Benzyl 3-(tert-butoxycarbonylamino)-4-(fluoromethyl)pyrrolidine-1-carboxylate and (3R,4R)-Benzyl 3-(tert-butoxycarbonylamino)-4-(fluoromethyl)pyrrolidine-1-carboxylate

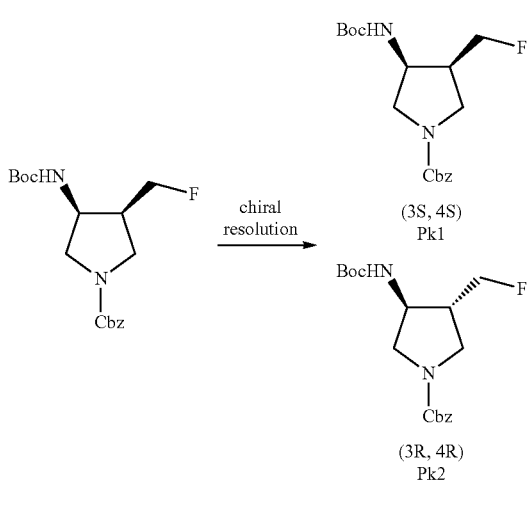 [SMILES: CC(C)(C)OC(=O)N[C@@H]1CN(C(=O)OCc2ccccc2)C[C@@H]1CF ; CC(C)(C)OC(=O)N[C@@H]1CN(C(=O)OCc2ccccc2)C[C@@H]1CF ; CC(C)(C)OC(=O)N[C@@H]1CN(C(=O)OCc2ccccc2)C[C@H]1CF]

(+/−)Benzyl 3-((tert-butoxycarbonyl)amino)-4-(fluoromethyl)pyrrolidine-1-carboxylate (2.307 g, 6.55 mmol) was separated under the following chiral SFC conditions: column: CHIRALPAK® AD-H 25×3 cm, 5 μm, Column Temp. 45° C., Flow rate: 150 mL/min, Mobile Phase: CO$_2$/MeOH=65/35, injection volume: 1.5 mL (Conc. 50 mg/mL), detector wavelength: 220 nm. The isolated isomers were named "Pk1" and "Pk2" in the elution order. The Pk1 was collected as the desired (3S,4S)-enantiomeric product (1.012 g, 44% yield). $^1$H NMR (500 MHz, chloroform-d) δ 7.43-7.31 (m, 5H), 5.16 (d, J=4.2 Hz, 2H), 4.87-4.66 (m, 1H), 4.65-4.34 (m, 2H), 3.80-3.66 (m, 2H), 3.48-3.27 (m, 2H), 2.77-2.60 (m, 1H), 1.47 (s, 9H). MS(ES+) m/z: 353.1 (M+H); HPLC retention time: 3.028 min (analytical HPLC Method B). Chiral purity: 99.9% ee (chiral HPLC conditions: column: CHIRALPAK® AD-H (25×0.46 cm, 5 μm), 35% MeOH in CO$_2$, 3 mL/min, 45° C., 220 nm, 100 bar).

Step 6: (3S,4S)-Benzyl 3-amino-4-(fluoromethyl)pyrrolidine-1-carboxylate (Intermediate 6)

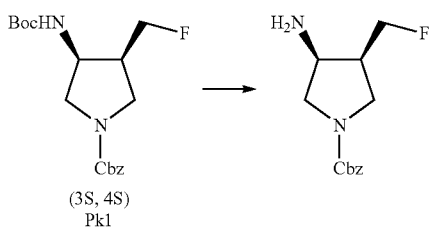 [SMILES: CC(C)(C)OC(=O)N[C@@H]1CN(C(=O)OCc2ccccc2)C[C@@H]1CF ; N[C@@H]1CN(C(=O)OCc2ccccc2)C[C@@H]1CF]

A solution of (3S,4S)-benzyl 3-((tert-butoxycarbonyl) amino)-4-(fluoromethyl)pyrrolidine-1-carboxylate (Pk1) (1.012 g, 2.87 mmol) in CH$_2$Cl$_2$ (10 mL) at 0° C. was added TFA (2.212 mL, 28.7 mmol) and the resulting mixture was allowed to warm to rt and stir for 1 hr. The reaction mixture was concentrated and redissolved in 70 mL of CH$_2$Cl$_2$ and was washed with 20 mL of 2M Na$_2$CO$_3$ solution and 20 mL of brine then dried over Na$_2$SO$_4$. Filtration and concentration afforded the title compound (0.718 g, 99% yield). $^1$H NMR (500 MHz, chloroform-d) δ 7.41-7.31 (m, 5H), 5.24-5.08 (m, 2H), 4.77-4.43 (m, 2H), 3.75-3.57 (m, 3H), 3.37 (s, 2H), 2.66-2.49 (m, 1H). MS(ES+) m/z: 253.2 (M+H); HPLC retention time: 1.023 min (analytical HPLC Method B). Chiral purity: 99.9% ee (chiral HPLC conditions: column: CHIRALPAK® AD-H (25×0.46 cm, 5 μm), 35% MeOH in CO$_2$, 3 mL/min, 45° C., 220 nm, 100 bar).

Intermediates 7-12

Intermediate 7

2-Methyl-1-(4-(4,4,5,5-tetramethyl-1,3,2-dioxaborolan-2-yl)-1H-pyrazol-1-yl) propan-2-ol

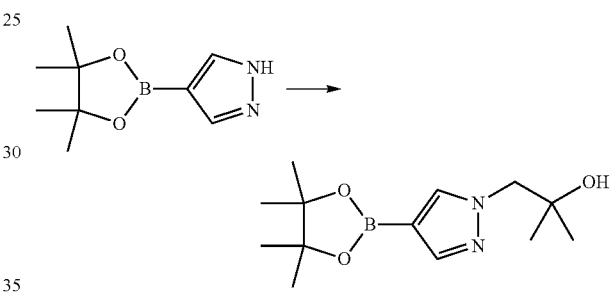

A suspension of 4-(4,4,5,5-tetramethyl-1,3,2-dioxaborolan-2-yl)-1H-pyrazole (514.3 mg, 2.65 mmol), cesium carbonate (1.295 g, 3.98 mmol) and 2,2-dimethyloxirane (0.589 mL, 6.63 mmol) in acetonitrile (5 mL) was heated at 130° C. under microwave for 1 h. The resulting mixture was concentrated. The residue was triturated with dichloromethane and stirred at room temperature for 30 min and filtered. The filtrate was concentrated to give 2-methyl-1-(4-(4,4,5,5-tetramethyl-1,3,2-dioxaborolan-2-yl)-1H-pyrazol-1-yl)propan-2-ol (0.4289 g). This material was used in subsequent Suzuki coupling reactions without further purification. $^1$H NMR (400 MHz, DMSO-d$_6$) δ ppm 7.84 (d, J=0.4 Hz, 1H), 7.55 (d, J=0.7 Hz, 1H), 4.02 (s, 2H), 4.01 (s, 1H), 1.25 (s, 12H), 1.04 (s, 6H).

Intermediates 8-12

According to the procedure for preparation of Intermediate 7, Intermediates 8-12 were prepared via reaction of 4-(4,4,5,5-tetramethyl-1,3,2-dioxaborolan-2-yl)-1H-pyrazole with (R)-2-methyloxirane, (S)-2-methyloxirane, (S)-(+)-3,3,3-trifluoro-1,2-epoxypropane (R)-(+)-3,3,3-trifluoro-1,2-epoxypropane and (R)-2-(methoxymethyl)oxirane which were commercially available.

Intermediates 8-10 were analyzed using analytic HPLC Method B and LCMS Method B. Intermediates 11 and 12 were analyzed using analytic HPLC Method B and LCMS Method A.

| Intermediate No. | Chemical Structure | HPLC Rt (minutes) | LCMS [m/z (M + H)] |
|---|---|---|---|
| 8 | 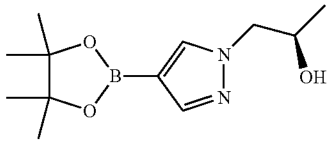 [SMILES: C[C@@H](O)Cn1cc(B2OC(C)(C)C(C)(C)O2)cn1] | 2.033 | 253.2 |
| 9 | 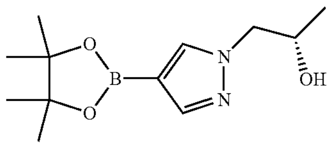 [SMILES: C[C@H](O)Cn1cc(B2OC(C)(C)C(C)(C)O2)cn1] | 2.032 | 253.2 |
| 10 | 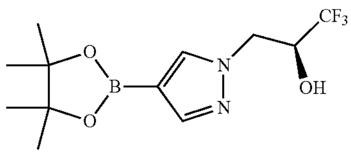 [SMILES: CC1(C)OB(c2cnn(C[C@H](O)C(F)(F)F)c2)OC1(C)C] | 2.090 | 307.2 |
| 11 | 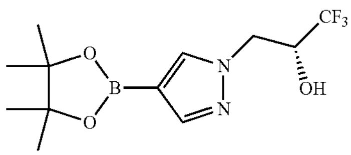 [SMILES: CC1(C)OB(c2cnn(C[C@@H](O)C(F)(F)F)c2)OC1(C)C] | 3.393 | 307.08 |
| 12 | 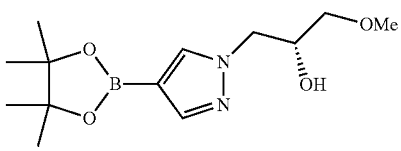 [SMILES: COC[C@H](O)Cn1cc(B2OC(C)(C)C(C)(C)O2)cn1] | 3.063 | 283.08 |
EXAMPLES
Example 1
8-(((3S,4S)-1-(5-Cyanopyridin-2-yl)-4-methylpyrrolidin-3-yl)amino)-2-(1-ethyl-1H-pyrazol-4-yl)imidazo[1,2-b]pyridazine-7-carboxamide
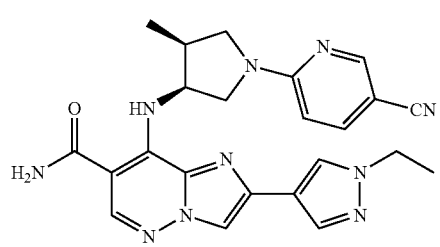 [SMILES: CCn1cc(-c2cn3ncc(C(N)=O)c(N[C@@H]4CN(c5ccc(C#N)cn5)C[C@@H]4C)c3n2)cn1]
Step 1 (3S,4S)-Benzyl 3-((2-bromo-7-carbamoylimidazo[1,2-b]pyridazin-8-yl)amino)-4-methylpyrrolidine-1-carboxylate
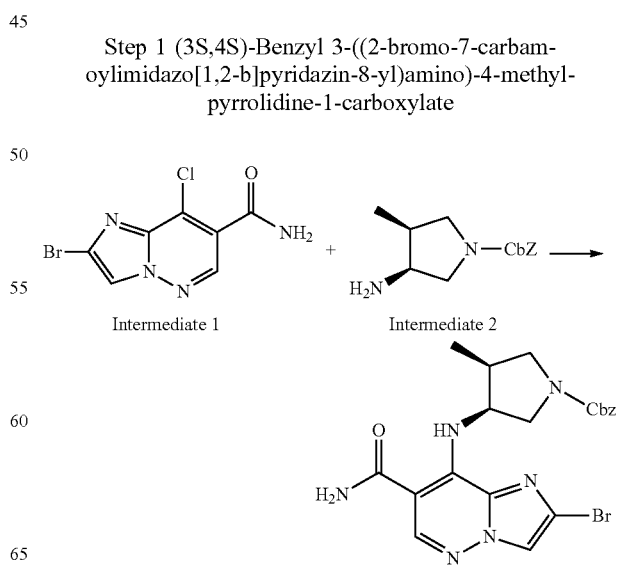

A solution of 2-bromo-8-chloroimidazo[1,2-b]pyridazine-7-carboxamide (2.198 g, 7.98 mmol), (3S,4S)-benzyl 3-amino-4-methylpyrrolidine-1-carboxylate (2.15 g, 9.18 mmol) and Hunig's Base (4.18 ml, 23.94 mmol) in DMF (7.9 ml) in a reaction vial was stirred at 90° C. for 2 h. After cooling to room temperature, the reaction solution was added slowly to a stirred ice-water resulting in a light tan precipitate. The suspension was stirred for 30 min. (3S,4S)-Benzyl 3-((2-bromo-7-carbamoylimidazo[1,2-b]pyridazin-8-yl)amino)-4-methylpyrrolidine-1-carboxylate (3.78 g, 7.98 mmol, 100% yield) was collected as a light tan solid via filtration. ESI-MS (analytical LCMS Method A): m/z 473, 475 ([M+H]+). HPLC (analytical HPLC Method A) Rt: 3.808 min.

Step 2: 2-Bromo-8-(((3S,4S)-4-methylpyrrolidin-3-yl)amino)imidazo[1,2-b]pyridazine-7-carboxamide

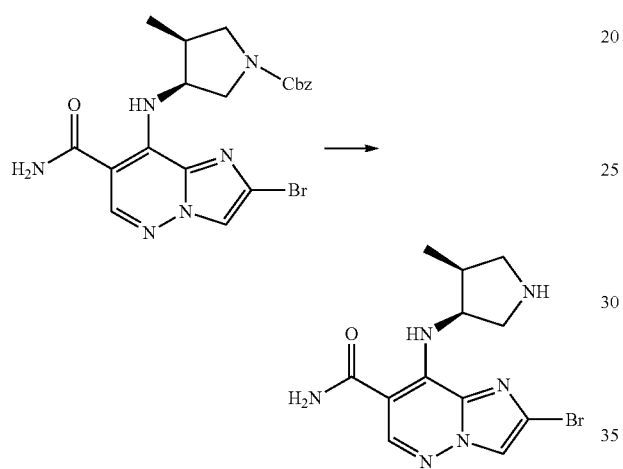

To a suspension of (3S,4S)-benzyl 3-((2-bromo-7-carbamoylimidazo[1,2-b]pyridazin-8-yl)amino)-4-methylpyrrolidine-1-carboxylate (3.78 g, 7.98 mmol) in acetonitrile (53 ml) at 0° C. was added iodotrimethylsilane (3.26 ml, 23.96 mmol) dropwise. The reaction solution was stirred at room temperature for 1.5 h. The reaction was cooled to 0° C. and quenched with methanol (3.23 ml, 80 mmol). The resulting suspension was stirred at 0° C. for 30 min, filtered, washed with diethyl ether, and dried under vacuum to afford 2-bromo-8-(((3S,4S)-4-methylpyrrolidin-3-yl)amino)imidazo[1,2-b]pyridazine-7-carboxamide, 2 hydrobromide (3.94 g, 7.86 mmol, 98% yield) as a light yellow solid. ESI-MS (analytical LCMS Method B): m/z 341.1 ([M+H]+). HPLC (analytical HPLC Method B) Rt: 1.503 min.

Step 3: (3S,4S)-tert-Butyl 3-((2-bromo-7-carbamoylimidazo[1,2-b]pyridazin-8-yl)amino)-4-methylpyrrolidine-1-carboxylate

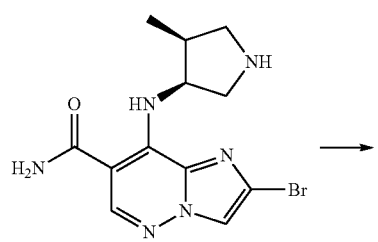

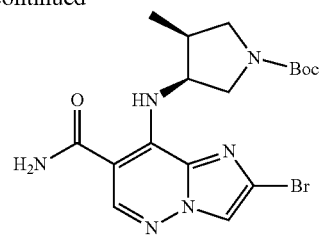

To a suspension of 2-bromo-8-(((3S,4S)-4-methylpyrrolidin-3-yl)amino)imidazo[1,2-b]pyridazine-7-carboxamide (1.206 g, 2.548 mmol) in DCM (12 ml) was added Hunig's Base (2.270 ml, 13.00 mmol) followed by slow addition of a solution of BOC₂O (0.905 ml, 3.90 mmol) in DCM (6 ml). The reaction was stirred at room temperature for 3 h. The reaction mixture was partitioned between water and DCM. The organic phase was washed with brine, dried (Na₂SO₄) and concentrated to give a tan solid. The crude mixture was triturated in CH₃CN to collect the product as an off-white solid (528.5 mg) via filtration. The filtrate was concentrated and purified by flash column (ISCO 12 g column, 20-70% EtOAc/hex over 15 min) to afford additional product (324.4 mg) as a white solid. The combined weight of (3S,4S)-tert-butyl 3-((2-bromo-7-carbamoylimidazo[1,2-b]pyridazin-8-yl)amino)-4-methylpyrrolidine-1-carboxylate was 852.9 mg (1.941 mmol, 76.2% yield). ESI-MS (analytical LCMS Method A): m/z 441 ([M+H]+). HPLC (analytical HPLC Method A) Rt: 3.771 min.

Step 4: 2-(1-Ethyl-1H-pyrazol-4-yl)-8-(((3S,4S)-4-methylpyrrolidin-3-yl)amino)-imidazo[1,2-b]pyridazine-7-carboxamide

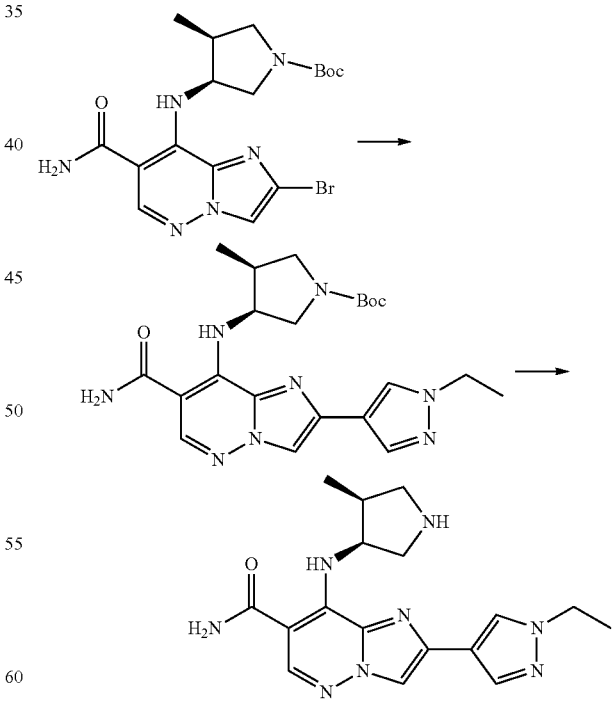

A solution of (3S,4S)-tert-butyl 3-((2-bromo-7-carbamoylimidazo[1,2-b]pyridazin-8-yl)amino)-4-methylpyrrolidine-1-carboxylate (200 mg, 0.455 mmol), 1-ethyl-4-(4,4,5,5-tetramethyl-1,3,2-dioxaborolan-2-yl)-1H-pyrazole (202 mg, 0.911 mmol), and 2M aq K₃PO₄ (0.683 ml, 1.366 mmol)

in dioxane (2 ml) in a reaction vial was purged with $N_2$ for 2 min, followed by addition of $PdCl_2(dppf)$ $CH_2Cl_2$ Adduct (1:1) (37.5 mg, 0.046 mmol). The reaction mixture was purged with nitrogen for 1 min, sealed and heated at 100° C. for 120 min. The product mixture was partitioned between EtOAc and water. The organic phase was washed with brine, filtered through CELITE®, dried ($Na_2SO_4$) and concentrated. The crude product was purified by flash column (ISCO 12 g, 20-80% EtOAc/hexane over 15 min) to afford (3S,4S)-tert-butyl 3-((7-carbamoyl-2-(1-ethyl-1H-pyrazol-4-yl)imidazo[1,2-b]pyridazin-8-yl)amino)-4-methylpyrrolidine-1-carboxylate as an off-white solid, 139 mg. ESI-MS (Method A): m/z 455.2 ([M+H]$^+$).

The off-white solid in DCM (3 ml) was treated with TFA (0.351 ml, 4.55 mmol) at room temperature for 2 h and, after removal of solvent, to afford 2-(1-ethyl-1H-pyrazol-4-yl)-8-(((3S,4S)-4-methylpyrrolidin-3-yl)amino)-imidazo[1,2-b]pyridazine-7-carboxamide, TFA (170 mg, 0.363 mmol, 80% yield) as an off-white solid. ESI-MS (Method A): m/z 355.1 ([M+H]$^+$). HPLC (Method A) Rt: 2.100 min.

Step 5: 8-(((3S,4S)-1-(5-Cyanopyridin-2-yl)-4-methylpyrrolidin-3-yl)amino)-2-(1-ethyl-1H-pyrazol-4-yl)imidazo[1,2-b]pyridazine-7-carboxamide

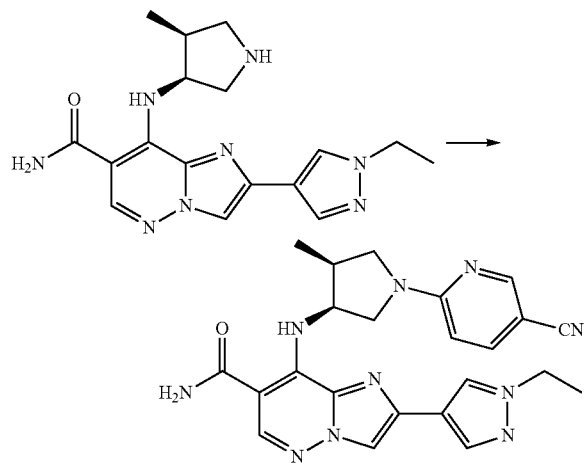

A solution of 2-(1-ethyl-1H-pyrazol-4-yl)-8-(((3S,4S)-4-methylpyrrolidin-3-yl)amino)imidazo[1,2-b]pyridazine-7-carboxamide, 2 TFA (0.020 g, 0.034 mmol), 6-bromonicotinonitrile (0.013 g, 0.069 mmol) and Hunig's Base (0.030 ml, 0.172 mmol) in DMF (0.3 ml) in a reaction vial was stirred at 100° C. for 5 h. The crude material was purified via preparative LC/MS (Method A). Fractions containing the desired product were combined and dried via centrifugal evaporation to afford the title compound of Example 1 (10.0 mg, 0.022 mmol, 63.8% yield). $^1$H NMR (500 MHz, deuterated 1:1 methanol:chloroform) δ 8.53 (br. s., 1H), 8.51 (s, 1H), 8.15 (s, 1H), 8.11 (s, 1H), 8.07 (s, 1H), 7.84 (d, J=8.9 Hz, 1H), 6.69 (d, J=7.4 Hz, 1H), 6.32 (br. s., 1H), 4.43 (q, J=7.3 Hz, 3H), 4.19 (br. s., 1H), 4.12-3.91 (m, 2H), 3.70-3.57 (m, 1H), 3.06 (d, J=12.9 Hz, 1H), 1.72 (t, J=7.4 Hz, 3H), 1.43 (d, J=6.9 Hz, 3H). LC/MS (Method F): m/z 456.20 ([M+H]$^+$), Rt. 1.310 min.

Examples 2-10

According to the procedure described for Example 1, Examples 2-10 were prepared from (3S,4S)-tert-butyl 3-((2-bromo-7-carbamoylimidazo[1,2-b]pyridazin-8-yl)amino)-4-methylpyrrolidine-1-carboxylate (from Step 3 of Example 1) via Suzuki coupling reaction with appropriate boronic acids which were commercially available or boronic acid esters selected from Intermediates 7-11, and N-deprotection under the conditions similar to Step 4 in Example 1, followed by N-arylation with appropriate aryl halides, which were commercially available, under the conditions similar to Step 5 in Example 1.

Example 2 was analyzed using analytical HPLC Method A and analytical LCMS Method A. Examples 3-10 were analyzed using analytical HPLC/LCMS Method F.

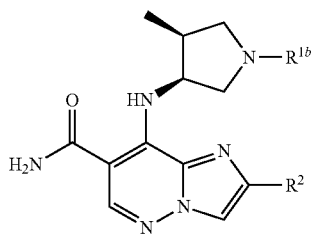

| Ex. No. | Name | —R$^{1b}$ | —R$^2$ | HPLC Rt (minutes) | LCMS [m/z] (M + H) |
|---|---|---|---|---|---|
| 2 | 8-(((3S,4S)-1-(5-cyanopyridin-2-yl)-4-methylpyrrolidin-3-yl)amino)-2-(1-ethyl-1H-pyrazol-4-yl)imidazo[1,2-b]pyridazine-7-carboxamide | pyridin-CN | 1-ethyl-pyrazol | 2.873 | 458.30 |

-continued

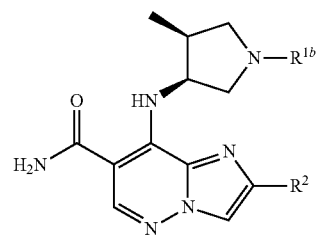

| Ex. No. | Name | —R1b | —R2 | HPLC Rt (minutes) | LCMS [m/z] (M + H) |
|---|---|---|---|---|---|
| 3 | 8-(((3S,4S)-1-(5-cyanopyrimidin-2-yl)-4-methylpyrrolidin-3-yl)amino)-2-(1-ethyl-1H-pyrazol-4-yl)imidazo[1,2-b]pyridazine-7-carboxamide | pyrimidin-CN | 1-ethyl-pyrazol-4-yl | 1.360 | 457.20 |
| 4 | 8-(((3S,4S)-1-(5-cyanopyridin-2-yl)-4-methylpyrrolidin-3-yl)amino)-2-(1-(2-hydroxy-2-methylpropyl)-1H-pyrazol-4-yl)imidazo[1,2-b]pyridazine-7-carboxamide | pyridin-CN | 1-(2-hydroxy-2-methylpropyl)-pyrazol-4-yl | 1.101 | 501.25 |
| 5 | 8-(((3S,4S)-1-(5-cyanopyrimidin-2-yl)-4-methylpyrrolidin-3-yl)amino)-2-(1-((S)-2-hydroxypropyl)-1H-pyrazol-4-yl)imidazo[1,2-b]pyridazine-7-carboxamide | pyrimidin-CN | 1-((S)-2-hydroxypropyl)-pyrazol-4-yl | 1.159 | 488.23 |
| 6 | 8-(((3S,4S)-1-(5-cyanopyridin-2-yl)-4-methylpyrrolidin-3-yl)amino)-2-(1-((R)-2-hydroxypropyl)-1H-pyrazol-4-yl)imidazo[1,2-b]pyridazine-7-carboxamide | pyridin-CN | 1-((R)-2-hydroxypropyl)-pyrazol-4-yl | 1.116 | 487.23 |
| 7 | 8-(((3S,4S)-1-(5-cyanopyrimidin-2-yl)-4-methylpyrrolidin-3-yl)amino)-2-(1-((R)-2-hydroxypropyl)-1H-pyrazol-4-yl)imidazo[1,2-b]pyridazine-7-carboxamide | pyrimidin-CN | 1-((R)-2-hydroxypropyl)-pyrazol-4-yl | 1.159 | 488.23 |
| 8 | 8-(((3S,4S)-1-(5-cyanopyrimidin-2-yl)-4-methylpyrrolidin-3-yl)amino)-2-(1-(2-hydroxy-2-methylpropyl)-1H-pyrazol-4-yl)imidazo[1,2-b]pyridazine-7-carboxamide | pyrimidin-CN | 1-(2-hydroxy-2-methylpropyl)-pyrazol-4-yl | 1.237 | 502.24 |
| 9 | 2-(1-(2-hydroxy-2-methylpropyl)-1H-pyrazol-4-yl)-8-(((3S,4S)-4-methyl-1-(5-(trifluoromethyl)-1,3,4-thiadiazol-2-yl)pyrrolidin-3-yl)amino)imidazo[1,2-b]pyridazine-7-carboxamide | 5-(trifluoromethyl)-1,3,4-thiadiazol-2-yl | 1-(2-hydroxy-2-methylpropyl)-pyrazol-4-yl | 1.470 | 550.20 |
| 10 | 8-(((3S,4S)-1-(5-cyanopyridin-2-yl)-4-methylpyrrolidin-3-yl)amino)-2-(1-((S)-2-hydroxypropyl)-1H-pyrazol-4-yl)imidazo[1,2-b]pyridazine-7-carboxamide | pyridin-CN | 1-((S)-2-hydroxypropyl)-pyrazol-4-yl | 1.072 | 487.23 |

Examples 11-16

Examples 11-16 were prepared from 2-bromo-8-(((3S, 4S)-4-methylpyrrolidin-3-yl)amino)imidazo[1,2-b]pyridazine-7-carboxamide, hydrobromide (from Step 2 of Example 1) via N-arylation with 2-chloropyrimidine-5-carbonitrile or bromo-pyridine following conditions analogous to Step 5 of Example 1 and Suzuki coupling reaction with appropriate boronic acids which were commercially available or boronic acid esters selected from Intermediates 7-12 following conditions analogous to Step 4 of Example 1.

Examples 11-16 were analyzed using analytical HPLC/LCMS Method F.

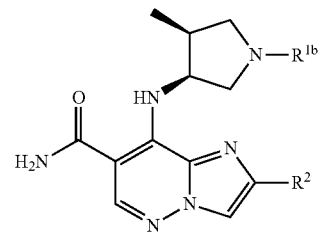

| Ex. No. | Name | —R$^{1b}$ | —R$^2$ | HPLC Rt (minutes) | LCMS [m/z (M + H)] |
|---|---|---|---|---|---|
| 11 | 8-(((3S,4S)-1-(5-cyanopyrimidin-2-yl)-4-methylpyrrolidin-3-yl)amino)-2-(1-isopropyl-1H-pyrazol-4-yl)imidazo[1,2-b]pyridazine-7-carboxamide | pyrimidine-CN | pyrazole-iPr | 1.309 | 472.23 |
| 12 | 8-(((3S,4S)-1-(5-cyanopyrimidin-2-yl)-4-methylpyrrolidin-3-yl)amino)-2-(1-((R)-2-hydroxy-3-methoxypropyl)-1H-pyrazol-4-yl)imidazo[1,2-b]pyridazine-7-carboxamide | pyrimidine-CN | pyrazole-CH2-CH(OH)-CH2-OMe | 1.102 | 518.24 |
| 13 | 8-(((3S,4S)-1-(5-cyanopyrimidin-2-yl)-4-methylpyrrolidin-3-yl)amino)-2-(1,3-dimethyl-1H-pyrazol-4-yl)imidazo[1,2-b]pyridazine-7-carboxamide | pyrimidine-CN | 1,3-dimethylpyrazole | 1.174 | 458.22 |
| 14 | 8-(((3S,4S)-1-(5-cyanopyrimidin-2-yl)-4-methylpyrrolidin-3-yl)amino)-2-(1-propyl-1H-pyrazol-4-yl)imidazo[1,2-b]pyridazine-7-carboxamide | pyrimidine-CN | pyrazole-nPr | 1.309 | 472.23 |
| 15 | 8-(((3S,4S)-1-(5-cyanopyridin-2-yl)-4-methylpyrrolidin-3-yl)amino)-2-(1-propyl-1H-pyrazol-4-yl)imidazo[1,2-b]pyridazine-7-carboxamide | pyridine-CN | pyrazole-nPr | 1.458 | 471.24 |
| 16 | 8-(((3S,4S)-1-(5-cyanopyridin-2-yl)-4-methylpyrrolidin-3-yl)amino)-2-(1-((S)-3,3,3-trifluoro-2-hydroxypropyl)-1H-pyrazol-4-yl)imidazo[1,2-b]pyridazine-7-carboxamide | pyridine-CN | pyrazole-CH2-CH(OH)-CF3 | 1.379 | 541.2 |

Example 17

8-(((3S,4S)-1-(1-Cyanocyclopropanecarbonyl)-4-methylpyrrolidin-3-yl)amino)-2-(1-methyl-1H-pyrazol-4-yl)imidazo[1,2-b]pyridazine-7-carboxamide

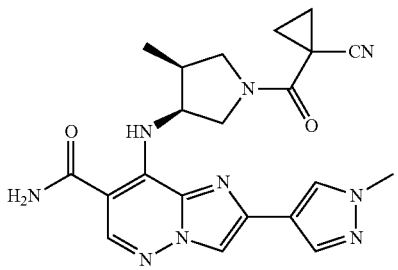 [SMILES: C[C@H]1CN(C(=O)C2(C#N)CC2)C[C@H]1Nc1c(C(N)=O)cnn2cc(-c3cnn(C)c3)nc12]

Step 1: 2-(1-Methyl-1H-pyrazol-4-yl)-8-(((3S,4S)-4-methylpyrrolidin-3-yl)amino)imidazo[1,2-b]pyridazine-7-carboxamide

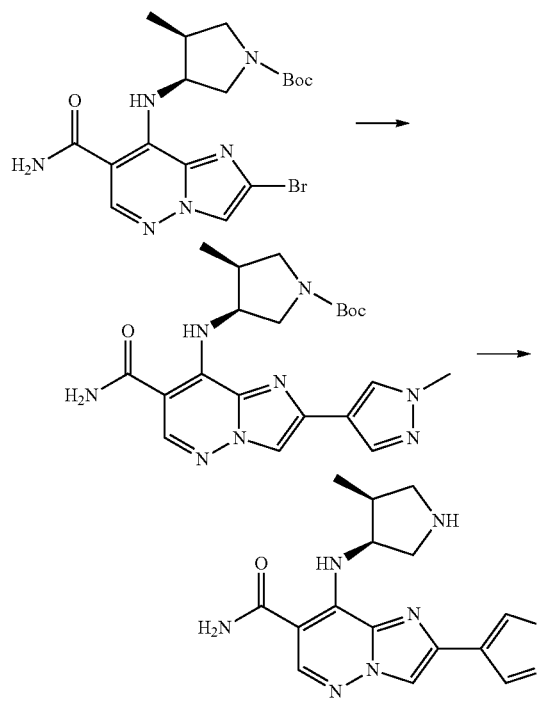

To a reaction vial charged with (3S,4S)-tert-butyl 3-((2-bromo-7-carbamoylimidazo[1,2-b]pyridazin-8-yl)amino)-4-methylpyrrolidine-1-carboxylate (from Step 3 of Example 1, 300 mg, 0.683 mmol), 1-methyl-4-(4,4,5,5-tetramethyl-1,3,2-dioxaborolan-2-yl)-1H-pyrazole (426 mg, 2.049 mmol) and PdCl$_2$(dppf)-CH$_2$Cl$_2$ Adduct (55.8 mg, 0.068 mmol) were added dioxane (4.553 ml) and potassium phosphate, tribasic (1024 µl, 2.049 mmol). The suspension was purged with nitrogen for 5 minutes. The vial was sealed and heated at 90° C. for 1 hr. The reaction mixture was diluted with methanol (10 ml), filtered, and concentrated under reduced pressure, yielding a dark oil. The oil was partitioned between ethyl acetate and water. The organic layer was washed with (sat.) sodium chloride, dried with sodium sulfate, filtered and concentrated under reduced pressure to give an oil. The crude oil was purified via flash chromatography (ISCO silica gel column, 0-10% DCM-MeOH eluents) to give (3S,4S)-tert-butyl 3-((7-carbamoyl-2-(1-methyl-1H-pyrazol-4-yl)imidazo[1,2-b]pyridazin-8-yl)amino)-4-methylpyrrolidine-1-carboxylate as a yellow solid. $^1$H NMR (400 MHz, methanol-d$_4$) δ 8.33 (s, 1H), 8.03-7.95 (m, 2H), 7.86 (s, 1H), 6.07-5.86 (m, 1H), 3.93 (s, 3H), 3.85-3.73 (m, 1H), 3.72-3.62 (m, 1H), 3.57-3.45 (m, 1H), 3.23-3.14 (m, 1H), 2.67 (d, J=4.8 Hz, 1H), 1.46 (d, J=13.0 Hz, 9H), 1.16-1.06 (m, 3H). ESI-MS (analytical LCMS Method B): m/z 441.3 ([M+H]$^+$). HPLC (analytical HPLC Method B) Rt: 3.123 min.

To a solution of (3S,4S)-tert-butyl 3-((7-carbamoyl-2-(1-methyl-1H-pyrazol-4-yl)imidazo[1,2-b]pyridazin-8-yl)amino)-4-methylpyrrolidine-1-carboxylate in DCM (4.5 ml) at 0° C. was added TFA (526 µl, 6.83 mmol) dropwise. The reaction was stirred at 0° C. for 10 minutes and at room temperature for 1.5 h. The reaction solution was concentrated to yield a yellow oil, which was partitioned between ethyl acetate and water. The organic layer was washed with (sat.) sodium chloride, dried with sodium sulfate, filtered and concentrated to give 2-(1-methyl-1H-pyrazol-4-yl)-8-(((3S,4S)-4-methylpyrrolidin-3-yl)amino)imidazo[1,2-b]pyridazine-7-carboxamide, 2 TFA (333.5 mg, 0.587 mmol, 86% yield) as a yellow solid. ESI-MS (analytical LCMS Method B): m/z 341.2 ([M+H]$^+$). HPLC (analytical HPLC Method B) Rt: 1.847 min.

Step 2: 8-(((3S,4S)-1-(1-Cyanocyclopropanecarbonyl)-4-methylpyrrolidin-3-yl)amino)-2-(1-methyl-1H-pyrazol-4-yl)imidazo[1,2-b]pyridazine-7-carboxamide

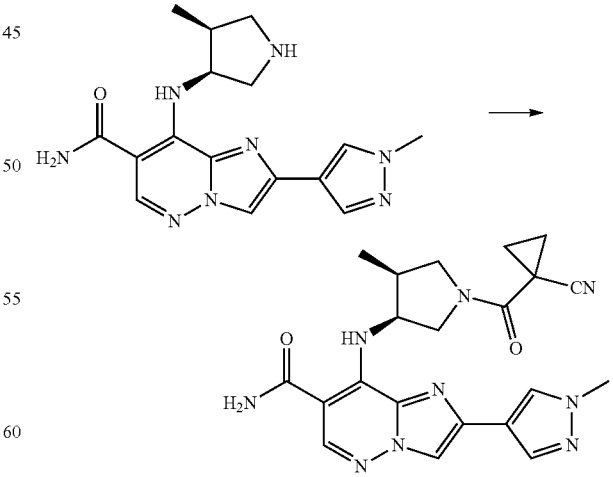

To a solution of cyanocyclopropanecarboxylic acid (3.67 mg, 0.033 mmol) in DCM (330 µl) were added DIEA (14.41 µl, 0.083 mmol) and BOP (17.52 mg, 0.040 mmol). The solution was stirred at room temperature for 10 minutes.

2-(1-Methyl-1H-pyrazol-4-yl)-8-(((3S,4S)-4-methylpyrrolidin-3-yl)amino)imidazo[1,2-b]pyridazine-7-carboxamide, TFA (15 mg, 0.033 mmol) was added. The reaction mixture was stirred at room temperature for another 30 min and concentrated to give an orange oil. The oil was partitioned between ethyl acetate and water. The organic layer was washed with (sat.) sodium chloride, dried with sodium sulfate, filtered and concentrated. The crude product was purified via preparative LCMS (prep. LCMS Method A) to afford 8-(((3S,4S)-1-(1-cyanocyclopropanecarbonyl)-4-methylpyrrolidin-3-yl)amino)-2-(1-methyl-1H-pyrazol-4-yl)imidazo[1,2-b]pyridazine-7-carboxamide (8.5 mg, 0.020 mmol, 59.4% yield) as an off-white solid. $^1$H NMR (500 MHz, DMSO-$d_6$, 2 rotamers) δ 10.74 (d, J=8.4 Hz, 1H), 10.69 (d, J=8.9 Hz, 1H), 8.48 (br. s., 1H), 8.47 (br. s., 1H), 8.28 (s, 1H), 8.27 (s, 1H), 8.12 (s, 2H), 8.01 (br. s., 2H), 7.88 (s, 1H), 7.87 (s, 1H), 7.41 (br. s., 2H), 6.00-5.88 (m, 1H), 5.82 (d, J=5.9 Hz, 1H), 4.25 (dd, J=10.9, 5.0 Hz, 1H), 4.13 (dd, J=10.2, 7.7 Hz, 2H), 3.92 (d, J=3.5 Hz, 1H), 3.88 (s, 6H), 3.79 (dd, J=12.6, 5.2 Hz, 1H), 3.69 (dd, J=12.1, 7.7 Hz, 1H), 3.58 (s, 1H), 3.54-3.50 (m, 1H), 2.80-2.74 (m, 1H), 2.72-2.65 (m, 1H), 1.64-1.52 (m, 6H), 1.50-1.45 (m, 1H), 1.39-1.34 (m, 1H), 1.08 (d, J=6.9 Hz, 3H), 1.04 (d, J=6.9 Hz, 3H). HPLC/LCMS (Method F): m/z 434.10 ([M+H]$^+$), Rt. 1.066 min.

Examples 18-22

According to the procedure described for Example 17, Examples 18-22 were prepared from (3S,4S)-tert-butyl 3-((2-bromo-7-carbamoylimidazo[1,2-b]pyridazin-8-yl)amino)-4-methylpyrrolidine-1-carboxylate (from Step 3 of Example 1) via Suzuki coupling reaction with appropriate boronic acids which were commercially available or boronic acid esters selected from Intermediates 7-12, and N-deprotection under the conditions similar to Step 1 of Example 17 and amidation with appropriate acids under the conditions similar to Step 2 of Example 17.

Examples 18-22 were analyzed using analytical HPLC/LCMS Method F.

| Ex. No. | Name | —R$^{1b}$ | —R$^2$ | HPLC Rt (minutes) | LCMS [m/z (M + H)] |
|---|---|---|---|---|---|
| 18 | 8-(((3S,4S)-1-(1-cyanocyclopropanecarbonyl)-4-methylpyrrolidin-3-yl)amino)-2-(1-ethyl-1H-pyrazol-4-yl)imidazo[1,2-b]pyridazine-7-carboxamide | cyanocyclopropanecarbonyl | 1-ethyl-1H-pyrazol-4-yl | 1.213 | 448.22 |
| 19 | 8-(((3S,4S)-1-(1-cyanocyclobutanecarbonyl)-4-methylpyrrolidin-3-yl)amino)-2-(1-methyl-1H-pyrazol-4-yl)imidazo[1,2-b]pyridazine-7-carboxamide | cyanocyclobutanecarbonyl | 1-methyl-1H-pyrazol-4-yl | 1.121 | 448.10 |
| 20 | 8-(((3S,4S)-1-(1-cyanocyclopropanecarbonyl)-4-methylpyrrolidin-3-yl)amino)-2-(1-(2-hydroxy-2-methylpropyl)-1H-pyrazol-4-yl)imidazo[1,2-b]pyridazine-7-carboxamide | cyanocyclopropanecarbonyl | 1-(2-hydroxy-2-methylpropyl)-1H-pyrazol-4-yl | 1.076 | 492.20 |
| 21 | 8-(((3S,4S)-1-(1-cyanocyclopropanecarbonyl)-4-methylpyrrolidin-3-yl)amino)-2-(1-((S)-2-hydroxypropyl)-1H-pyrazol-4-yl)imidazo[1,2-b]pyridazine-7-carboxamide | cyanocyclopropanecarbonyl | 1-((S)-2-hydroxypropyl)-1H-pyrazol-4-yl | 1.031 | 478.15 |
| 22 | 8-(((3S,4S)-1-(3-cyanooxetane-3-carbonyl)-4-methylpyrrolidin-3-yl)amino)-2-(1-methyl-1H-pyrazol-4-yl)imidazo[1,2-b]pyridazine-7-carboxamide | 3-cyanooxetane-3-carbonyl | 1-methyl-1H-pyrazol-4-yl | 1.072 | 450.1 |

Examples 23-35

Examples 23-35 were prepared from 2-bromo-8-(((3S,4S)-4-methylpyrrolidin-3-yl)amino)imidazo[1,2-b]

pyridazine-7-carboxamide (from Step 2 of Example 1) via amidation with appropriate acid following conditions analogous to Step 2 of Example 17 and Suzuki coupling reaction with appropriate boronic acids which were commercially available or boronic acid esters selected from Intermediates 7-12 following conditions analogous to Step 1 of Example 17.

Examples 23-35 were analyzed using analytical HPLC/LCMS Method F.

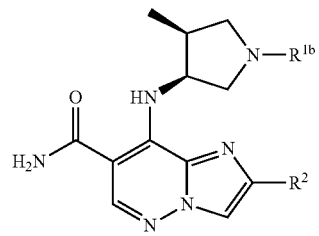

| Ex. No. | Name | —R$^{1b}$ | —R$^2$ | HPLC Rt (minutes) | LCMS [m/z (M + H)] |
|---|---|---|---|---|---|
| 23 | 8-(((3S,4S)-1-(1-cyanocyclopropanecarbonyl)-4-methylpyrrolidin-3-yl)amino)-2-(1-methyl-1H-pyrazol-5-yl)imidazo[1,2-b]pyridazine-7-carboxamide | | | 1.189 | 434.20 |
| 24 | 8-(((3S,4S)-1-(1-cyanocyclopropanecarbonyl)-4-methylpyrrolidin-3-yl)amino)-2-(1-((R)-2-hydroxy-3-methoxypropyl)-1H-pyrazol-4-yl)imidazo[1,2-b]pyridazine-7-carboxamide | | | 1.087 | 508.24 |
| 25 | 8-(((3S,4S)-1-(1-cyanocyclopropanecarbonyl)-4-methylpyrrolidin-3-yl)amino)-2-(1,3,5-trimethyl-1H-pyrazol-4-yl)imidazo[1,2-b]pyridazine-7-carboxamide | | | 1.087 | 462.24 |
| 26 | 8-(((3S,4S)-1-(1-cyanocyclopropanecarbonyl)-4-methylpyrrolidin-3-yl)amino)-2-(1,3-dimethyl-1H-pyrazol-4-yl)imidazo[1,2-b]pyridazine-7-carboxamide | | | 1.184 | 448.22 |
| 27 | 8-(((3S,4S)-1-(1-cyanocyclopropanecarbonyl)-4-methylpyrrolidin-3-yl)amino)-2-(1-((R)-3,3,3-trifluoro-2-hydroxypropyl)-1H-pyrazol-4-yl)imidazo[1,2-b]pyridazine-7-carboxamide | | | 531.20 | 532.20 |
| 28 | 8-(((3S,4S)-1-(1-cyanocyclopropanecarbonyl)-4-methylpyrrolidin-3-yl)amino)-2-(1-propyl-1H-pyrazol-4-yl)imidazo[1,2-b]pyridazine-7-carboxamide | | | 1.229 | 462.24 |
| 29 | 8-(((3S,4S)-1-(1-cyanocyclopropanecarbonyl)-4-methylpyrrolidin-3-yl)amino)-2-(1-isopropyl-1H-pyrazol-4-yl)imidazo[1,2-b]pyridazine-7-carboxamide | | | 1.222 | 462.24 |

-continued

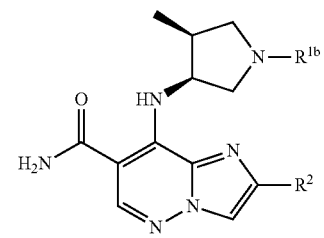

| Ex. No. | Name | —R<sup>1b</sup> | —R<sup>2</sup> | HPLC Rt (minutes) | LCMS [m/z (M + H)] |
|---|---|---|---|---|---|
| 30 | 8-(((3S,4S)-1-(1-cyanocyclopropanecarbonyl)-4-methylpyrrolidin-3-yl)amino)-2-(1-methyl-1H-indazol-5-yl)imidazo[1,2-b]pyridazine-7-carboxamide | | | 1.264 | 484.22 |
| 31 | 8-(((3S,4S)-1-(1-cyanocyclopropanecarbonyl)-4-methylpyrrolidin-3-yl)amino)-2-(6-methoxypyridin-3-yl)imidazo[1,2-b]pyridazine-7-carboxamide | | | 1.276 | 461.20 |
| 32 | 8-(((3S,4S)-1-(1-cyanocyclopropanecarbonyl)-4-methylpyrrolidin-3-yl)amino)-2-(2-methylpyridin-4-yl)imidazo[1,2-b]pyridazine-7-carboxamide | | | 0.988 | 445.21 |
| 33 | 8-(((3S,4S)-1-(2-cyano-2-methylpropanoyl)-4-methylpyrrolidin-3-yl)amino)-2-(1,3,5-trimethyl-1H-pyrazol-4-yl)imidazo[1,2-b]pyridazine-7-carboxamide | | | 1.191 | 464.25 |
| 34 | 8-(((3S,4S)-1-(2-cyano-2-methylpropanoyl)-4-methylpyrrolidin-3-yl)amino)-2-(1,3-dimethyl-1H-pyrazol-4-yl)imidazo[1,2-b]pyridazine-7-carboxamide | | | 1.203 | 450.24 |
| 35 | 8-(((3S,4S)-1-(1-cyanocyclopropanecarbonyl)-4-methylpyrrolidin-3-yl)amino)-2-(1-cyclopropyl-1H-pyrazol-4-yl)imidazo[1,2-b]pyridazine-7-carboxamide | | | 1.291 | 460.22 |

Example 36

8-(((3S,4S)-1-(5-Cyanopyridin-2-yl)-4-ethylpyrrolidin-3-yl)amino)-2-(1-ethyl-1H-pyrazol-4-yl)imidazo[1,2-b]pyridazine-7-carboxamide

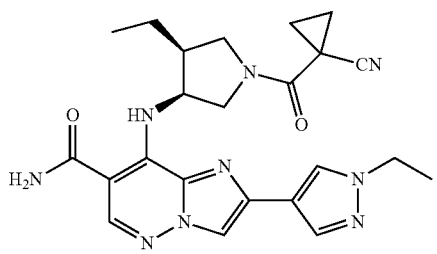 [SMILES: CC[C@H]1CN(C(=O)C2(C#N)CC2)C[C@H]1Nc1c(C(N)=O)cnn2cc(-c3cnn(CC)c3)nc12]

Step 1 (3S,4S)-Benzyl 3-((2-bromo-7-carbamoylimidazo[1,2-b]pyridazin-8-yl)amino)-4-ethylpyrrolidine-1-carboxylate

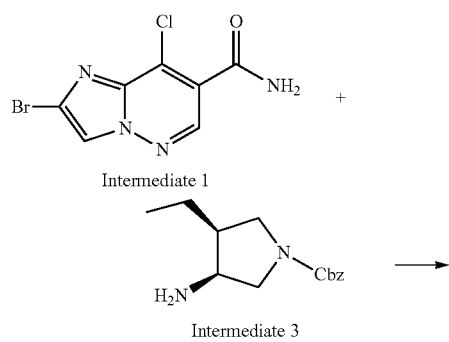

A solution of 2-bromo-8-chloroimidazo[1,2-b]pyridazine-7-carboxamide (0.940 g, 3.41 mmol), (3S,4S)-benzyl 3-amino-4-ethylpyrrolidine-1-carboxylate (1.017 g, 4.09 mmol) and Hunig's Base (1.788 ml, 10.24 mmol) in DMF (3.0 ml) in a reaction vial was stirred at 90° C. for 2 h. The reaction solution was added slowly to a stirred ice-water resulting in a light tan precipitate. The suspension was stirred for 30 min at 0° C. After filtration, (3S,4S)-benzyl 3-((2-bromo-7-carbamoylimidazo[1,2-b]pyridazin-8-yl)amino)-4-ethylpyrrolidine-1-carboxylate was collected as a light tan solid (1.716 g, 3.52 mmol, 100% yield). ESI-MS (analytical LCMS Method A): m/z 489.1, 487.1 ([M+H]$^+$).

Step 2: 2-Bromo-8-(((3S,4S)-4-ethylpyrrolidin-3-yl)amino)imidazo[1,2-b]pyridazine-7-carboxamide, hydroiodide

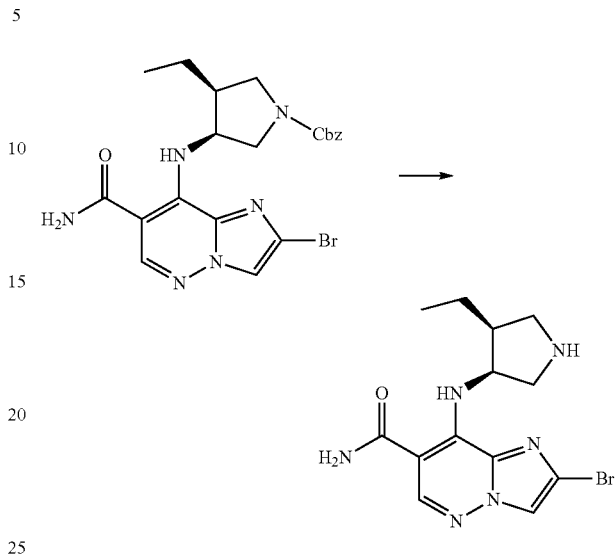

To a suspension of (3S,4S)-benzyl 3-((2-bromo-7-carbamoylimidazo[1,2-b]pyridazin-8-yl)amino)-4-ethylpyrrolidine-1-carboxylate (1000 mg, 2.052 mmol) in acetonitrile (8 ml) and DCM (4 ml) was added iodotrimethylsilane (1.117 ml, 8.21 mmol) dropwise at RT. The resulting dark red clear solution was stirred at rt for 1.3 h forming a yellow precipitate. The reaction was quenched with MeOH (2 ml) at 0° C., and stirred at 0° C. for 30 min. The desired product, 2-bromo-8-(((3S,4S)-4-ethylpyrrolidin-3-yl)amino)imidazo[1,2-b]pyridazine-7-carboxamide, hydroiodide was collected via filtration as a light tan solid (795 mg, 1.65 mmol, 80% yield). ESI-MS (analytical LCMS Method A): m/z 353.0 ([M+H]$^+$).

Step 3: (3S,4S)-tert-Butyl 3-((2-bromo-7-carbamoylimidazo[1,2-b]pyridazin-8-yl)amino)-4-ethylpyrrolidine-1-carboxylate

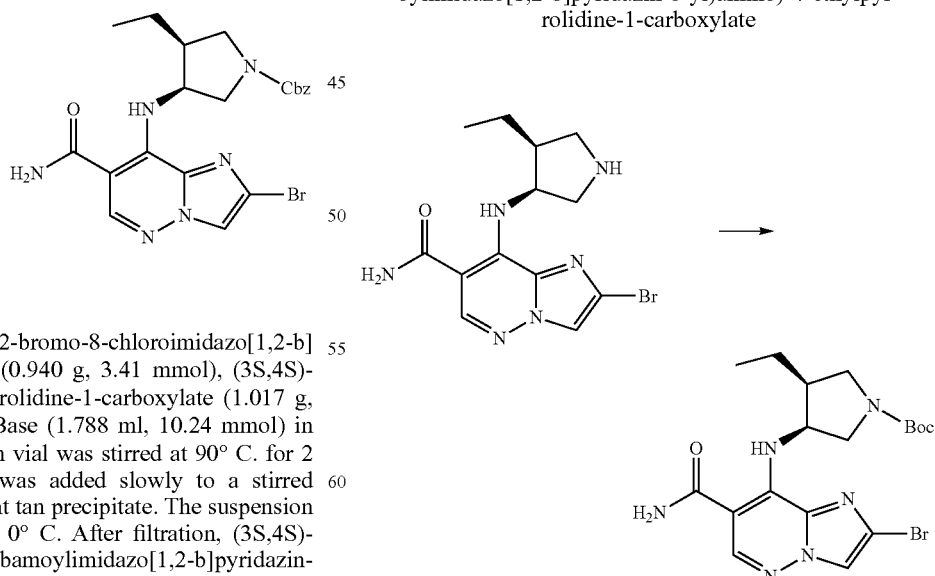

The above-mentioned tan solid (795 mg, 1.65 mmol) in DCM (4 ml) was treated with Hunig's Base (1.792 ml, 10.26 mmol) followed by slow addition of a solution of BOC₂O (0.715 ml, 3.08 mmol) in DCM (4 ml). The reaction was stirred at room temperature for 3 h. The reaction mixture was partitioned between water and DCM. The organic phase was washed with brine, dried (Na₂SO₄) and concentrated to give a brown solid, which was purified by flash column (ISCO 12 g-column, 20-50% EtOAc/hex) to afford (3S,4S)-tert-butyl 3-((2-bromo-7-carbamoylimidazo[1,2-b]pyridazin-8-yl)amino)-4-ethylpyrrolidine-1-carboxylate as a white solid (735 mg, 1.611 mmol, 97.6% yield). ESI-MS (analytical LCMS Method A): m/z 455.0 ([M+H]⁺). HPLC (analytical HPLC Method A) Rt: 3.855 min.

Step 4: 2-(1-Ethyl-1H-pyrazol-4-yl)-8-(((3S,4S)-4-ethylpyrrolidin-3-yl)amino)imidazo[1,2-b]pyridazine-7-carboxamide

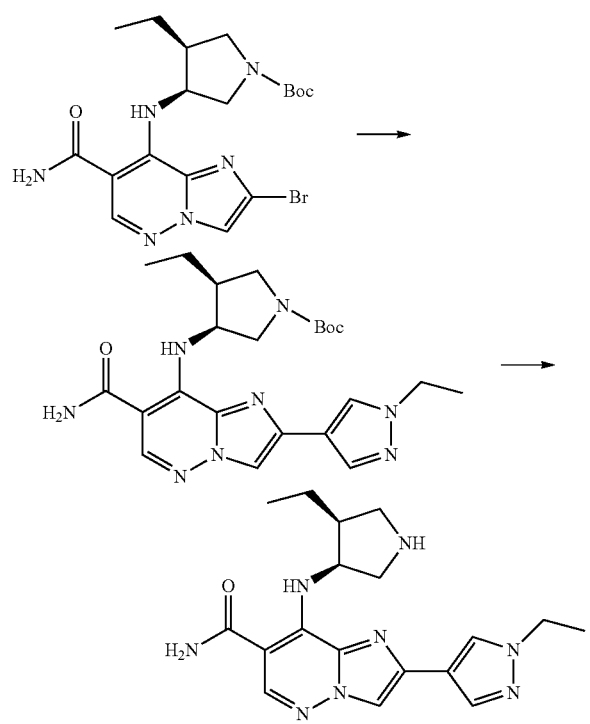

A solution of (3S,4S)-tert-butyl 3-((2-bromo-7-carbamoylimidazo[1,2-b]pyridazin-8-yl)amino)-4-ethylpyrrolidine-1-carboxylate (200 mg, 0.441 mmol), 1-ethyl-4-(4,4,5,5-tetramethyl-1,3,2-dioxaborolan-2-yl)-1H-pyrazole (147 mg, 0.662 mmol) in 2M aq K₃PO₄ (0.662 ml, 1.324 mmol) and dioxane (2 ml) was purged with N₂ for 2 min, followed by addition of PdCl₂(dppf) CH₂Cl₂ Adduct (1:1) (36.3 mg, 0.044 mmol). The reaction mixture was purged with nitrogen for 2 min, sealed and heated at 100° C. for 120 min. The reaction mixture was partitioned between EtOAc and water. The organic phase was washed with brine, filtered through CELITE®, dried (Na₂SO₄) and concentrated. The crude product was purified by flash chromatography (ISCO 12 g column, 20-80% EtOAc/hexane over 15 min) to afford (3S,4S)-tert-butyl 3-((7-carbamoyl-2-(1-ethyl-1H-pyrazol-4-yl)imidazo[1,2-b]pyridazin-8-yl)amino)-4-ethylpyrrolidine-1-carboxylate as an off-white solid.

This solid was taken into DCM (3.0 ml) and treated with TFA (0.204 ml, 2.65 mmol) overnight. Removal of solvent afforded 2-(1-ethyl-1H-pyrazol-4-yl)-8-(((3S,4S)-4-ethylpyrrolidin-3-yl)amino)imidazo[1,2-b]pyridazine-7-carboxamide, TFA (162 mg, 0.336 mmol, 76% yield) as a white solid. ESI-MS (analytical LCMS Method A): m/z 369.1 ([M+H]⁺). HPLC (analytical HPLC Method A) Rt: 2.313 min.

Step 5: 8-(((3S,4S)-1-(5-Cyanopyridin-2-yl)-4-ethylpyrrolidin-3-yl)amino)-2-(1-ethyl-1H-pyrazol-4-yl)imidazo[1,2-b]pyridazine-7-carboxamide

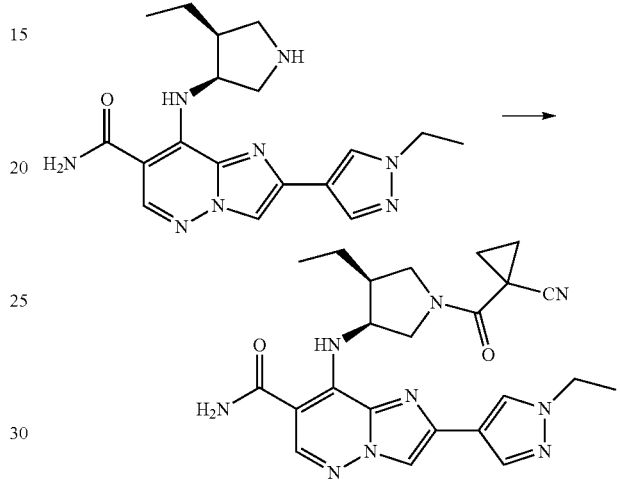

A solution of 2-(1-ethyl-1H-pyrazol-4-yl)-8-(((3S,4S)-4-ethylpyrrolidin-3-yl)amino)imidazo[1,2-b]pyridazine-7-carboxamide, TFA (11 mg, 0.023 mmol), 1-cyanocyclopropanecarboxylic acid (5.07 mg, 0.046 mmol), HATU (13.00 mg, 0.034 mmol) and DIPEA (0.020 ml, 0.114 mmol) in DMF (0.4 ml) was stirred at room temperature for 45 min. The crude material was purified via preparative LC/MS (preparative LC/MS Method A). Fractions containing the desired product were combined and dried via centrifugal evaporation to afford the title compound of Example 36 (8 mg, 0.017 mmol, 76% yield). ¹H NMR (500 MHz, methanol-d₄, 2 rotamers) δ 8.52 (d, J=7.4 Hz, 2H), 8.17 (s, 1H), 8.12 (d, J=2.5 Hz, 2H), 8.10 (s, 1H), 8.05 (d, J=5.0 Hz, 2H), 6.20 (t, J=4.2 Hz, 1H), 6.19-6.16 (m, 1H), 4.57 (dd, J=11.4, 5.0 Hz, 1H), 4.51-4.46 (m, 1H), 4.45-4.38 (m, 6H), 4.07-4.02 (m, 2H), 3.97 (t, J=10.9 Hz, 1H), 3.59 (t, J=11.4 Hz, 1H), 2.84-2.75 (m, 1H), 2.73-2.65 (m, 1H), 2.03-1.98 (m, 1H), 1.96-1.81 (m, 4H), 1.81-1.73 (m, 4H), 1.73-1.63 (m, 8H), 1.62-1.58 (m, 1H), 1.21 (t, J=7.4 Hz, 3H), 1.18 (t, J=7.4 Hz, 3H). HPLC/LCMS (Method F): m/z 461.20 ([M+H]⁺), Rt. 1.30 min.

Examples 37-39

According to the procedure described for Example 36, Examples 37-39 were prepared from (3S,4S)-tert-butyl 3-((2-bromo-7-carbamoylimidazo[1,2-b]pyridazin-8-yl)amino)-4-ethylpyrrolidine-1-carboxylate (from Step 3 of Example 36) via Suzuki coupling reaction with appropriate boronic acids or boronic acid esters which were commercially available and N-deprotection of N-Boc under conditions similar to Step 4 of Example 36 and amidation with appropriate acids under conditions similar to Step 5 of Example 36.

Examples 37-39 were analyzed using analytical HPLC/LCMS Method F.

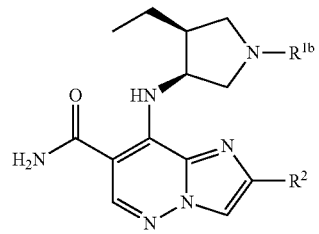

| Ex. No. | Name | —R$^{1b}$ | —R$^2$ | HPLC Rt (minutes) | LCMS [m/z] (M + H)] |
|---|---|---|---|---|---|
| 37 | 8-(((3S,4S)-1-(1-cyanocyclobutanecarbonyl)-4-ethylpyrrolidin-3-yl)amino)-2-(1-ethyl-1H-pyrazol-4-yl)imidazo[1,2-b]pyridazine-7-carboxamide | cyanocyclobutanecarbonyl | 1-ethyl-1H-pyrazol-4-yl | 1.38 | 475.2 |
| 38 | 8-(((3S,4S)-1-(1-cyanocyclobutanecarbonyl)-4-ethylpyrrolidin-3-yl)amino)-2-(1-methyl-1H-pyrazol-4-yl)imidazo[1,2-b]pyridazine-7-carboxamide | cyanocyclobutanecarbonyl | 1-methyl-1H-pyrazol-4-yl | 1.136 | 449.15 |
| 39 | 8-(((3S,4S)-1-(1-cyanocyclopropanecarbonyl)-4-ethylpyrrolidin-3-yl)amino)-2-(1-methyl-1H-pyrazol-4-yl)imidazo[1,2-b]pyridazine-7-carboxamide | cyanocyclopropanecarbonyl | 1-methyl-1H-pyrazol-4-yl | 1.144 | 449.10 |

Examples 40-51

Examples 40-51 were prepared from 2-bromo-8-(((3S,4S)-4-ethylpyrrolidin-3-yl)amino)imidazo[1,2-b]pyridazine-7-carboxamide (from Step 2 of Example 36) via amidation with appropriate acids following conditions analogous to Step 5 of Example 36 and Suzuki coupling reaction with appropriate boronic acids which were commercially available or boronic acid esters selected from Intermediates 7-12 following conditions analogous to Step 4 of Example 36.

Examples 40-51 were analyzed using analytical HPLC/LCMS Method F.

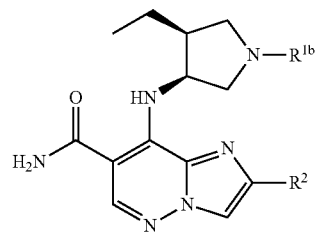

| Ex. No. | Name | —R$^{1b}$ | —R$^2$ | HPLC Rt (minutes) | LCMS [m/z] (M + H)] |
|---|---|---|---|---|---|
| 40 | 8-(((3S,4S)-1-(1-cyanocyclopropanecarbonyl)-4-ethylpyrrolidin-3-yl)amino)-2-(quinolin-6-yl)imidazo[1,2-b]pyridazine-7-carboxamide | cyanocyclopropanecarbonyl | quinolin-6-yl | 1.075 | 495.23 |

-continued

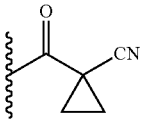

| Ex. No. | Name | —R$^{1b}$ | —R$^2$ | HPLC Rt (minutes) | LCMS [m/z (M + H)] |
|---|---|---|---|---|---|
| 41 | 8-(((3S,4S)-1-(1-cyanocyclopropanecarbonyl)-4-ethylpyrrolidin-3-yl)amino)-2-(2-methylpyridin-4-yl)imidazo[1,2-b]pyridazine-7-carboxamide | 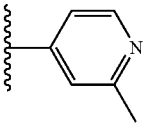 | 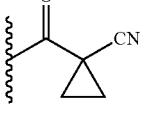 | 1.128 | 475.22 |
| 42 | 8-(((3S,4S)-1-(1-cyanocyclopropanecarbonyl)-4-ethylpyrrolidin-3-yl)amino)-2-(1-methyl-1H-indazol-5-yl)imidazo[1,2-b]pyridazine-7-carboxamide | 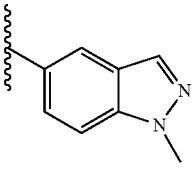 [SMILES: *c1ccc2c(cnn2C)c1] | 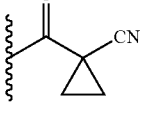 | 1.334 | 498.24 |
| 43 | 8-(((3S,4S)-1-(1-cyanocyclopropanecarbonyl)-4-ethylpyrrolidin-3-yl)amino)-2-(1,3,5-trimethyl-1H-pyrazol-4-yl)imidazo[1,2-b]pyridazine-7-carboxamide | 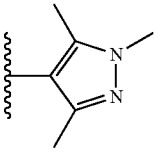 [SMILES: *c1c(C)nn(C)c1C] | 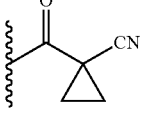 | 1.15 | 476.4 |
| 44 | 8-(((3S,4S)-1-(1-cyanocyclopropanecarbonyl)-4-ethylpyrrolidin-3-yl)amino)-2-(1-methyl-1H-pyrazol-5-yl)imidazo[1,2-b]pyridazine-7-carboxamide | 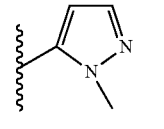 [SMILES: *c1ccnn1C] | 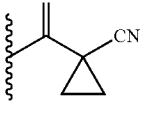 | 1.20 | 448.4 |
| 45 | 8-(((3S,4S)-1-(1-cyanocyclopropanecarbonyl)-4-ethylpyrrolidin-3-yl)amino)-2-(1,3-dimethyl-1H-pyrazol-4-yl)imidazo[1,2-b]pyridazine-7-carboxamide | 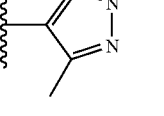 | 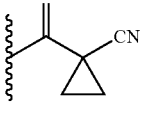 | 2.74 | 462.3 |
| 46 | 8-(((3S,4S)-1-(1-cyanocyclopropanecarbonyl)-4-ethylpyrrolidin-3-yl)amino)-2-(1-(2-hydroxy-2-methylpropyl)-1H-pyrazol-4-yl)imidazo[1,2-b]pyridazine-7-carboxamide | 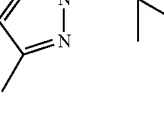 | 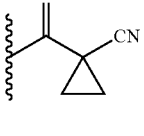 | 1.279 | 520.28 |
| 47 | 8-(((3S,4S)-1-(1-cyanocyclopropanecarbonyl)-4-ethylpyrrolidin-3-yl)amino)-2-(1-cyclopropyl-1H-pyrazol-4-yl)imidazo[1,2-b]pyridazine-7-carboxamide | 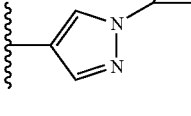 | 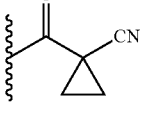 | 1.397 | 474.24 |
| 48 | 8-(((3S,4S)-1-(1-cyanocyclopropanecarbonyl)-4-ethylpyrrolidin-3-yl)amino)-2-(1-propyl-1H-pyrazol-4-yl)imidazo[1,2-b]pyridazine-7-carboxamide | 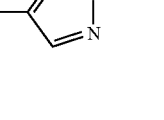 | | 1.464 | 476.25 |

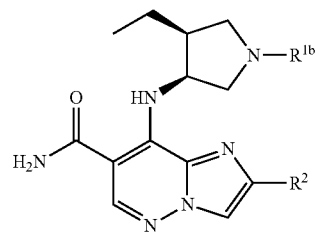

| Ex. No. | Name | —R[1b] | —R[2] | HPLC Rt (minutes) | LCMS [m/z (M + H)] |
|---|---|---|---|---|---|
| 49 | 8-(((3S,4S)-1-(1-cyanocyclopropanecarbonyl)-4-ethylpyrrolidin-3-yl)amino)-2-(1-methyl-1H-pyrazol-3-yl)imidazo[1,2-b]pyridazine-7-carboxamide | | | 1.292 | 448.22 |
| 50 | 8-(((3S,4S)-1-(1-cyanocyclopropanecarbonyl)-4-ethylpyrrolidin-3-yl)amino)-2-(2,4-dimethylthiazol-5-yl)imidazo[1,2-b]pyridazine-7-carboxamide | | | 1.299 | 479.20 |
| 51 | 8-(((3S,4S)-1-(1-cyanocyclopropanecarbonyl)-4-ethylpyrrolidin-3-yl)amino)-2-(1-isopropyl-1H-pyrazol-4-yl)imidazo[1,2-b]pyridazine-7-carboxamide | | | 1.327 | 480.23 |

Example 52

Example 52 was prepared from (3S,4S)-tert-butyl 3-((2-bromo-7-carbamoylimidazo[1,2-b]pyridazin-8-yl)amino)-4-ethylpyrrolidine-1-carboxylate (from Step 3 of Example 36) via Suzuki coupling reaction with appropriate boronic acids which were commercially available or boronic acid esters selected from Intermediates 7-12 and N-deprotection following conditions analogous to Step 4 of Example 36, and N-arylation with appropriate aryl halides, which were commercially available, following conditions analogous to Step 5 of Example 1.

Example 52 was analyzed using analytical HPLC/LCMS Method F.

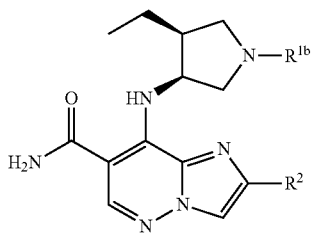

| Ex. No. | Name | —R[1b] | —R[2] | HPLC Rt (minutes) | LCMS [m/z (M + H)] |
|---|---|---|---|---|---|
| 52 | 8-(((3S,4S)-1-(5-cyanopyridin-2-yl)-4-ethylpyrrolidin-3-yl)amino)-2-(1-methyl-1H-pyrazol-4-yl)imidazo[1,2-b]pyridazine-7-carboxamide | | | 1.30 | 456.2 |

Example 53

(R)-8-((1-(6-Cyanopyridazin-3-yl)-3,3-dimethylpiperidin-4-yl)amino)-2-(1-ethyl-1H-pyrazol-4-yl)imidazo[1,2-b]pyridazine-7-carboxamide

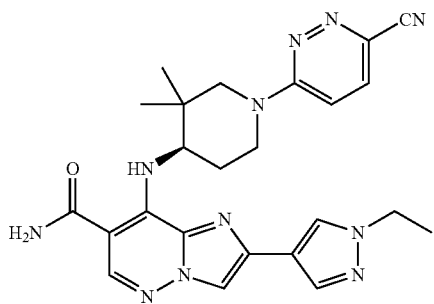 [SMILES: CCn1cc(-c2cn3ncc(C(N)=O)c(N[C@@H]4CCN(c5ccc(C#N)nn5)CC4(C)C)c3n2)cn1]

Step 1: (R)-tert-Butyl 4-((2-bromo-7-carbamoylimidazo[1,2-b]pyridazin-8-yl)amino)-3,3-dimethylpiperidine-1-carboxylate

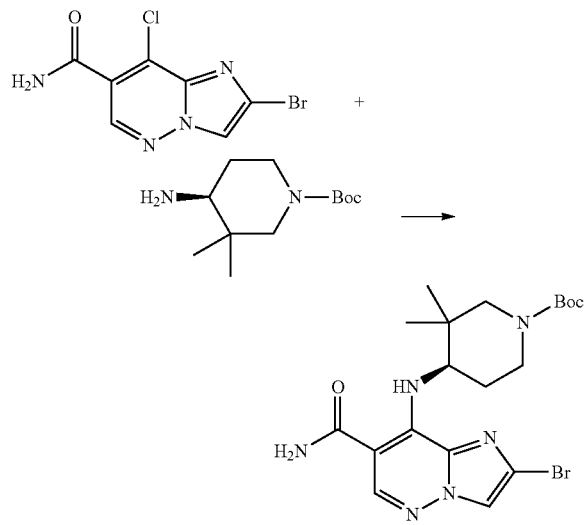

Intermediate 4

To a solution of 2-bromo-8-chloroimidazo[1,2-b]pyridazine-7-carboxamide (170 mg, 0.617 mmol) and (R)-tert-butyl 4-amino-3,3-dimethylpiperidine-1-carboxylate (144 mg, 0.633 mmol) in DMF (1543 µl) was added DIEA (237 µl, 1.358 mmol). The reaction was heated at 90° C. for 2 hours. After cooling to room temperature, the reaction mixture was partitioned between water and ethyl acetate (100 ml). The ethyl acetate layer was washed with water (3×100 ml), dried with sodium sulfate, filtered, and concentrated under reduced pressure. The crude solid was purified via flash chromatography (ISCO silica gel column, 0-10% MeOH-DCM) to afford (R)-tert-butyl 4-((2-bromo-7-carbamoylimidazo[1,2-b]pyridazin-8-yl)amino)-3,3-dimethylpiperidine-1-carboxylate (255 mg, 0.546 mmol, 88% yield) as a faint yellow solid. ESI-MS (analytical LCMS Method A): m/z 467.0 ([M+H]+). HPLC (analytical HPLC Method A) Rt: 3.413 min.

Step 2: (+/−)-6-Bromo-4-(1-(6-cyanopyridazin-3-yl)-3,3-dimethylpiperidin-4-ylamino)pyrrolo[1,2-b]pyridazine-3-carboxamide

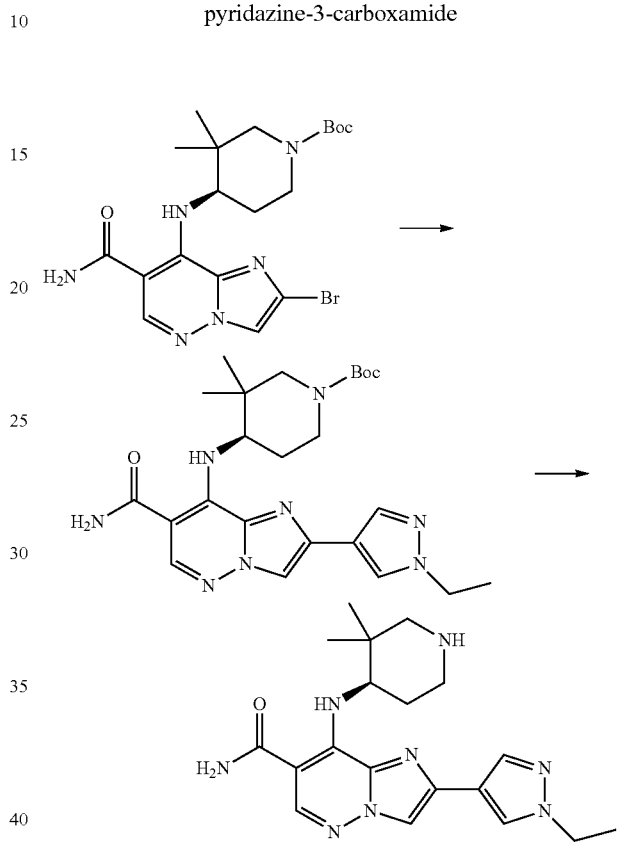

To a reaction vial charged with (R)-tert-butyl 4-((2-bromo-7-carbamoylimidazo[1,2-b]pyridazin-8-yl)amino)-3,3-dimethylpiperidine-1-carboxylate (69.1 mg, 0.148 mmol), 1-ethyl-4-(4,4,5,5-tetramethyl-1,3,2-dioxaborolan-2-yl)-1H-pyrazole (65.7 mg, 0.296 mmol), and PdCl₂(dppf)-CH₂Cl₂ Adduct (12.07 mg, 0.015 mmol) in dioxane (986 µl) was added potassium phosphate, dibasic (222 µl, 0.444 mmol). The suspension was purged with nitrogen for 5 minutes. The vial was sealed and heated at 100° C. for 2 hrs. The reaction was diluted methanol (10 ml), filtered, and concentrated. The resulting brown oil was partitioned between ethyl acetate and water. The organic layer was washed with water and brine, dried with sodium sulfate, filtered, and concentrated to give an oil. The oil was purified via flash chromatography (ISCO silica gel column, 0-100% EtOAc/hexanes) to afford (R)-tert-butyl 4-((7-carbamoyl-2-(1-ethyl-1H-pyrazol-4-yl)imidazo[1,2-b]pyridazin-8-yl)amino)-3,3-dimethylpiperidine-1-carboxylate (62.2 mg, 0.129 mmol, 87% yield) as a white solid. ESI-MS (analytical LCMS Method B): m/z 483.1 ([M+H]+). HPLC (analytical HPLC Method B) Rt: 3.345 min The above-mentioned white solid was taken up in DCM (986 μl) and cooled to 0° C. TFA (11.39 μl, 0.148 mmol) was added. The reaction was allowed to warm to room temperature. After 2 hrs, the reaction solution was concentrated, yielding a yellow oil. The oil was diluted with ethyl acetate, washed successively with saturated sodium bicarbonate solution, water, and saturated sodium chloride solution, dried with sodium sulfate, filtered, and concentrated to afford (R)-8-((3,3-dimethylpiperidin-4-yl)amino)-2-(1-ethyl-1H-pyrazol-4-yl)imidazo[1,2-b]pyridazine-7-carboxamide, TFA (57.8 mg, 0.116 mmol, 79% yield) as a light yellow solid. ESI-MS (analytical LCMS Method B): m/z 383.2 ([M+H]$^+$). HPLC (analytical HPLC Method B) Rt: 2.093 min Step 3: (R)-8-((1-(6-Cyanopyridazin-3-yl)-3,3-dimethylpiperidin-4-yl)amino)-2-(1-ethyl-1H-pyrazol-4-yl)imidazo[1,2-b]pyridazine-7-carboxamide

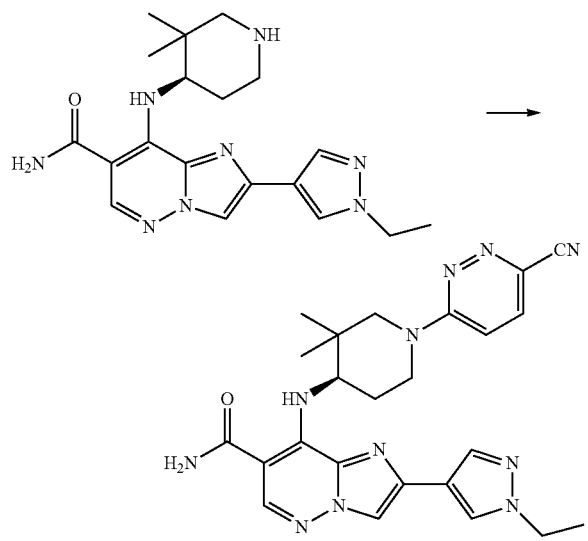

To a solution of (R)-8-((3,3-dimethylpiperidin-4-yl)amino)-2-(1-ethyl-1H-pyrazol-4-yl)imidazo[1,2-b]pyridazine-7-carboxamide, TFA (13 mg, 0.026 mmol) in DMF (105 μl), DIEA (22.87 μl, 0.131 mmol) and 6-chloropyridazine-3-carbonitrile (4.02 mg, 0.029 mmol) were added. The reaction was heated at 90° C. After 2 hrs, the reaction was diluted with methanol (10 ml), filtered, and concentrated. The crude material was purified via preparative LC/MS (Method A). Fractions containing the desired product were combined and dried via centrifugal evaporation to afford the title compound of Example 53 (9.2 mg, 0.019 mmol, 72.4% yield). $^1$H NMR (500 MHz, methanol-d$_4$) δ 8.33 (s, 1H), 7.95 (s, 1H), 7.93 (s, 1H), 7.89 (s, 1H), 7.60 (d, J=9.4 Hz, 1H), 7.22 (d, J=9.9 Hz, 1H), 5.77-5.67 (m, 1H), 4.33 (d, J=12.9 Hz, 1H), 4.26 (q, J=7.4 Hz, 2H), 3.49-3.41 (m, 1H), 3.26-3.19 (m, 1H), 2.35-2.27 (m, 1H), 1.91-1.80 (m, 1H), 1.54 (t, J=7.2 Hz, 3H), 1.43-1.38 (m, 1H), 1.14 (s, 3H), 1.10 (s, 3H). LC/MS (Method F): m/z 486.24 ([M+H]$^+$), Rt. 1.400 min.

Example 54

According to the procedure described for Example 53, Example 54 was prepared from (R)-tert-butyl 4-((2-bromo-7-carbamoylimidazo[1,2-b]pyridazin-8-yl)amino)-3,3-dimethylpiperidine-1-carboxylate (from Step 1 of Example 53) via Suzuki coupling reaction with appropriate boronic acids or boronic acid esters which were commercially available and N-deprotection of N-Boc under conditions similar to Step 2 of Example 53, and arylation with appropriate aryl halides under conditions similar to Step 3 of Example 53.

Example 54 was analyzed using analytical HPLC/LCMS Method F.

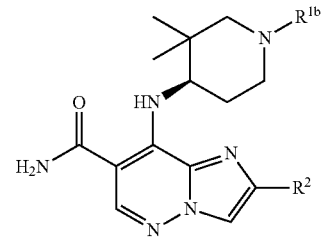

| Ex. No. | Name | —R$^{1b}$ | —R$^2$ | HPLC Rt (minutes) | LCMS [m/z (M + H)] |
|---|---|---|---|---|---|
| 54 | (R)-8-((1-(6-cyanopyridazin-3-yl)-3,3-dimethylpiperidin-4-yl)amino)-2-(1-methyl-1H-pyrazol-4-yl)imidazo[1,2-b]pyridazine-7-carboxamide | N=N with CN | pyrazole with N-Me | 1.38 | 472.22 |

Example 55

Example 55 was prepared following conditions described for Example 45, where (R)-tert-butyl 4-amino-3,3-dimethylpiperidine-1-carboxylate was replaced with (3R,4R)-tert-butyl 4-amino-3-ethylpiperidine-1-carboxylate (Intermediate 5). Example 55 was analyzed using analytical HPLC/LCMS Method F.

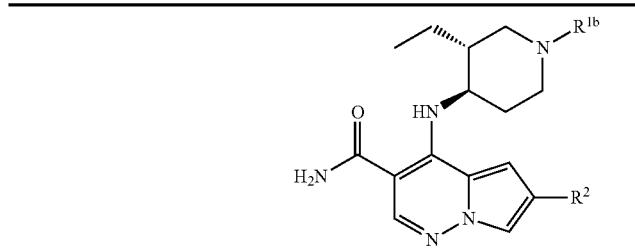

| Ex. No. | Name | —R$^{1b}$ | —R$^2$ | HPLC Rt (minutes) | LCMS [m/z (M + H)] |
|---|---|---|---|---|---|
| 55 | 8-(((3R,4R)-1-(6-cyanopyridazin-3-yl)-3-ethylpiperidin-4-yl)amino)-2-(1-ethyl-1H-pyrazol-4-yl)imidazo[1,2-b]pyridazine-7-carboxamide | [pyridazine-CN] | [1-ethylpyrazole] | 1.440 | 485.20 |

Example 56

8-(((3S,4S)-1-(1-Cyanocyclopropanecarbonyl)-4-(fluoromethyl)pyrrolidin-3-yl)amino)-2-(1-ethyl-1H-pyrazol-4-yl)imidazo[1,2-b]pyridazine-7-carboxamide

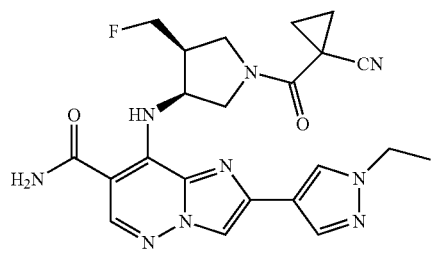 [SMILES: CCn1cc(-c2cn3ncc(C(N)=O)c(N[C@@H]4CN(C(=O)C5(C#N)CC5)C[C@@H]4CF)c3n2)cn1]

Step 1: (3S,4S)-Benzyl 3-((2-bromo-7-carbamoylimidazo[1,2-b]pyridazin-8-yl)amino)-4-(fluoromethyl)pyrrolidine-1-carboxylate

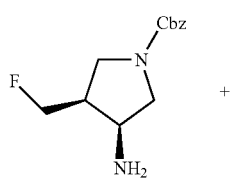

+

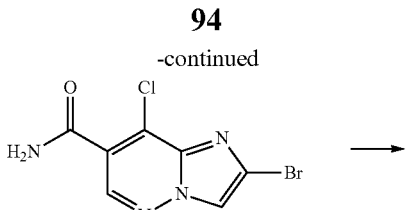

→

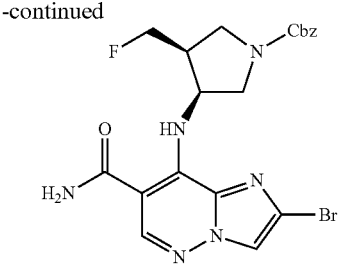

Intermediate 6

A solution of (3S,4S)-benzyl 3-amino-4-(fluoromethyl)pyrrolidine-1-carboxylate, TFA (468 mg, 1.278 mmol) and 2-bromo-8-chloroimidazo[1,2-b]pyridazine-7-carboxamide (352 mg, 1.278 mmol), DIEA (1116 µl, 6.39 mmol) in DMA (5110 µl) was heated at 80° C. for 7 hrs. The reaction mixture was partitioned between ethyl acetate and water. The ethyl acetate solution was washed with saturated NaCl, dried with sodium sulfate, filtered, and concentrated to yield a brown oil. The crude product was purified by flash column (ISCO 12 g, 0-100% EtOAc/hexane) to afford (3S,4S)-benzyl 3-((2-bromo-7-carbamoylimidazo[1,2-b]pyridazin-8-yl)amino)-4-(fluoromethyl)pyrrolidine-1-carboxylate (615.6 mg, 1.253 mmol, 98% yield) as a faint yellow solid. ESI-MS (analytical LCMS Method B): m/z 493.2 ([M+H]$^+$). HPLC (analytical HPLC Method B) Rt: 3.148 min.

Step 2: (3S,4S)-tert-Butyl 3-((2-bromo-7-carbam-oylimidazo[1,2-b]pyridazin-8-yl)amino)-4-(fluorom-ethyl)pyrrolidine-1-carboxylate Step 3: (3S,4S)-tert-Butyl 3-((7-carbamoyl-2-(1-ethyl-1H-pyrazol-4-yl)imidazo[1,2-b]pyridazin-8-yl)amino)-4-(fluoromethyl)pyrrolidine-1-carboxylate

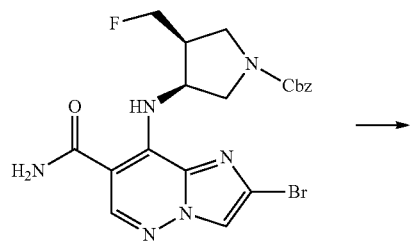

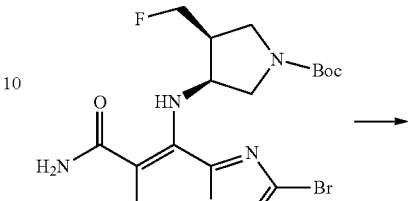

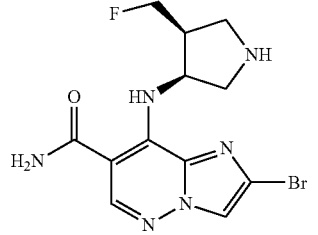

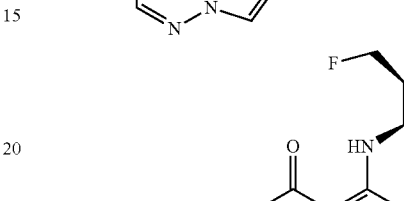

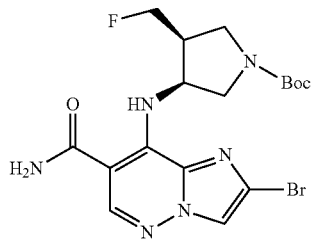

To a suspension of (3S,4S)-benzyl 3-((2-bromo-7-carbamoylimidazo[1,2-b]pyridazin-8-yl)amino)-4-(fluoromethyl)pyrrolidine-1-carboxylate (240 mg, 0.488 mmol) in acetonitrile (3 ml) at 0° C. was added iodotrimethylsilane (0.266 ml, 1.954 mmol) dropwise. The reaction mixture was stirred at 0° C. for 10 min and at room temperature for 1.5 h. The reaction was cooled to 0° C. and quenched with MeOH (2 ml). The resulting suspension was stirred at 0° C. for 30 min, filtered, washed with ethyl ether, and dried under vacuum to afford 2-bromo-8-(((3S,4S)-4-(fluoromethyl)pyrrolidin-3-yl)amino)imidazo[1,2-b]pyridazine-7-carboxamide, hydroiodide as an off-white solid. ESI-MS (analytical LCMS Method A): m/z 357.0 ([M+H]+).

To a suspension of the above-mentioned off-white solid in DCM (5 ml) was added TEA (4 eq), followed by slow addition of a solution of BOC₂O (209 mg 1.00 mmol) in DCM (5 ml). The reaction was stirred at room temperature for 5 h. The reaction mixture was partitioned between water and DCM. The organic phase was washed with brine, dried (Na₂SO₄) and concentrated. The crude product was purified via flash chromatography (ISCO silica gel column, 20-60% EtOAc/hexane) affording (3S,4S)-tert-butyl 3-((2-bromo-7-carbamoylimidazo[1,2-b]pyridazin-8-yl)amino)-4-(fluoromethyl) pyrrolidine-1-carboxylate (141 mg, 0.308 mmol, 63.1% yield) as a white solid. ESI-MS (analytical LCMS Method A): m/z 457.0 ([M+H]+). HPLC (analytical HPLC Method A) Rt: 3.60 min.

A solution of (3S,4S)-tert-butyl 3-((2-bromo-7-carbamoylimidazo[1,2-b]pyridazin-8-yl)amino)-4-(fluoromethyl) pyrrolidine-1-carboxylate (22.2 mg, 0.049 mmol), 1-ethyl-4-(4,4,5,5-tetramethyl-1,3,2-dioxaborolan-2-yl)-1H-pyrazole (21.56 mg, 0.097 mmol), PdCl₂(dppf) CH₂Cl₂ Adduct (1:1) (3.99 mg, 4.85 µmol) in dioxane (0.5 ml) and 2M aq K₃PO₄ (0.073 ml, 0.146 mmol) in dioxane (0.5 ml) in a reaction vial was purged with N₂ for 2 min. The reaction mixture was sealed and heated at 100° C. for 120 min. The reaction mixture was partitioned between EtOAc and water. The organic phase was washed with brine, filtered through CELITE®, dried (Na₂SO₄) and concentrated. The crude product was purified by flash column (ISCO 12 g-column, 20-80% EtOAc/hexane over 15 min) to afford (3S,4S)-tert-butyl 3-((7-carbamoyl-2-(1-ethyl-1H-pyrazol-4-yl)imidazo [1,2-b]pyridazin-8-yl)amino)-4-(fluoromethyl)pyrrolidine-1-carboxylate (15 mg, 0.032 mmol, 65.4% yield) as a white solid. ESI-MS (Method A): m/z 473.4 ([M+H]+).

Step 4: 2-(1-Ethyl-1H-pyrazol-4-yl)-8-(((3S,4S)-4-(fluoromethyl)pyrrolidin-3-yl)amino)imidazo[1,2-b]pyridazine-7-carboxamide, 2 TFA

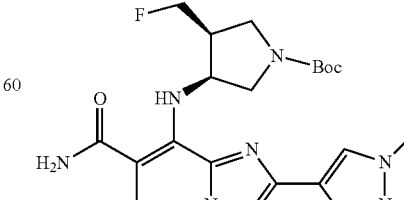

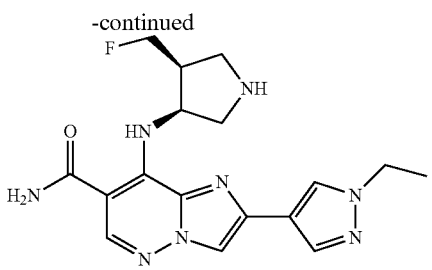

A solution of (3S,4S)-tert-butyl 3-((7-carbamoyl-2-(1-ethyl-1H-pyrazol-4-yl)imidazo[1,2-b]pyridazin-8-yl)amino)-4-(fluoromethyl)pyrrolidine-1-carboxylate (15 mg, 0.032 mmol) in DCM (0.5 ml) was treated with TFA (0.024 ml, 0.317 mmol) at room temperature for 2 h. The reaction mixture was concentrated to give 2-(1-ethyl-1H-pyrazol-4-yl)-8-(((3S,4S)-4-(fluoromethyl)pyrrolidin-3-yl)amino)imidazo[1,2-b]pyridazine-7-carboxamide, 2 TFA (15.1 mg, 0.025 mmol, 79% yield) as a white solid. ESI-MS (Method A): m/z 373.3 ([M+H]$^+$).

Step 5: 8-(((3S,4S)-1-(1-Cyanocyclopropanecarbonyl)-4-(fluoromethyl)pyrrolidin-3-yl)amino)-2-(1-ethyl-1H-pyrazol-4-yl)imidazo[1,2-b]pyridazine-7-carboxamide

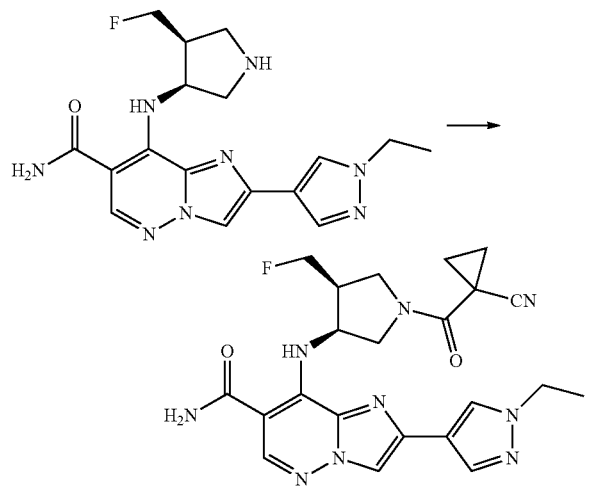

A solution of 2-(1-ethyl-1H-pyrazol-4-yl)-8-(((3S,4S)-4-(fluoromethyl)pyrrolidin-3-yl)amino)imidazo[1,2-b]pyridazine-7-carboxamide, TFA (15 mg, 0.031 mmol), 1-cyanocyclopropanecarboxylic acid (6.85 mg, 0.062 mmol), HATU (17.59 mg, 0.046 mmol) and DIPEA (0.027 ml, 0.154 mmol) in DMF (0.4 ml) in a reaction vial was stirred at room temperature for 135 min. The crude material was purified via preparative LC/MS (Method A). Fractions containing the desired product were combined and dried via centrifugal evaporation to afford the title compound of Example 56 (8.5 mg, 59.2% yield). $^1$H NMR (500 MHz, DMSO-d$_6$, two rotamers) δ 10.74 (d, J=8.9 Hz, 1H), 10.70 (d, J=8.4 Hz, 1H), 8.49 (br. s., 1H), 8.47 (br. s., 1H), 8.29 (br. s., 1H), 8.28 (br. s., 1H), 8.17 (s, 2H), 8.02 (br. s., 2H), 7.90 (s, 2H), 7.43 (br. s., 2H), 6.14 (br. s., 1H), 6.06 (br. s., 1H), 4.75 (d, J=5.4 Hz, 1H), 4.69 (d, J=6.4 Hz, 2H), 4.59 (d, J=6.9 Hz, 2H), 4.29 (dd, J=9.9, 5.9 Hz, 1H), 4.17 (q, J=7.4 Hz, 4H), 3.91-3.80 (m, 3H), 3.76 (dd, J=12.4, 8.9 Hz, 1H), 3.55 (d, J=10.9 Hz, 1H), 3.47 (dd, J=12.4, 7.4 Hz, 1H), 3.15 (dd, J=13.1, 6.2 Hz, 1H), 3.10-2.99 (m, 1H), 1.63 (br. s., 2H), 1.60-1.49 (m, 6H), 1.40 (t, J=7.2 Hz, 6H). HPLC/LCMS (Method F): m/z 466.21 ([M+H]$^+$), Rt. 1.118 min.

Example 57

8-(((3S,4S)-1-(1-Cyanocyclopropanecarbonyl)-4-(fluoromethyl)pyrrolidin-3-yl)amino)-2-(1-methyl-1H-pyrazol-4-yl)imidazo[1,2-b]pyridazine-7-carboxamide According to the procedure described for Example 56, Example 57 was prepared from (3S,4S)-tert-butyl 3-((2-bromo-7-carbamoylimidazo[1,2-b]pyridazin-8-yl)amino)-4-(fluoromethyl)pyrrolidine-1-carboxylate (from Step 2 of Example 56) via Suzuki coupling reaction with 1-ethyl-4-(4,4,5,5-tetramethyl-1,3,2-dioxaborolan-2-yl)-1H-pyrazole under conditions similar to Step 3 of Example 56, deprotection of N-Boc under conditions similar to Step 3 of Example 56 and amidation with 1-cyanocyclopropanecarboxylic acid under conditions similar to Step 5 of Example 56.

Example 57 was analyzed using analytical HPLC/LCMS Method F.

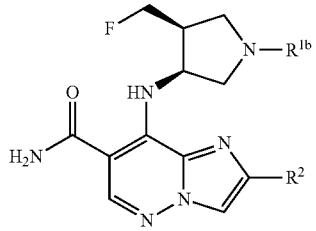

| Ex. No. | Name | —R$^{1b}$ | —R$^2$ | HPLC Rt (minutes) | LCMS [m/z (M + H)] |
|---|---|---|---|---|---|
| 57 | 8-(((3S,4S)-1-(1-cyanocyclopropanecarbonyl)-4-(fluoromethyl)pyrrolidin-3-yl)amino)-2-(1-methyl-1H-pyrazol-4-yl)imidazo[1,2-b]pyridazine-7-carboxamide | ![structure with CN cyclopropane carbonyl] | ![methylpyrazole] | 1.089 | 452.20 |

Examples 58-64

Examples 58-64 were prepared from 2-bromo-8-(((3S,4S)-4-(fluoromethyl)pyrrolidin-3-yl)amino)imidazo[1,2-b]pyridazine-7-carboxamide, hydroiodide (from Step 2 of Example 56) via amidation with appropriate acids following conditions analogous to Step 5 of Example 56 and Suzuki coupling reaction with appropriate boronic acids which were commercially available following conditions analogous to Step 4 of Example 56.

Examples 58-64 were analyzed using analytical HPLC/LCMS Method F.

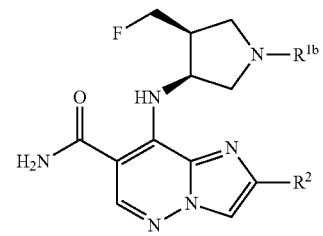

| Ex. No. | Name | —R$^{1b}$ | —R$^2$ | HPLC Rt (minutes) | LCMS [m/z] (M + H)] |
|---|---|---|---|---|---|
| 58 | 8-(((3S,4S)-1-(1-cyanocyclopropanecarbonyl)-4-(fluoromethyl)pyrrolidin-3-yl)amino)-2-(1-propyl-1H-pyrazol-4-yl)imidazo[1,2-b]pyridazine-7-carboxamide | | | 1.327 | 480.23 |
| 59 | 8-(((3S,4S)-1-(1-cyanocyclopropanecarbonyl)-4-(fluoromethyl)pyrrolidin-3-yl)amino)-2-(1-isopropyl-1H-pyrazol-4-yl)imidazo[1,2-b]pyridazine-7-carboxamide | | | 1.316 | 480.23 |
| 60 | 8-(((3S,4S)-1-(1-cyanocyclopropanecarbonyl)-4-(fluoromethyl)pyrrolidin-3-yl)amino)-2-(1-cyclopropyl-1H-pyrazol-4-yl)imidazo[1,2-b]pyridazine-7-carboxamide | | | 1.259 | 478.21 |
| 61 | 8-(((3S,4S)-1-(1-cyanocyclopropanecarbonyl)-4-(fluoromethyl)pyrrolidin-3-yl)amino)-2-(1-(difluoromethyl)-1H-pyrazol-4-yl)imidazo[1,2-b]pyridazine-7-carboxamide | | | 1.250 | 487.2 |
| 62 | 8-(((3S,4S)-1-(1-cyanocyclopropanecarbonyl)-4-(fluoromethyl)pyrrolidin-3-yl)amino)-2-(1-methyl-1H-indazol-5-yl)imidazo[1,2-b]pyridazine-7-carboxamide | | | 1.447 | 546.22 |
| 63 | 8-(((3S,4S)-1-(1-cyanocyclopropanecarbonyl)-4-(fluoromethyl)pyrrolidin-3-yl)amino)-2-(2-methylpyridin-4-yl)imidazo[1,2-b]pyridazine-7-carboxamide | | | 1.003 | 463.20 |
| 64 | 8-(((3S,4S)-1-(1-cyanocyclopropanecarbonyl)-4-(fluoromethyl)pyrrolidin-3-yl)amino)-2-(2-oxoindolin-6-yl)imidazo[1,2-b]pyridazine-7-carboxamide | | | 1.193 | 503.19 |

Examples 65-69

Examples 65-69 were prepared from 2-bromo-8-(((3S, 4S)-4-ethylpyrrolidin-3-yl)amino)imidazo[1,2-b]pyridazine-7-carboxamide (from Step 2 of Example 36) via amidation with appropriate acids following conditions analogous to Step 5 of Example 36 and Suzuki coupling reaction with appropriate boronic acids which were commercially available or boronic acid esters selected from Intermediates 7-11, following conditions analogous to Step 4 of Example 36.

Examples 65-69 were analyzed using analytical HPLC/LCMS Method F.

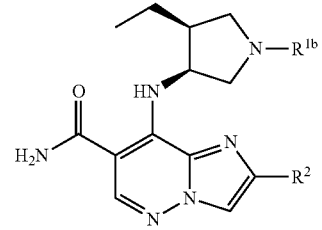

| Ex. No. | Name | —R$^{1b}$ | —R$^2$ | HPLC Rt (minutes) | LCMS [m/z (M + H)] |
|---|---|---|---|---|---|
| 65 | 8-(((3S,4S)-1-(1-cyanocyclopropanecarbonyl)-4-ethylpyrrolidin-3-yl)amino)-2-(1-(difluoromethyl)-1H-pyrazol-4-yl)imidazo[1,2-b]pyridazine-7-carboxamide | | | 1.45 | 483.2 |
| 66 | 8-(((3S,4S)-1-(1-cyanocyclopropanecarbonyl)-4-ethylpyrrolidin-3-yl)amino)-2-(1-((S)-3,3,3-trifluoro-2-hydroxypropyl)-1H-pyrazol-4-yl)imidazo[1,2-b]pyridazine-7-carboxamide | | | 1.291 | 460.22 |
| 67 | 8-(((3S,4S)-1-(1-cyanocyclopropanecarbonyl)-4-ethylpyrrolidin-3-yl)amino)-2-(1-(2-hydroxy-2-methylpropyl)-1H-pyrazol-4-yl)imidazo[1,2-b]pyridazine-7-carboxamide | | | 1.295 | 506.26 |
| 68 | 8-(((3S,4S)-1-(1-cyanocyclopropanecarbonyl)-4-ethylpyrrolidin-3-yl)amino)-2-(1-((S)-2-hydroxypropyl)-1H-pyrazol-4-yl)imidazo[1,2-b]pyridazine-7-carboxamide | | | 1.224 | 492.25 |
| 69 | 8-(((3S,4S)-1-(1-cyanocyclopropanecarbonyl)-4-ethylpyrrolidin-3-yl)amino)-2-(1-((R)-2-hydroxypropyl)-1H-pyrazol-4-yl)imidazo[1,2-b]pyridazine-7-carboxamide | | | 1.222 | 492.25 |

Example 70

8-(((3S,4S)-1-(1-Cyanocyclopropanecarbonyl)-4-methylpyrrolidin-3-yl)amino)-2-(6-methoxypyridin-2-yl)imidazo[1,2-b]pyridazine-7-carboxamide

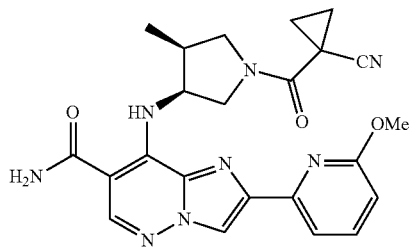 [SMILES: COc1cccc(-c2cn3ncc(C(N)=O)c(N[C@@H]4CN(C(=O)C5(C#N)CC5)C[C@@H]4C)c3n2)n1]

Step 1: 2-Bromo-8-(((3S,4S)-1-(1-cyanocyclopropanecarbonyl)-4-methylpyrrolidin-3-yl)amino)imidazo[1,2-b]pyridazine-7-carboxamide

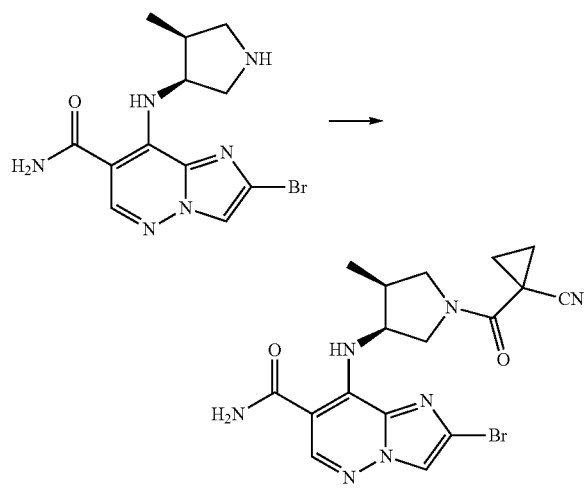

To a solution of 1-cyanocyclopropanecarboxylic acid (0.264 g, 2.380 mmol) in DCM (15.9 ml) were added DIEA (2.079 ml, 11.90 mmol), and BOP (1.263 g, 2.86 mmol). The solution was stirred at room temperature for 10 minutes, and 2-bromo-8-(((3S,4S)-4-methylpyrrolidin-3-yl)amino) imidazo[1,2-b]pyridazine-7-carboxamide, hydrobromide (from Step 2 of Example 1, 1.00 g, 2.380 mmol) was added. The reaction was stirred for 1 hr. After removal of the solvent, the crude product was purified by flash chromatography (ISCO, prepacked silica gel column eluting with 0-5% EtOAc/MeOH over 15 column volumes) to afford 2-bromo-8-(((3S,4S)-1-(1-cyanocyclopropanecarbonyl)-4-methylpyrrolidin-3-yl)amino)imidazo[1,2-b]pyridazine-7-carboxamide as a white solid, 1.01 g, 2.336 mmol, 98% yield. ESI-MS (Method B): m/z 434.1 ([M+H]$^+$). HPLC (Method B) Rt: 2.505 min.

Step 2: 8-(((3S,4S)-1-(1-Cyanocyclopropanecarbonyl)-4-methylpyrrolidin-3-yl)amino)-2-(6-methoxypyridin-2-yl)imidazo[1,2-b]pyridazine-7-carboxamide

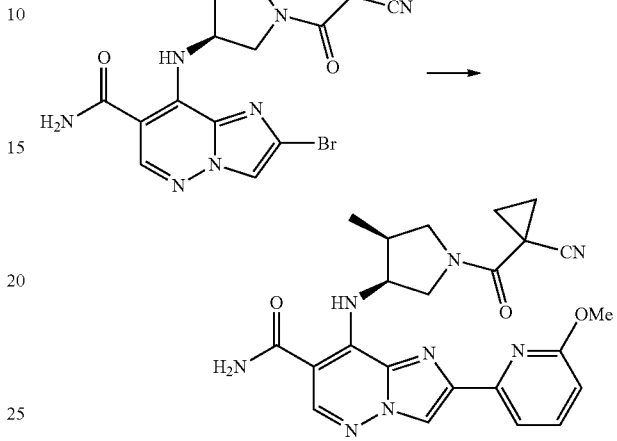

A solution of 2-bromo-8-(((3S,4S)-1-(1-cyanocyclopropanecarbonyl)-4-methylpyrrolidin-3-yl)amino)imidazo[1,2-b]pyridazine-7-carboxamide (30 mg, 0.069 mmol), 2-methoxy-6-(4,4,5,5-tetramethyl-1,3,2-dioxaborolan-2-yl)pyridine (40.8 mg, 0.174 mmol), copper (I) chloride (7.21 mg, 0.073 mmol), cesium carbonate (45.2 mg, 0.139 mmol) and PdCl$_2$(dppf)-CH$_2$Cl$_2$ Adduct (6.23 mg, 7.63 µmol) in DMF (694 µl) in a reaction vial was purged with nitrogen for 5 minutes. The vial was sealed and heated at 150° C. for 30 minutes. The reaction was diluted methanol (10 ml), filtered through CELITE® and concentrated. The resulting crude oil was partitioned between EtOAc and water. The organic phase was washed with brine, dried (Na$_2$SO$_4$) and concentrated. The crude material was purified via preparative LC/MS (Method A). Fractions containing the desired product were combined and dried via centrifugal evaporation to afford the title compound of Example 70 (3.4 mg, 7.38 µmol, 10.64% yield) as a white solid. $^1$H NMR (500 MHz, deuterated 1:1 methanol:chloroform) δ 8.42-8.36 (m, 2H), 7.77-7.69 (m, 2H), 6.73 (d, J=7.9 Hz, 1H), 4.35-4.25 (m, 2H), 4.02 (s, 3H), 3.90-3.75 (m, 2H), 3.41 (dd, J=12.1, 8.7 Hz, 1H), 2.93-2.75 (m, 1H), 1.82-1.72 (m, 1H), 1.68-1.50 (m, 3H), 1.24 (dd, J=14.9, 6.9 Hz, 3H). LC/MS (Method F): m/z 461.10 ([M+H]$^+$), Rt. 1.588 min.

Examples 71-72

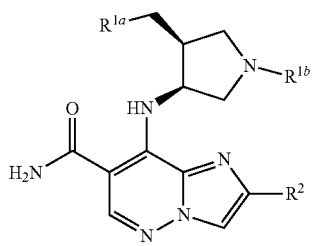

Example 71 was prepared from 2-bromo-8-(((3S,4S)-4-(fluoromethyl)pyrrolidin-3-yl)amino)imidazo[1,2-b]pyridazine-7-carboxamide, hydroiodide (first product from step 2 of Example 56) via amidation with 2-cyano-2-methylpropanoic acid following conditions analogous to Step 1 of Example 70, Suzuki coupling reaction with tert-butyl 4-(4,4,5,5-tetramethyl-1,3,2-dioxaborolan-2-yl)-1H-pyrazole-1-carboxylate following conditions analogous to Step 4 of Example 36, and subsequent removal of Boc group with TFA. Example 72 was prepared in an analogous way to Example 71, via amidation of 2-bromo-8-(((3S,4S)-1-(1-cyanocyclopropanecarbonyl)-4-ethylpyrrolidin-3-yl)amino)imidazo[1,2-b]pyridazine-7-carboxamide (from Step 2 of Example 36) with 1-cyanocyclopropanecarboxylic acid, Suzuki coupling reaction with tert-butyl 4-(4,4,5,5-tetramethyl-1,3,2-dioxaborolan-2-yl)-1H-pyrazole-1-carboxylate, and subsequent removal of Boc group with TFA.

Examples 71-72 were analyzed using analytical HPLC/LCMS Method F.

| Ex. No | Name | —$R^{1a}$ | —$R^{1b}$ | —$R^2$ | HPLC Rt (minutes) |
|---|---|---|---|---|---|
| 71 | 8-(((3S,4S)-1-(2-cyano-2-methylpropanoyl)-4-(fluoromethyl)pyrrolidin-3-yl)amino)-2-(1H-pyrazol-4-yl)imidazo[1,2-b]pyridazine-7-carboxamide | F | ![structure with CN] | ![pyrazole NH] | 1.025 |
| 72 | 8-(((3S,4S)-1-(1-cyanocyclopropanecarbonyl)-4-ethylpyrrolidin-3-yl)amino)-2-(1H-pyrazol-4-yl)imidazo[1,2-b]pyridazine-7-carboxamide | CH3 | ![cyclopropyl CN] | ![pyrazole NH] | 2.488 |

Example 73

8-(((3S,4S)-1-(1-Cyanocyclopropanecarbonyl)-4-ethylpyrrolidin-3-yl)amino)-2-(1-methyl-$d_3$)-1H-pyrazol-4-yl)imidazo[1,2-b]pyridazine-7-carboxamide

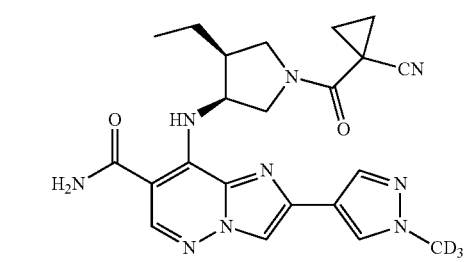 [SMILES: [2H]C([2H])([2H])n1cc(-c2cn3ncc(C(N)=O)c(N[C@@H]4CN(C(=O)C5(C#N)CC5)C[C@@H]4CC)c3n2)cn1]

Step 1: 1-(Methyl-$d_3$)-4-(4,4,5,5-tetramethyl-1,3,2-dioxaborolan-2-yl)-1H-pyrazole

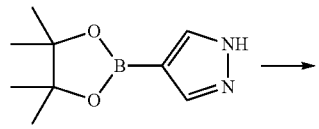

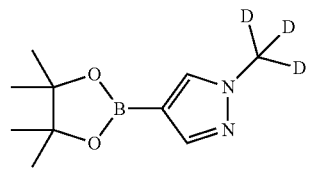

To an suspension of 4-(4,4,5,5-tetramethyl-1,3,2-dioxaborolan-2-yl)-1H-pyrazole (1.8 g, 9.28 mmol) and potassium carbonate (6.41 g, 46.40 mmol) in acetonitrile (34.5 ml), iodomethane-$d_3$ (0.866 ml, 13.9 mmol) was added. The reaction mixture was stirred at 35° C. overnight. The suspension was diluted with DCM and filtered. The potassium carbonate filter cake was washed with DCM. Evaporation of the DCM filtrate yielded a faint yellow solid. The solid was triturated with DCM, filtered, and concentrated under reduced pressure to give 1-(methyl-$d_3$)-4-(4,4,5,5-tetramethyl-1,3,2-dioxaborolan-2-yl)-1H-pyrazole (1.46 g, 6.92 mmol, 74.6% yield) was a faint yellow solid. The crude product was carried forward. ESI-MS (Method B): m/z 212.3 ([M+H]$^+$). HPLC (Method B) Rt: 1.983 min.

Step 2: 8-(((3S,4S)-1-(1-Cyanocyclopropanecarbonyl)-4-ethylpyrrolidin-3-yl)amino)-2-(1-methyl-$d_3$)-1H-pyrazol-4-yl)imidazo[1,2-b]pyridazine-7-carboxamide

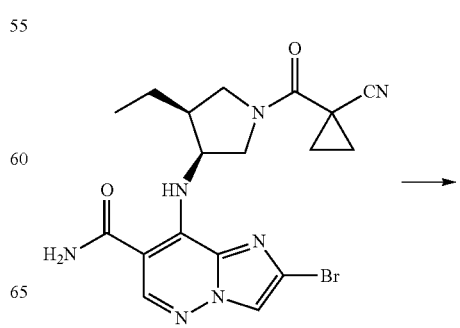

-continued

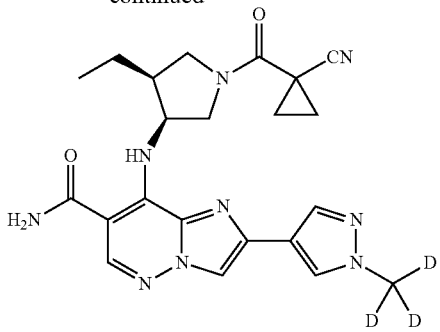

A solution of 2-bromo-8-(((3S,4S)-1-(1-cyanocyclopropanecarbonyl)-4-ethylpyrrolidin-3-yl)amino)imidazo[1,2-b]pyridazine-7-carboxamide (1.00 g, 2.241 mmol), 1-(methyl-$d_3$)-4-(4,4,5,5-tetramethyl-1,3,2-dioxaborolan-2-yl)-1H-pyrazole (1.419 g, 6.72 mmol), and PdCl$_2$(dppf)-CH$_2$Cl$_2$ adduct (0.183 g, 0.224 mmol) in dioxane (14.94 ml) and 2M aq. potassium phosphate, tribasic (3.36 ml, 6.72 mmol) in a reaction vial was purged with nitrogen for 5 minutes. The vial was sealed and heated at 90° C. for 1 hr. The reaction was diluted with methanol (10 ml), filtered through CELITE® and concentrated. The crude oil was partitioned between EtOAc and water. The organic phase was washed with water and brine, dried (Na$_2$SO$_4$) and concentrated. The crude material was purified via flash chromatography (Isco, prepacked silica gel column eluting with 0-7% DCM-MeOH over 20 column volumes) to afford the title compound of Example 73 (516 mg, 1.134 mmol, 50.6% yield) as a white solid. $^1$H NMR (400 MHz, methanol-$d_4$) δ 8.36 (d, J=3.7 Hz, 1H), 8.04 (d, J=7.7 Hz, 2H), 7.90 (d, J=7.0 Hz, 1H), 6.06 (br. s., 1H), 4.38-4.17 (m, 2H), 3.90-3.70 (m, 2H), 2.71-2.49 (m, 1H), 1.78-1.45 (m, 6H), 1.07-0.94 (m, 3H). ESI-MS (Method B): m/z 451.4 ([M+H]$^+$). HPLC (Method B) Rt: 2.663 min.

Example 74

8-(((3S,4S)-1-(1-Cyanocyclopropanecarbonyl)-4-(ethyl-$d_5$)pyrrolidin-3-yl)amino)-2-(1-methyl-1H-pyrazol-4-yl)imidazo[1,2-b]pyridazine-7-carboxamide

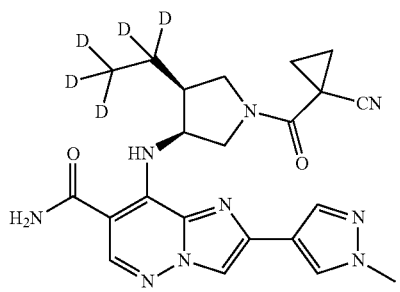 [SMILES: [2H]C([2H])([2H])C([2H])([2H])[C@H]1CN(C(=O)C2(C#N)CC2)C[C@H]1Nc1c(C(N)=O)cnn2cc(-c3cnn(C)c3)nc12]

Step 1: (3SR,4RS)-Benzyl 3-(ethyl-$d_5$)-4-hydroxypyrrolidine-1-carboxylate

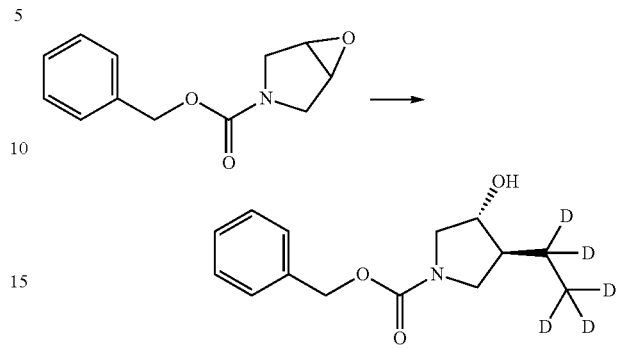

Magnesium turnings (8.95 g, 368 mmol) were polished by stirring the turnings overnight under nitrogen. THF (263 ml) was added, and the stirring solution was cooled to 0° C. A THF solution of bromoethane-$d_5$ (30 g, 263 mmol) was added dropwise. The clear, colorless solution was stirred for 90 min and became a grayish cloudy solution. The formed (ethyl-$d_5$)magnesium bromide was added dropwise into a solution of benzyl 6-oxa-3-azabicyclo[3.1.0]hexane-3-carboxylate (22.5 g, 103 mmol 4.0 g, 18.25 mmol) and copper (I) bromide-dimethyl sulfide complex (21.10 g, 103 mmol 3.75 g, 18.25 mmol) in THF (411 ml 73.0 ml) pre-cooled at −40° C. The reaction was stirred at −40° C. for 2 h and then warmed to 0° C. The solution was quenched with (sat.) NH$_4$Cl and continued stirring for 30 min. The product mixture was partitioned between EtOAc and water. The organic phase was washed with (sat.) NH$_4$Cl, brine, filtered, dried (Na$_2$SO$_4$) and concentrated to give a yellow oil. The crude product was purified by flash column (ISCO 15 g-column, 0-60% EtOAc/hexane) to afford (3SR,4RS)-benzyl 3-(ethyl-$d_5$)-4-hydroxypyrrolidine-1-carboxylate (20.1 g, 77% yield) as a clear, colorless oil. ESI-MS (Method A): m/z 255.3 ([M+H]$^+$). HPLC (Method B) Rt: 2.345 min.

Step 2: (3SR,4RS)-Benzyl 3-(ethyl-$d_5$)-4-(tosyloxy)pyrrolidine-1-carboxylate

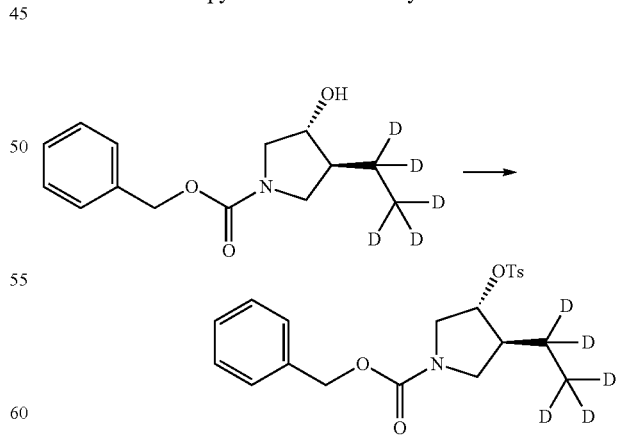

To a solution of (3SR,4RS)-benzyl 3-(ethyl-$d_5$)-4-hydroxypyrrolidine-1-carboxylate (20.7 g, 81 mmol) in pyridine (80 ml) was added tosyl-Cl (20.2 g, 106 mmol). The reaction was stirred at room temperature overnight. The reaction solution was concentrated under reduced pressure, forming a white suspension. The suspension was diluted with EtOAc and filtered. The EtOAc filtrate was washed successively with water, 1.0N HCl, water, potassium phosphate and (sat.) sodium chloride. The EtOAc layer was dried (Na$_2$SO$_4$), filtered, and concentrated to give a colorless oil. The crude product was purified by flash chromatography (ISCO, prepacked silica gel 80 g-column eluting with 0-60% EtOAc/hexane) to afford (3SR,4RS)-benzyl 3-(ethyl-d$_5$)-4-(tosyloxy)pyrrolidine-1-carboxylate (24.6 g, 60.2 mmol, 74% yield). ESI-MS (Method A): m/z 409.3 ([M+H]$^+$). HPLC (Method B) Rt: 3.123 min.

Step 3: (3SR,4SR)-Benzyl 3-azido-4-(ethyl-d$_5$)pyrrolidine-1-carboxylate

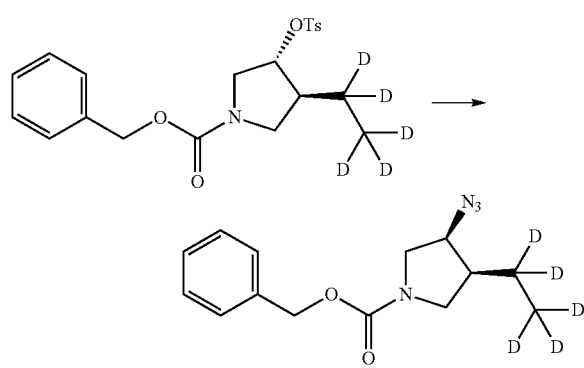

A solution of (3SR,4RS)-benzyl 3-(ethyl-d$_5$)-4-(tosyloxy)pyrrolidine-1-carboxylate (24.6 g, 60.2 mmol) and sodium azide (9.78 g, 150.6 mmol) in DMF (50 ml) was purged with nitrogen for 2 min. and then heated at 85° C. for 5 hrs. The reaction was cooled to room temperature and diluted with 1:1 EtOAc/(sat.) sodium bicarbonate water (200 ml/200 ml). The EtOAc layer was washed with water and (sat.) sodium chloride, dried over sodium sulfate, filtered, and concentrated under reduced pressure, yielding a faint yellow oil. The crude product was purified by flash chromatography (ISCO, prepacked silica gel 80 g column eluting with 0-60% EtOAc/hexane) to afford (3SR,4SR)-benzyl 3-azido-4-(ethyl-d$_5$)pyrrolidine-1-carboxylate (14.6 g, 52.3 mmol, 87% yield) as a clear, colorless oil. ESI-MS (Method A): m/z 280.1 ([M+H]$^+$). HPLC (Method B) Rt: 2.991 min.

Step 4: (3SR,4SR)-Benzyl 3-amino-4-(ethyl-d$_5$)-pyrrolidine-1-carboxylate

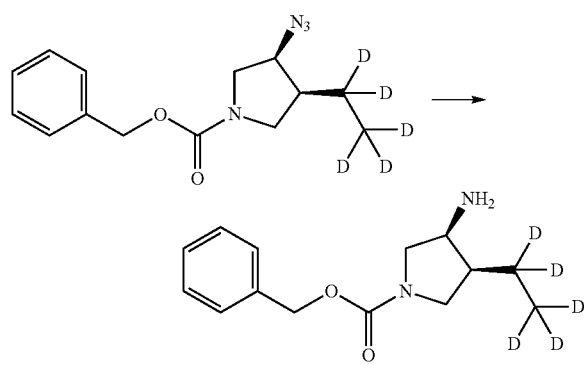

Triphenylphosphine (14.4 g, 54.9 mmol) was added to a solution of (3SR,4SR)-benzyl 3-azido-4-(ethyl-d$_5$)-pyrrolidine-1-carboxylate (14.6 g, 52.3 mmol) in acetonitrile (198 ml) and water (19.8 ml). The reaction was stirred at room temperature for 30 minutes and then was heated at 60° C. overnight. The reaction was cooled to room temperature and concentrated. The crude product mixture was taken into 0.5 N HCl (~150 ml, ca pH=1). The solution was washed with EtOAc (3×100 ml) to remove the triphenylphosphine oxide and residual triphenylphosphine. The aqueous layer was cooled to 0° C. and was adjusted to pH 10 with 1.0N NaOH. The product was extracted with DCM (3×100 ml). The extracts were combined, washed with (sat.) sodium chloride, dried over magnesium sulfate, filtered and concentrated to give (3SR,4SR)-benzyl 3-amino-4-(ethyl-d$_5$)-pyrrolidine-1-carboxylate (12.36 g, 48.8 mmol, 93% yield) as a clear, colorless oil. ESI-MS (Method A): m/z 254.1 ([M+H]$^+$).

Step 5: (3S,4S)-Benzyl 3-((2-bromo-7-carbamoylimidazo[1,2-b]pyridazin-8-yl)amino)-4-(ethyl-d$_5$)pyrrolidine-1-carboxylate

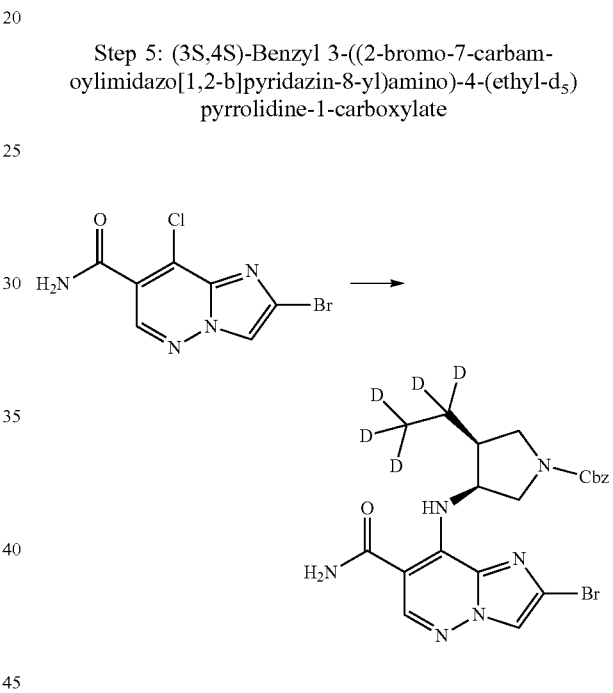

A solution of (3S,4S)-benzyl 3-amino-4-(ethyl-d$_5$)pyrrolidine-1-carboxylate (6.25 g, 24.67 mmol), 2-bromo-8-chloroimidazo[1,2-b]pyridazine-7-carboxamide (6.80 g, 24.67 mmol) and DIEA (12.93 ml, 74.0 mmol) in DMA (32.9 ml) was heated at 80° C. for 3 hrs. The reaction solution was partitioned between ethyl acetate (400 ml) and water. The ethyl acetate layer was washed with 10% LiCl (2×100 ml), water, and brine; dried with sodium sulfate, filtered, and concentrated to half of its volume. The resulting suspension was filtered and the crude product was collected as a light tan solid. The filtrate was diluted with ethyl acetate (100 ml), concentrated to half of its volume and filtered. This process was repeated 3 times to collect the additional product. The combined crude product was purified via flash chromatography (Isco, prepacked silica gel column eluting with 0-100% EtOAc-hexanes over 18 column volumes) to give (3S,4S)-benzyl 3-((2-bromo-7-carbamoylimidazo[1,2-b]pyridazin-8-yl)amino)-4-(ethyl-d$_5$)pyrrolidine-1-carboxylate (9.84 g, 19.98 mmol, 81% yield) as a faint yellow solid. ESI-MS (Method A): m/z 494.1 ([M+H]$^+$). HPLC (Method B) Rt: 3.380 min.

Step 6: 2-Bromo-8-(((3S,4S)-4-(ethyl-d₅)pyrrolidin-3-yl)amino)imidazo[1,2-b]pyridazine-7-carboxamide, hydroiodide

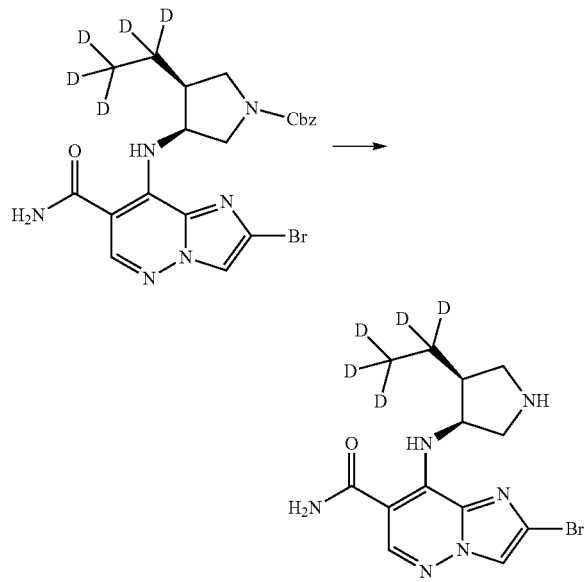

TMS-I (1.015 ml, 7.46 mmol) was dropwise added to a solution of (3S,4S)-benzyl 3-((2-bromo-7-carbamoylimidazo[1,2-b]pyridazin-8-yl)amino)-4-(ethyl-d₅)pyrrolidine-1-carboxylate (1.224 g, 2.486 mmol) in acetonitrile (16.6 ml) at 0° C. The resulting yellow solution was stirred at 0° C. for 10 minutes, then at room temperature for 2 h. The reaction was cooled to 0° C., and was quenched with methanol (1.00 ml). The resulting suspension was stirred for 30 minutes. The suspension was filtered, washed with diethyl ether, and dried under vacuum, yielding 2-bromo-8-(((3S,4S)-4-(ethyl-d₅)-pyrrolidin-3-yl)amino)imidazo[1,2-b]pyridazine-7-carboxamide, hydroiodide (1.209 g, 2.487 mmol, 100% yield) as a light yellow solid. ESI-MS (Method A): m/z 360.2 ([M+H]⁺). HPLC (Method B) Rt: 1.707 min.

Step 7: 2-Bromo-8-(((3S,4S)-1-(1-cyanocyclopropanecarbonyl)-4-(ethyl-d₅)-pyrrolidin-3-yl)amino)imidazo[1,2-b]pyridazine-7-carboxamide

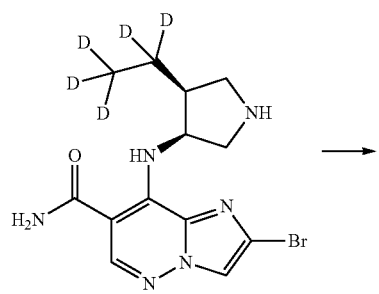

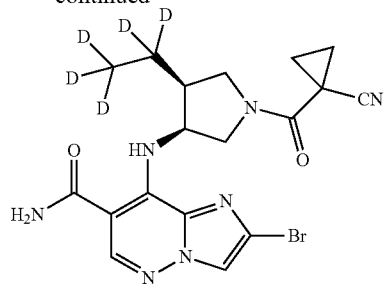

A solution of 1-cyanocyclopropanecarboxylic acid (0.412 g, 3.71 mmol), DIEA (2.95 ml, 16.87 mmol) and BOP (1.791 g, 4.05 mmol) in DCM (20.5 ml) and DMF (2.045 ml) was stirred at room temperature for 10 minutes, by which time 2-bromo-8-(((3S,4S)-4-(ethyl-d₅)-pyrrolidin-3-yl)amino) imidazo[1,2-b]pyridazine-7-carboxamide (1.209 g, 3.37 mmol) was added. The reaction was stirred for another 30 min. and concentrated to give an orange oil. The oil was partitioned between ethyl acetate and water. The ethyl acetate layer was washed with 10% LiCl, and (sat.) sodium chloride; dried over sodium sulfate, filtered, and concentrated. The crude material was purified via flash chromatography (Isco, prepacked silica gel column eluting with 0-10% DCM-MeOH over 12 column volumes) to afford 2-bromo-8-(((3S,4S)-1-(1-cyanocyclopropanecarbonyl)-4-(ethyl-d₅)-pyrrolidin-3-yl)amino)imidazo[1,2-b]pyridazine-7-carboxamide (1.42 g, 3.15 mmol, 93% yield) as a white solid. ESI-MS (Method A): m/z 453.1 ([M+H]⁺). HPLC (Method B) Rt: 2.705 min.

Step 8: 8-(((3S,4S)-1-(1-Cyanocyclopropanecarbonyl)-4-(ethyl-d₅)pyrrolidin-3-yl)amino)-2-(1-methyl-1H-pyrazol-4-yl)imidazo[1,2-b]pyridazine-7-carboxamide

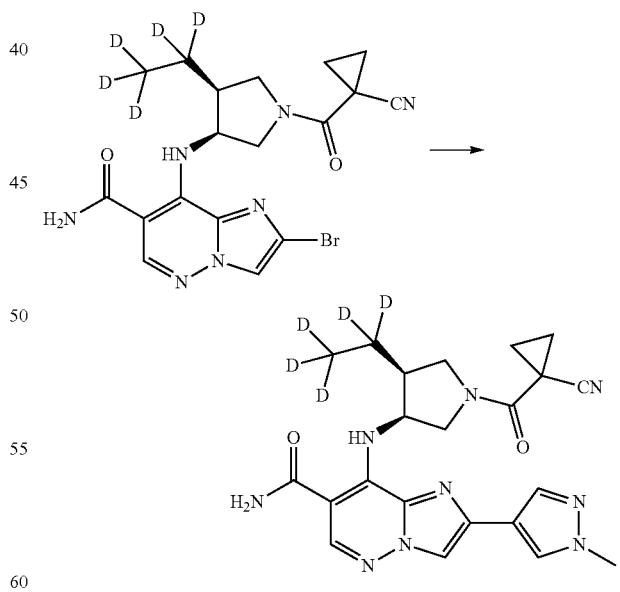

A suspension of 2-bromo-8-(((3S,4S)-1-(1-cyanocyclopropanecarbonyl)-4-(ethyl-d₅)-pyrrolidin-3-yl)amino)imidazo[1,2-b]pyridazine-7-carboxamide (250 mg, 0.554 mmol), 1-methyl-4-(4,4,5,5-tetramethyl-1,3,2-dioxaborolan-2-yl)-1H-pyrazole (346 mg, 1.662 mmol) and PdCl₂(dppf)-CH₂Cl₂ adduct (45.2 mg, 0.055 mmol) in dioxane (3693 µl) and 2M aq. potassium phosphate, tribasic (831 µl, 1.662 mmol) in a reaction vial was purged with nitrogen for 5 minutes. The vial was sealed and heated at 90° C. for 1 hr. The reaction was diluted with methanol (10 ml), filtered through CELITE®, and concentrated to yield a dark brown oil. The oil was partitioned between ethyl acetate and water. The organic layer was washed with (sat.) sodium chloride, dried over sodium sulfate, filtered and concentrated to give an oil. The crude oil (in 10% MeOH/DCM) was absorbed onto silica gel, dry loaded on the silica gel column, and purified via Isco (prepacked silica gel column eluting with 0-2% MeOH-EtOAc solvent system over 3 column volumes) to afford the title compound of Example 74 (156 mg, 0.338 mmol, 61.0% yield) as a white solid. $^1$H NMR (400 MHz, DMSO-$d_6$) δ 8.47 (s, 1H), 8.26 (d, J=2.9 Hz, 1H), 8.11 (s, 1H), 7.87 (d, J=5.3 Hz, 1H), 6.06-5.83 (m, 1H), 4.22-4.12 (m, 1H), 3.88 (s, 3H), 3.80-3.68 (m, 1H), 3.67-3.53 (m, 1H), 3.19 (t, J=11.1 Hz, 1H), 1.67-1.42 (m, 4H), 1.31-1.23 (m, 1H). ESI-MS (Method A): m/z 453.2 ([M+H]$^+$). HPLC (Method B) Rt: 2.705 min.

Example 75

8-(((3S,4S)-1-(1-Cyanocyclopropanecarbonyl)-4-(ethyl-$d_5$)pyrrolidin-3-yl)amino)-2-[(1-methyl-$d_3$)-1H-pyrazol-4-yl]imidazo[1,2-b]pyridazine-7-carboxamide

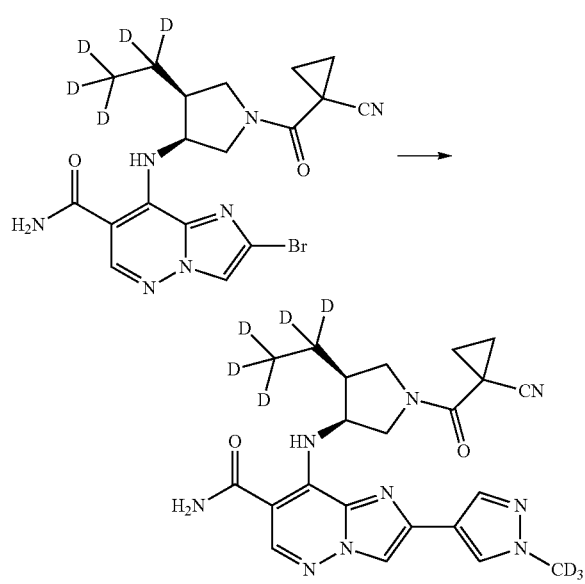

A suspension of 2-bromo-8-(((3S,4S)-1-(1-cyanocyclopropanecarbonyl)-4-(ethyl-$d_5$)-pyrrolidin-3-yl)amino)imidazo[1,2-b]pyridazine-7-carboxamide (from Step 7 of Example 74, 2.5 g, 5.54 mmol), 1-(methyl-$d_3$)-4-(4,4,5,5-tetramethyl-1,3,2-dioxaborolan-2-yl)-1H-pyrazole (3.51 g, 16.62 mmol) and PdCl$_2$(dppf)-CH$_2$Cl$_2$ Adduct (0.452 g, 0.554 mmol) and 2M aq. potassium phosphate, tribasic (8.31 ml, 16.62 mmol) in dioxane (37 ml) in a reaction vial was purged with nitrogen for 5 minutes. The vial was sealed and heated at 90° C. for 1 hr. The reaction was diluted with methanol (10 ml), filtered through CELITE®, and concentrated to yield a dark brown oil. The oil was partitioned between ethyl acetate and water. The organic layer was washed with (sat.) sodium chloride, dried over sodium sulfate, filtered, and concentrated to give an oil. The crude oil (in 10% MeOH/DCM) was absorbed onto silica gel, dry loaded on the silica gel column, and purified via Isco (eluting with 0-2% MeOH-EtOAc solvent system over 3 column volumes) to afford the title compound of Example 75 (1.63 g, 3.54 mmol, 64.0% yield) as a white solid. $^1$H NMR (400 MHz, DMSO-$d_6$) δ 8.46 (s, 1H), 8.26 (d, J=2.6 Hz, 1H), 8.10 (d, J=0.4 Hz, 1H), 7.86 (d, J=5.3 Hz, 1H), 6.06-5.82 (m, 1H), 4.22-4.11 (m, 1H), 3.79-3.67 (m, 1H), 3.67-3.51 (m, 1H), 3.23-3.14 (m, 1H), 1.66-1.41 (m, 4H), 1.32-1.23 (m, 1H). ESI-MS (Method A): m/z 456.1 ([M+H]$^+$). HPLC (Method B) Rt: 2.696 min.

Examples 76-77

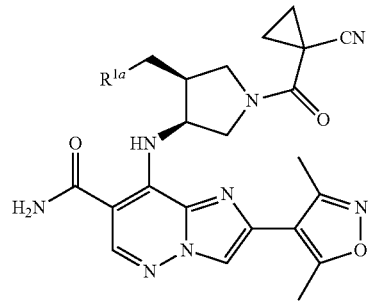

Example 76 was prepared via Suzuki coupling reaction of 2-bromo-8-(((3S,4S)-1-(1-cyanocyclopropanecarbonyl)-4-(fluoromethyl)pyrrolidin-3-yl)amino)imidazo[1,2-b]pyridazine-7-carboxamide with 3,5-dimethyl-4-(4,4,5,5-tetramethyl-1,3,2-dioxaborolan-2-yl)isoxazole following conditions analogous to Step 4 of Example 36. Similarly, Example 77 was prepared via Suzuki coupling reaction of 2-bromo-8-(((3S,4S)-1-(1-cyanocyclopropanecarbonyl)-4-ethylpyrrolidin-3-yl)amino)imidazo[1,2-b]pyridazine-7-carboxamide with tert-butyl 4-(4,4,5,5-tetramethyl-1,3,2-dioxaborolan-2-yl)-1H-pyrazole-1-carboxylate.

Example 76 was analyzed using analytical HPLC Method B and LCMS Method B; Example 77 using analytical HPLC/LCMS Method F.

| Ex. No. | Name | —R$^{1a}$ | HPLC Rt (minutes) | LCMS [m/z (M + H)] |
|---|---|---|---|---|
| 76 | 8-(((3S,4S)-1-(1-cyanocyclopropanecarbonyl)-4-(fluoromethyl)pyrrolidin-3-yl)amino)-2-(3,5-dimethylisoxazol-4-yl)imidazo[1,2-b]pyridazine-7-carboxamide | F | 2.696 | 456.10 |
| 77 | 8-(((3S,4S)-1-(1-cyanocyclopropanecarbonyl)-4-ethylpyrrolidin-3-yl)amino)-2-(3,5-dimethylisoxazol-4-yl)imidazo[1,2-b]pyridazine-7-carboxamide | CH$_3$ | 2.432 | 467.20 |

What is claimed is:

1. A compound having the formula I:

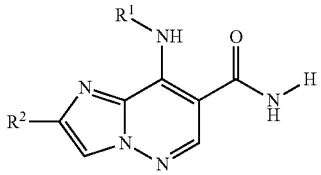

Formula I or a stereoisomer or pharmaceutically acceptable salt thereof, wherein:

$R^1$ is a 4- to 10-membered saturated or partially saturated heterocycle containing one heteroatom selected from O and $NR^{1b}$, substituted with 0-5 $R^{1a}$;

$R^{1a}$ is selected independently at each occurrence from hydrogen, =O, F, Cl, Br, $C_2D_5$, $OCF_3$, $CF_3$, CN, $NO_2$, —$(CH_2)_rOR^b$, —$(CH_2)_rSR^b$, —$(CH_2)_rC(O)R^{1d}$, —$(CH_2)_rC(O)OR^b$, —$(CH_2)_rOC(O)R^b$, —$(CH_2)_rNR^cR^c$, —$(CH_2)_rC(O)NR^cR^c$, —$(CH_2)_rNR^bC(O)R^{1c}$, —$(CH_2)_rNR^bC(O)OR^c$, —$(CH_2)_rNR^bC(O)NR^cR^c$, —$(CH_2)_rS(O)_2NR^cR^c$, —$(CH_2)_rNR^bS(O)_2R^c$, —$(CH_2)_rS(O)R^e$, —$(CH_2)_rS(O)_2R^e$, $C_{1-6}$ alkyl substituted with 0-5 $R^a$, $C_{1-6}$ haloalkyl, —$(CH_2)_r$-3-14 membered carbocycle substituted with 0-2 $R^a$, or —$(CH_2)_r$-5-7 membered heterocycle comprising carbon atoms and 1-4 heteroatoms selected from N, O, and $S(O)_p$ substituted with 0-2 $R^a$;

$R^{1b}$ is hydrogen, $CF_3$, —$(CH_2)_rOR^b$, —$(CH_2)_rSR^b$, —$(CH_2)_rC(O)R^{1d}$, —$(CH_2)_rC(O)OR^b$, —$(CH_2)_rOC(O)R^b$, —$(CH_2)_rNR^cR^c$, —$(CH_2)_rC(O)NR^cR^c$, —$(CH_2)_rNR^bC(O)R^{1c}$, —$(CH_2)_rNR^bC(O)OR^c$, —$(CH_2)_rNR^bC(O)NR^cR^c$, —$(CH_2)_rS(O)_2NR^cR^c$, —$S(O)_2NR^cR^c$, —$(CH_2)_rNR^bS(O)_2R^e$, —$(CH_2)_rS(O)R^e$, —$(CH_2)_rS(O)_2R^c$, $C_{1-6}$ alkyl substituted with 0-2 $R^a$, $C_{1-6}$ haloalkyl, —$(CH_2)_r$-3-14 membered carbocycle substituted with 0-1 $R^a$, —$(CH_2)_r$-5-7 membered heterocycle comprising carbon atoms and 1-4 heteroatoms selected from N, O, and $S(O)_p$ substituted with 0-2 $R^a$; or a —$(CH_2)_r$-5-7 membered heteroaryl comprising carbon atoms and 1-4 heteroatoms selected from N, O, and S substituted with 0-2 $R^a$;

$R^{1c}$ is independently at each occurrence hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, a 5- to 10-membered heterocycle containing 1-4 heteroatoms selected from N, O, and S, substituted with 0-3 $R^a$, a 5- to 10-membered heteroaryl containing 1-4 heteroatoms selected from N, O, and S, substituted with 0-3 $R^a$;

$R^{1d}$ is independently at each occurrence hydrogen, $C_{1-6}$ alkyl substituted with 0-2 $R^d$, $C_{1-6}$ haloalkyl, $C(O)NR^cR^c$, $C_{3-6}$ cycloalkyl substituted with 0-2 $R^d$, or —$(CH_2)_r$-phenyl substituted with 0-2 $R^a$, a 4- to 10-membered heterocycle containing 1-4 heteroatoms selected from N, O, and S, substituted with 0-3 $R^a$;

$R^2$ is —$NR^bC(O)NR^cR^c$, —$NR^bC(O)R^{2b}$, —$NR^bC(O)OR^{2d}$, —$NR^bS(O)_2R^{2b}$, —$(CH_2)_r$-$C_{6-10}$ aryl substituted with 0-3 $R^{2a}$, a —$(CH_2)_r$-5-7 membered heterocycle comprising carbon atoms and 1-4 heteroatoms selected from N, O, and $S(O)_p$ substituted with 0-3 $R^a$ or a —$(CH_2)_r$-4-10 membered heteroaryl containing 1-4 heteroatoms selected from N, O, and S substituted with 0-3 $R^{2a}$;

$R^{2a}$ is selected independently at each occurrence from =O, F, Cl, Br, $OCF_3$, $CF_3$, CN, $CD_3$, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^cR^c$, —$(CH_2)_rC(O)NR^cR^c$, —$(CH_2)_rNR^bC(O)R^{2b}$, —$(CH_2)_rNR^bC(O)OR^c$, —$NR^bC(O)NR^cR^c$, —$S(O)_2NR^cR^c$, —$NR^bS(O)_2R^c$, —$S(O)R^e$, —$S(O)_2R^e$, $(CH_2)_rNH(C=NCN)NHR^{11}$, $C_{1-6}$ alkyl substituted with 0-2 $R^a$, $C_{2-6}$ alkenyl, $C_{1-6}$ haloalkyl, —$(CH_2)_r$-3-14 membered carbocycle substituted with 0-2 $R^a$, and —$(CH_2)_r$-5-10 membered heterocycle comprising carbon atoms and 1-4 heteroatoms selected from N, O, and $S(O)_p$ substituted with 0-1 $R^a$;

$R^{2b}$ is independently at each occurrence hydrogen, $C_{1-6}$ alkyl substituted with 0-2 $R^a$, $C_{1-6}$ haloalkyl, $C_{3-6}$ cycloalkyl substituted with 0-2 $R^a$, or $(CH_2)_r$-phenyl substituted with 0-2 $R^a$, or —$(CH_2)_r$-5-10 membered heterocycle comprising carbon atoms and 1-4 heteroatoms selected from N, O, and $S(O)_p$ substituted with 0-1 $R^a$;

$R^{2d}$ is independently at each occurrence $C_{1-6}$ alkyl substituted with 0-2 $R^a$, $C_{1-6}$ haloalkyl, $C_{3-6}$ cycloalkyl substituted with 0-2 $R^a$, or $(CH_2)_r$-phenyl substituted with 0-2 $R^a$, or —$(CH_2)_r$-5-10 membered heterocycle comprising carbon atoms and 1-4 heteroatoms selected from N, O, and $S(O)_p$ substituted with 0-1 $R^a$;

$R^3$ is hydrogen, $C_{1-6}$ alkyl substituted with 0-1 $R^a$, phenyl substituted with 0-1 $R^a$, or $C_{3-6}$ cycloalkyl substituted with 0-1 $R^a$;

$R^a$ is independently at each occurrence hydrogen, =O, D, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^cR^c$, —$(CH_2)_rC(O)NR^cR^c$, —$(CH_2)_rNR^bC(O)R^c$, —$(CH_2)_rNR^bC(O)OR^c$, —$NR^bC(O)NR^cR^c$, —$S(O)_2NR^cR^c$, —$NR^bS(O)_2R^e$, —$S(O)R^e$, —$S(O)_2R^e$, $(CH_2)_rNH(C=NCN)NHR^c$, $C_{1-6}$ alkyl substituted with 0-1 $R^f$, $C_{1-6}$ haloalkyl, —$(CH_2)_r$-3-14 membered carbocycle substituted with 0-1 $R^d$, or —$(CH_2)_r$-5-7 membered heterocycle comprising carbon atoms and 1-4 heteroatoms selected from N, O, and $S(O)_p$ substituted with 0-1 $R^d$, alternatively two $R^a$ on adjacent or the same carbon atom form a cyclic acetal of the formula —O—$(CH_2)_n$—O—, or —O—$CF_2$—O—, wherein n is selected from 1 or 2;

$R^b$ is independently at each occurrence hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$, or —$(CH_2)_r$-5-7 membered heterocycle comprising carbon atoms and 1-4 heteroatoms selected from N, O, and $S(O)_p$ substituted with 0-1 $R^d$;

$R^c$ is independently at each occurrence hydrogen, $C_{1-6}$ alkyl substituted with 0-1 $R^f$, $C_{3-6}$ cycloalkyl, or $(CH_2)_r$-phenyl substituted with 0-1 $R^f$;

$R^d$ is independently at each occurrence hydrogen, F, Cl, Br, $OCF_3$, $CF_3$, CN, $NO_2$, —$OR^c$, —$(CH_2)_rC(O)R^c$, —$NR^cR^c$, —$NR^cC(O)OR^c$, —$C(O)OR^c$, —$SO_2N(R^c)_2$, $C_{1-6}$ alkyl, or $(CH_2)_r$-phenyl;

$R^e$ is independently at each occurrence $C_{1-6}$ alkyl, $C_{3-6}$ cycloalkyl, or $(CH_2)_r$-phenyl;

R$^f$ is independently at each occurrence hydrogen, halo, CN, SO$_2$-methyl, phenyl, NH$_2$, NHCO-methyl, OH or OCH$_3$;

r is 0, 1, 2, 3, or 4; and p is 0, 1, or 2.

2. A compound according to claim 1 wherein:

R$^1$ is a 4- to 10-membered saturated or partially saturated heterocycle containing one heteroatom selected from O and NR$^{1b}$, substituted with 0-2 R$^{1a}$, wherein the heterocycle is selected from pyrrolidinyl, piperidinyl, octahydrocylopentapyrrolyl, tetrahydrofuranyl, tetrahydropyranyl, oxabicycloheptane, and oxetane;

R$^{1a}$ is independently at each occurrence H, F, Cl, Br, —(CH$_2$)$_r$OR$^b$, C$_{1-6}$ alkyl substituted with 0-5R$^a$, or —(CH$_2$)$_r$-3-6 membered carbocycle substituted with 0-2 R$^a$;

R$^{1b}$ is hydrogen, —(CH$_2$)$_r$C(O)R$^{1d}$, —(CH$_2$)$_r$C(O)OR$^b$, —(CH$_2$)$_q$S(O)$_2$R$^c$, C$_{1-6}$ alkyl substituted with 0-2 R$^a$, a —(CH$_2$)$_r$-5-7 membered heterocycle comprising carbon atoms and 1-4 heteroatoms selected from N, O, and S(O)$_p$ substituted with 0-2 R$^a$; or a —(CH$_2$)$_r$-5-7 membered heteroaryl comprising carbon atoms and 1-4 heteroatoms selected from N, O, and S substituted with 0-2 R$^a$;

R$^{1d}$ is independently at each occurrence hydrogen, C$_{1-6}$ alkyl substituted with 0-2 R$^d$, C$_{1-6}$ haloalkyl, C(O)NR$^c$R$^c$, C$_{3-6}$ cycloalkyl substituted with 0-2 R$^d$, or (CH$_2$)$_r$-phenyl substituted with 0-2 R$^a$, a 4- to 10-membered heterocycle containing 1-4 heteroatoms selected from N, O, and S, substituted with 0-3 R$^a$; and r is 0, 1, or 2.

3. A compound according to claim 2 wherein:

R$^2$ is —NR$^b$C(O)R$^{2b}$, C$_{6-10}$ aryl substituted with 0-3 R$^{2a}$, or 5- to 10-membered heteroaryl containing 1-4 heteroatoms selected from N, O, and S substituted with 0-3 R$^{2a}$;

R$^{2a}$ is independently at each occurrence =O, F, Cl, Br, CF$_3$, CN, —(CH$_2$)$_r$OR$^b$, —(CH$_2$)$_r$C(O)R$^b$, —(CH$_2$)$_r$C(O)OR$^b$, —(CH$_2$)$_r$NR$^c$R$^c$, —(CH$_2$)$_r$C(O)NR$^c$R$^c$, —(CH$_2$)$_r$NR$^b$C(O)R$^{2b}$, —S(O)$_2$R$^e$, C$_{1-6}$ alkyl substituted with 0-2 R$^a$, —(CH$_2$)$_r$-3-14 membered carbocycle substituted with 0-2 R$^a$, or —(CH$_2$)$_r$-5-10 membered heterocycle comprising carbon atoms and 1-4 heteroatoms selected from N, O, and S(O)$_p$ substituted with 0-1 R$^a$;

R$^{2b}$ is independently at each occurrence C$_{1-6}$ alkyl substituted with 0-2 R$^a$ or C$_{1-6}$ haloalkyl; and r is 0, 1, or 2.

4. A compound according to claim 3 having the formula II:

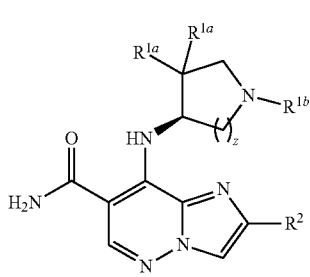

Formula II or a stereoisomer or pharmaceutically acceptable salt thereof, wherein:

R$^{1a}$ is independently at each occurrence H, F, Cl, Br, —(CH$_2$)$_r$OR$^b$, C$_{1-6}$ alkyl substituted with 0-5 R$^a$, or —(CH$_2$)$_r$-3-6 membered carbocycle substituted with 0-2 R$^a$;

R$^{1b}$ is hydrogen, —(CH$_2$)$_r$C(O)R$^{1d}$, —(CH$_2$)$_r$C(O)OR$^b$, —(CH$_2$)$_r$S(O)$_2$R$^e$, C$_{1-6}$ alkyl substituted with 0-2 R$^a$, a —(CH$_2$)$_r$-5-7 membered heterocycle comprising carbon atoms and 1-4 heteroatoms selected from N, O, and S(O)$_p$ substituted with 0-2 R$^a$; or a —(CH$_2$)$_r$-5-7 membered heteroaryl comprising carbon atoms and 1-4 heteroatoms selected from N, O, and S substituted with 0-2 R$^a$;

R$^{1d}$ is independently at each occurrence hydrogen, C$_{1-6}$ alkyl substituted with 0-2 R$^d$, C$_{1-6}$ haloalkyl, C(O)NR$^c$R$^c$, C$_{3-6}$ cycloalkyl substituted with 0-2 R$^d$, or (CH$_2$)$_r$-phenyl substituted with 0-2 R$^a$, a 4- to 10-membered heterocycle containing 1-4 heteroatoms selected from N, O, and S, substituted with 0-3 R$^a$;

R$^2$ is —NR$^b$C(O)R$^{2b}$, C$_{6-10}$ aryl substituted with 0-3 R$^{2a}$, a —(CH$_2$)$_r$-5-7 membered heterocycle comprising carbon atoms and 1-4 heteroatoms selected from N, O, and S(O)$_p$ substituted with 0-3 R$^a$ or 5- to 10-membered heteroaryl containing 1-4 heteroatoms selected from N, O, and S substituted with 0-3 R$^{2a}$;

R$^{2a}$ is independently at each occurrence =O, F, Cl, Br, CF$_3$, CD$_3$, CN, —(CH$_2$)$_r$OR$^b$, —(CH$_2$)$_r$C(O)R$^b$, —(CH$_2$)$_r$C(O)OR$^b$, —(CH$_2$)$_r$NR$^c$R$^c$, —(CH$_2$)$_r$C(O)NR$^c$R$^c$, —(CH$_2$)$_r$NR$^b$C(O)R$^{2b}$, —S(O)$_2$R$^e$, C$_{1-6}$ alkyl substituted with 0-2 R$^a$, —(CH$_2$)$_r$-3-14 membered carbocycle substituted with 0-2 R$^a$, or —(CH$_2$)$_r$-5-10 membered heterocycle comprising carbon atoms and 1-4 heteroatoms selected from N, O, and S(O)$_p$ substituted with 0-1 R$^a$;

R$^{2b}$ is independently at each occurrence C$_{1-6}$ alkyl substituted with 0-2 R$^a$ or C$_{1-6}$ haloalkyl;

R$^a$ is independently at each occurrence hydrogen, D, F, Cl, Br, CF$_3$, CN, —(CH$_2$)$_r$OR$^b$, —(CH$_2$)$_r$NR$^c$R$^c$, C$_{1-6}$ alkyl substituted with 0-1 R$^f$, or C$_{1-6}$ haloalkyl;

R$^b$ is independently at each occurrence hydrogen, C$_{1-6}$ alkyl substituted with 0-2 R$^d$, C$_{3-6}$ cycloalkyl substituted with 0-2 R$^d$, or —(CH$_2$)$_r$-5-7 membered heterocycle comprising carbon atoms and 1-4 heteroatoms selected from N, O, and S(O)$_p$ substituted with 0-1 R$^d$;

R$^c$ is independently at each occurrence hydrogen or C$_{1-6}$ alkyl;

R$^d$ is independently at each occurrence hydrogen, F, Cl, Br, CF$_3$, CN, —OR$^c$, or C$_{1-6}$ alkyl;

R$^e$ is independently at each occurrence C$_{1-6}$ alkyl;

R$^f$ is independently at each occurrence hydrogen, halo, CN, SO$_2$-methyl, phenyl, NH$_2$, NHCO-methyl, OH or OCH$_3$;

r is 0, 1, 2, 3, or 4;

p is 0, 1, or 2; and z is 1 or 2.

5. A compound according to claim 4 wherein R$^2$ is selected from NR$^b$C(O)R$^{2b}$ and a group selected from phenyl, pyridyl, indazolyl, morpholinyl, pyridinyl, quinolinyl, pyrrolidinonyl, pyrazolyl, pyrimidinyl, imidazolidinonyl, pyradizinyl, oxadiazolyl, tetrazolyl, dihydrobenzooxazinyl, pyridinonyl, oxadiazolyl, triazolyl and oxazolyl, each group substituted with 0-3 R$^{2a}$; and R$^{2a}$ is C$_{1-6}$ alkyl or C$_{3-6}$ cycloalkyl, each group substituted with 0-2 R$^a$; or =O, OR$^b$, cyano, CF$_3$, (CH$_2$)$_r$C(O)R$^b$, C(O)$_2$R$^b$, fluoro, (CH$_2$)$_r$C(O)N(R$^c$)(R$^c$), phenyl, N(R$^c$)(R$^c$), morpholinyl, S(O)$_2$Re, CD$_3$, or CH$_2$NR$^b$C(O)R$^{2b}$.

6. A compound according to claim 5 wherein $R^1$ is

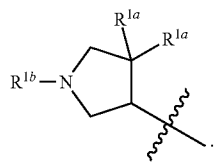

7. A compound according to claim 5 wherein $R^1$ is

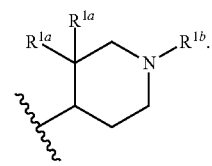

8. A compound according to claim 7, or a stereoisomer or pharmaceutically acceptable salt thereof, wherein:
$R^{1a}$ is independently at each occurrence H or $C_{1-6}$ alkyl substituted with 0-5 $R^a$;
$R^{1b}$ is
  i) hydrogen, $-(CH_2)_rC(O)R^{1d}$, $-(CH_2)_rC(O)OR^b$, or $-(CH_2)_rS(O)_2R^e$; or
  ii) $C_{1-6}$ alkyl, pyridyl, or pyridazinyl, each group substituted with 0-2 $R^a$;
$R^{1d}$ is independently at each occurrence:
  i) hydrogen, $C_{1-6}$ haloalkyl, or $C(O)NR^cR^c$;
  ii) $C_{1-6}$ alkyl, cyclopropyl, cyclobutyl or oxetane, each group substituted with 0-2 $R^d$; or
  iii) $(CH_2)_r$-phenyl substituted with 0-2 $R^a$;
$R^2$ is -phenyl, pyridyl, indazolyl, indolyl, morpholinyl, pyridinyl, quinolinyl, pyrrolidinonyl, pyrazolyl, pyrimidinyl, imidazolidinonyl, pyradizinyl, oxadiazolyl, tetrazolyl, dihydrobenzooxazinyl, pyridinonyl, oxadiazolyl, triazolyl and oxazolyl, each group substituted with 0-3 $R^{2a}$;
$R^{2a}$ is =O, $OR^b$, cyano, $CF_3$, $CHF_2$, $(CH_2)_rC(O)R^b$, $C(O)_2R^b$, fluoro, $(CH_2)_rC(O)NR^cR^c$, methyl, isopropyl, propyl, ethyl, isobutyl, cyclopropyl, $(CH_2)_2R^a$, phenyl, =O, $NR^cR^c$, $CH(R^a)_2$, morpholinyl, $C(CH_3)_2R^a$, $S(O)_2R^e$, $CD_3$, $CH_2CH(R^a)(R^a)$, $CH_2C(CH_3)_2R^a$, $CH_2CH(R^a)CH_3$, $CH^2CH(R^a)CH_2(R^a)$, $CH(R^a)_2$, $CH_2NR^bC(O)R^{2b}$ or $(CH_2)_rR^a$;
$R^{2b}$ is independently at each occurrence $C_{1-6}$ alkyl substituted with 0-2 $R^a$ or $C_{1-6}$ haloalkyl;
$R^a$ is independently at each occurrence hydrogen, D, F, Cl, Br, $CF_3$, CN, $-(CH_2)_rOR^b$, $-(CH_2)_rNR^cR^c$, $C_{1-6}$ alkyl substituted with 0-1 $R^f$ or $C_{1-6}$ haloalkyl;
$R^b$ is independently at each occurrence hydrogen, $C_{1-6}$ alkyl substituted with 0-2 $R^d$, $C_{3-6}$ cycloalkyl substituted with 0-2 $R^d$, or $-(CH_2)_r$-5-7 membered heterocycle comprising carbon atoms and 1-4 heteroatoms selected from N, O, and $S(O)_p$ substituted with 0-1 $R^d$;
$R^c$ is independently at each occurrence hydrogen or $C_{1-6}$ alkyl;
$R^d$ is independently at each occurrence hydrogen, F, Cl, Br, $CF_3$, CN, $-OR^c$, or $C_{1-6}$ alkyl;
$R^e$ is independently at each occurrence $C_{1-6}$ alkyl;
r is independently at each occurrence 0, 1, 2, 3, or 4; and
p is independently at each occurrence 0, 1, or 2.

9. A compound according to claim 8, or a stereoisomer or pharmaceutically acceptable salt thereof, wherein:

$R^{1a}$ is independently at each occurrence H or $C_{1-6}$ alkyl substituted with 0-5 $R^a$;
$R^{1b}$ is $-C(O)R^{1d}$, pyridyl, or pyridazinyl, each group substituted with 0-2 $R^a$;
$R^{1d}$ is independently at each occurrence cyclopropyl, cyclobutyl or oxetane, each group substituted with 0-2 $R^d$;
$R^2$ is pyridyl, indazolyl, indolyl, quinolinyl or pyrazolyl, each group substituted with 0-3 $R^{2a}$;
$R^{2a}$ is independently at each occurrence =O, $CD_3$, $CHF_2$, methyl, isopropyl, ethyl, cyclopropyl, $CH_2C(CH_3)_2R^a$, $CH_2CH(R^a)CH_3$, or $CH^2CH(R^a)CH_2(R^a)$;
$R^a$ is independently at each occurrence hydrogen, D, F, $CF_3$, CN, or $-(CH_2)_rOR^b$;
$R^b$ is independently at each occurrence hydrogen or $C_{1-6}$ alkyl substituted with 0-2 $R^d$; and
$R^d$ is CN.

10. A compound of claim 9 wherein $R^2$ is selected from:

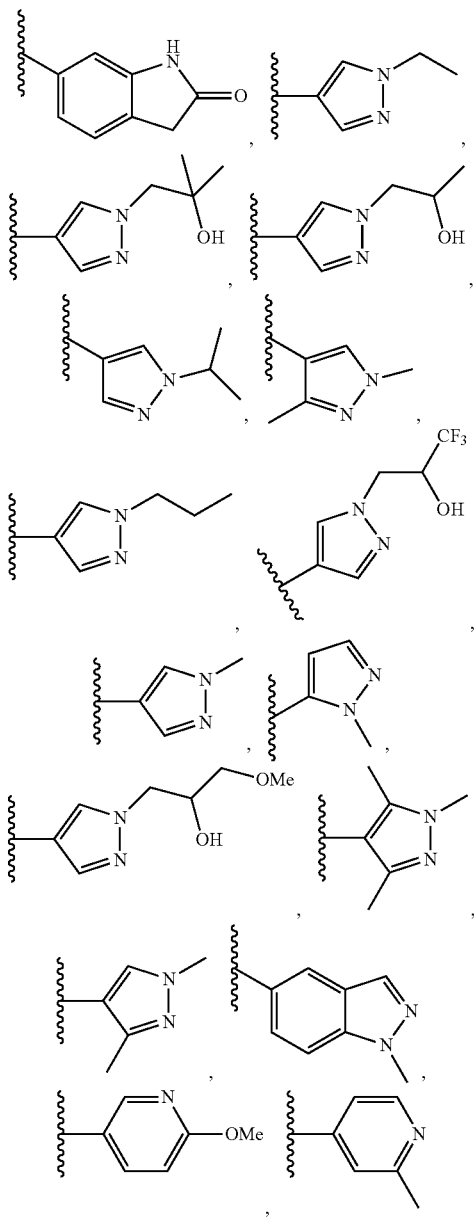

-continued

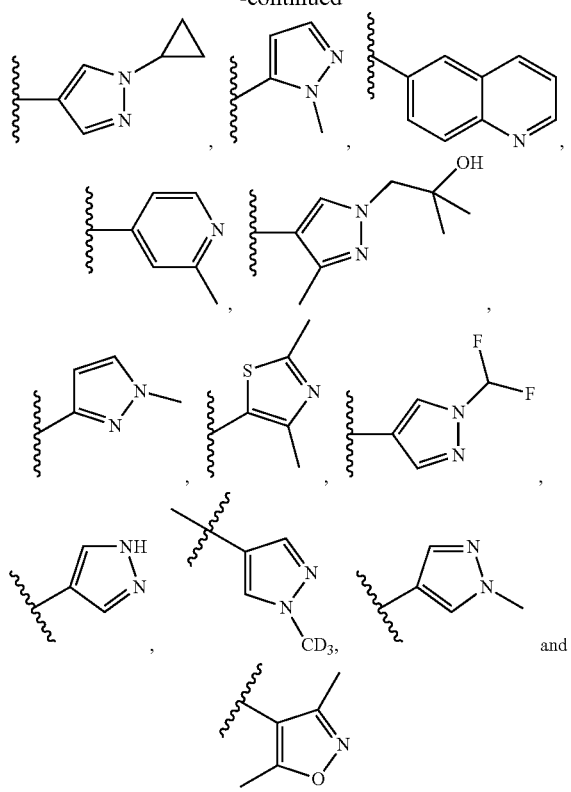

11. The compound according to claim 6 having the formula III:

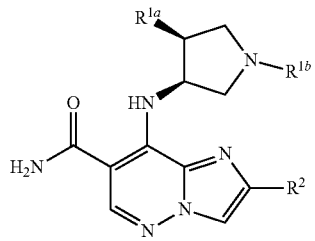

Formula III or a stereoisomer or pharmaceutically acceptable salt thereof, wherein $R^{1a}$ is selected independently at each occurrence from F, $CH_3$, $C_2H_5$, and $C_2D_5$;

$R^{1b}$ is selected independently at each occurrence from

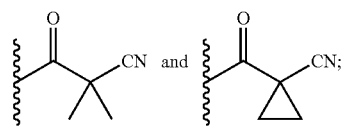

and $R^2$ is selected independently at each occurrence from

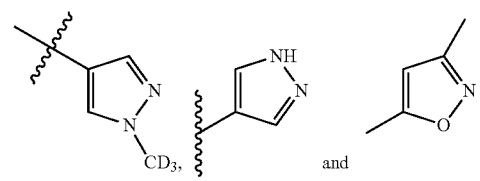

12. The compound according to claim 11 wherein $R^{1a}$ is $C_2D_5$ and $R^{1b}$ is

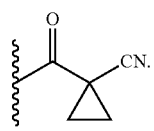 [SMILES: *C(=O)C1(C#N)CC1]

13. The compound according to claim 12, having structural formula IV:

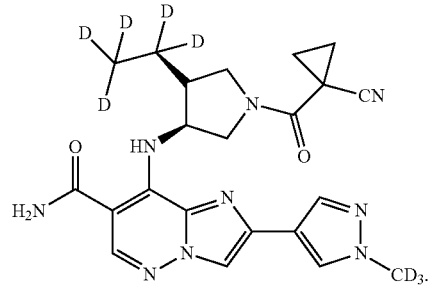

Formula IV

* * * * *